US009233951B2

(12) United States Patent
Mühlthau et al.

(10) Patent No.: US 9,233,951 B2
(45) Date of Patent: Jan. 12, 2016

(54) HETEROCYCLIC COMPOUNDS AS PESTICIDES

(75) Inventors: Friedrich August Mühlthau, Bad Soden am Taunus (DE); Thomas Bretschneider, Lohmar (DE); Reiner Fischer, Monheim (DE); Martin Füßlein, Düsseldorf (DE); Markus Heil, Leichlingen (DE); Achim Hense, Leverkusen (DE); Joachim Kluth, Langenfeld (DE); Adeline Köhler, Wuppertal (DE); Eva-Maria Franken, Leverkusen Bergisch Neukirchen (DE); Olga Malsam, Rösrath (DE); Arnd Voerste, Köln (DE); Peter Jeschke, Bergisch Gladbach (DE); Angela Becker, Düsseldorf (DE); Peter Lösel, Leverkusen (DE); Yoshitaka Sato, Ibaraki (JP)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/183,709

(22) Filed: Jul. 15, 2011

(65) Prior Publication Data

US 2012/0094837 A1 Apr. 19, 2012

Related U.S. Application Data

(60) Provisional application No. 61/364,514, filed on Jul. 15, 2010.

(30) Foreign Application Priority Data

Jul. 15, 2010 (EP) .................................... 10169682

(51) Int. Cl.
*C07D 405/04* (2006.01)
*C07D 401/04* (2006.01)
*C07D 409/04* (2006.01)

(52) U.S. Cl.
CPC ............ *C07D 405/04* (2013.01); *C07D 401/04* (2013.01); *C07D 409/04* (2013.01)

(58) Field of Classification Search
CPC .................................................... C07D 405/04
USPC ......................................... 548/400; 546/256
See application file for complete search history.

(56) References Cited

U.S. PATENT DOCUMENTS

| | | | |
|---|---|---|---|
| 3,449,350 A | 6/1969 | Walker | |
| 3,927,008 A | 12/1975 | Bailey | |
| 4,053,608 A | 10/1977 | Morisawa et al. | |
| 4,110,456 A | 8/1978 | Baldwin et al. | |
| 4,144,047 A | 3/1979 | Franz et al. | |
| 4,218,457 A | 8/1980 | Atsumi et al. | |
| 4,260,765 A | 4/1981 | Harrison et al. | |
| 4,499,097 A | 2/1985 | Tomcufcik et al. | |
| 4,743,586 A | 5/1988 | Chan | |
| 4,775,762 A | 10/1988 | Knox et al. | |
| 4,778,802 A | 10/1988 | Archibald et al. | |
| 4,863,947 A | 9/1989 | Jacobson | |
| 4,866,077 A | 9/1989 | Bogeso et al. | |
| 4,894,380 A | 1/1990 | Nyfeler et al. | |
| 5,506,191 A | 4/1996 | Anderson et al. | |
| 5,750,686 A | 5/1998 | Sunagawa et al. | |
| 6,034,093 A | 3/2000 | Ewing et al. | |
| 6,288,061 B1 | 9/2001 | Sueoka et al. | |
| 6,302,047 B1 | 10/2001 | Cannon | |
| 6,323,227 B1 | 11/2001 | Klein et al. | |
| 6,340,759 B1 | 1/2002 | Ueno et al. | |
| 6,392,047 B1 | 5/2002 | Geissler et al. | |
| 6,500,840 B2 * | 12/2002 | Myers et al. | .................. 514/305 |
| 6,506,747 B1 | 1/2003 | Betageri et al. | |
| 6,544,985 B2 | 4/2003 | Adam et al. | |
| 6,562,816 B2 * | 5/2003 | Wishka et al. | ............. 514/233.2 |
| 6,576,627 B1 | 6/2003 | Fushihara et al. | |
| 6,831,177 B1 | 12/2004 | Uenaka et al. | |
| 7,074,801 B1 | 7/2006 | Yoshida et al. | |
| 7,129,271 B2 * | 10/2006 | Maupin et al. | ................ 514/475 |
| 7,378,409 B2 | 5/2008 | Carter et al. | |
| 7,381,736 B2 | 6/2008 | Cheruvallath et al. | |
| 7,425,642 B2 | 9/2008 | Watanabe et al. | |
| 2002/0013326 A1 | 1/2002 | Tiebes et al. | |
| 2003/0069290 A1 | 4/2003 | Wishka et al. | |

(Continued)

FOREIGN PATENT DOCUMENTS

| | | |
|---|---|---|
| CA | 1 235 126 | 4/1988 |
| CA | 2 553 715 A1 | 8/2005 |

(Continued)

OTHER PUBLICATIONS

U.S. Appl. No. 13/088,026, filed Apr. 15, 2011 Bretschneider et al.*
U.S. Appl. No. 12/997,803, filed Dec. 13, 2010 Bretschneider et al.*
U.S. Appl. No. 13/054,401, filed May 17, 2011 Bretschneider et al.*
STN display, Armstrong et al., WO 2006135627 (2006).*
Brucoli et al., Journal of Combinatorial Chemistry (2009), 11(4) 576-586.*
STN/CAS online search result Wishka et al. (May 2003).*
STN/CAS online search result Myers et al. (Dec. 2002).*
Adembri, G. and Nesi, R., "Oxidation Products of 5-Isoxazolethiols and 5-Ethylthioisoxazoles: Sulfoxides, Sulfones, Sulfonic Acids, and Derivatives," *J. Heterocycl. Chem.* 9:695-697, HeteroCorporation, United States (1972).
Alvarez, A., et al., "Synthesis of 3-Arylpyrroles and 3-Pyrrolylacetylenes by Palladium-Catalyzed Coupling Reactions," *J. Org. Chem.* 57:1653-1656, American Chemical Society, United States (1992).

(Continued)

*Primary Examiner* — Scarlett Goon
*Assistant Examiner* — Sonya Wright
(74) *Attorney, Agent, or Firm* — Sterne, Kessler, Goldstein & Fox P.L.L.C.

(57) ABSTRACT

The present invention relates to novel heterocyclic compounds, to processes for preparation thereof and to the use thereof for controlling animal pests, which include arthropods and especially insects.

14 Claims, No Drawings

(56) References Cited

U.S. PATENT DOCUMENTS

| | | |
|---|---|---|
| 2003/0162812 A1 | 8/2003 | Harmsen et al. |
| 2004/0138269 A1 | 7/2004 | Sun et al. |
| 2004/0214870 A1 | 10/2004 | Xin et al. |
| 2005/0014942 A1 | 1/2005 | Maruyama et al. |
| 2005/0096362 A1 | 5/2005 | Kuo et al. |
| 2005/0131017 A1 | 6/2005 | DeGoey et al. |
| 2005/0192302 A1 | 9/2005 | Xue et al. |
| 2005/0256146 A1* | 11/2005 | Keith .......................... 514/278 |
| 2005/0267105 A1 | 12/2005 | Naidu et al. |
| 2007/0123504 A1 | 5/2007 | Bolin et al. |
| 2007/0244094 A1 | 10/2007 | Kuo et al. |
| 2008/0171741 A1 | 7/2008 | Wrobleski et al. |
| 2009/0076282 A1 | 3/2009 | Toriyabe et al. |
| 2009/0143228 A1 | 6/2009 | Kruger et al. |
| 2009/0163486 A1 | 6/2009 | Ulrich et al. |
| 2009/0170913 A1 | 7/2009 | Beck et al. |
| 2009/0239810 A1 | 9/2009 | Sundaresan et al. |
| 2009/0239860 A1 | 9/2009 | Nakamura et al. |
| 2009/0247551 A1 | 10/2009 | Jeschke et al. |
| 2009/0253749 A1 | 10/2009 | Jeschke et al. |
| 2010/0035935 A1 | 2/2010 | Koyanagi et al. |
| 2010/0240705 A1 | 9/2010 | Jeschke et al. |
| 2011/0034404 A1 | 2/2011 | Goto et al. |
| 2011/0098287 A1 | 4/2011 | Bretschneider et al. |
| 2011/0190493 A1 | 8/2011 | Bretschneider et al. |

FOREIGN PATENT DOCUMENTS

| | | |
|---|---|---|
| CA | 2 671 179 A1 | 6/2008 |
| EP | 0 539 588 A1 | 5/1993 |
| EP | 0 647 635 A1 | 4/1995 |
| EP | 1 710 233 A1 | 10/2006 |
| GB | 1 437 895 | 6/1976 |
| GB | 1 437 896 | 6/1976 |
| WO | WO 98/50385 A1 | 11/1998 |
| WO | WO99/06380 A1 | 2/1999 |
| WO | WO 00/21959 A1 | 4/2000 |
| WO | WO 00/27823 A1 | 5/2000 |
| WO | WO 03/072553 A1 | 9/2003 |
| WO | WO 03/092686 A1 | 11/2003 |
| WO | WO 2004/013130 A1 | 2/2004 |
| WO | WO 2004/019947 A1 | 3/2004 |
| WO | WO 2004/033440 A1 | 4/2004 |
| WO | WO 2004/050636 A2 | 6/2004 |
| WO | WO 2004/067524 A1 | 8/2004 |
| WO | WO 2004/091613 A2 | 10/2004 |
| WO | WO 2005/009941 A1 | 2/2005 |
| WO | WO 2005/026149 A1 | 3/2005 |
| WO | WO 2005/030206 A1 | 4/2005 |
| WO | WO 2005/033521 A1 | 4/2005 |
| WO | WO 2005/047225 A1 | 5/2005 |
| WO | WO 2005/047281 A1 | 5/2005 |
| WO | WO 2005/061494 A1 | 7/2005 |
| WO | WO 2005/061495 A1 | 7/2005 |
| WO | WO 2005/061510 A1 | 7/2005 |
| WO | WO 2005/066162 A1 | 7/2005 |
| WO | WO 2005/079791 A1 | 9/2005 |
| WO | WO 2005/082866 A2 | 9/2005 |
| WO | WO 2005/097750 A1 | 10/2005 |
| WO | WO 2005/103019 A1 | 11/2005 |
| WO | WO 2005/103043 A1 | 11/2005 |
| WO | WO 2006/044617 A1 | 4/2006 |
| WO | WO 2006/045514 A1 | 5/2006 |
| WO | WO 2006/056433 A2 | 6/2006 |
| WO | WO 2006/100288 A2 | 9/2006 |
| WO | WO 2006/100591 A1 | 9/2006 |
| WO | WO 2006/118267 A1 | 11/2006 |
| WO | WO-2006135627 * | 12/2006 |
| WO | WO 2007/043677 A1 | 4/2007 |
| WO | WO 2007/057407 A2 | 5/2007 |
| WO | WO 2007/071455 A1 | 6/2007 |
| WO | WO 2007/075567 A1 | 7/2007 |
| WO | WO 2007/075749 A2 | 7/2007 |
| WO | WO 2007/078113 A1 | 7/2007 |
| WO | WO 2007/088999 A1 | 8/2007 |
| WO | WO 2007/107758 A1 | 9/2007 |
| WO | WO 2007/131953 A1 | 11/2007 |
| WO | WO 2007/139816 A2 | 12/2007 |
| WO | WO 2007/149134 A1 | 12/2007 |
| WO | WO 2008/104503 A1 | 9/2008 |
| WO | WO 2008/111794 A1 | 9/2008 |
| WO | WO 2008/129054 A2 | 10/2008 |
| WO | WO 2009/032861 A1 | 3/2009 |
| WO | WO 2009/037485 A1 | 3/2009 |
| WO | WO 2009/061875 A2 | 5/2009 |
| WO | WO 2009/117676 A2 | 9/2009 |
| WO | WO 2009/149858 A1 | 12/2009 |
| WO | WO 2010/074747 A1 | 7/2010 |
| WO | WO 2010/074751 A1 | 7/2010 |

OTHER PUBLICATIONS

Banerjee, A.K., et al., "Synthesis and Anthelmintic Activity of 3-Substituted 5-Methylthio-isoxazoles," *Arzneimittelforschung /Drug Res.* 44(7):863-866, Aulendorf, Germany (1994).

Beck, E.M., et al., "Synthesis of Rhazinicine by a Metal-Catalyzed C—H Bond Functionalization Strategy," *Angew. Chem.* 120:3046-3049, Wiley-VCH Verlag, Germany (2008).

Billingsley, K. and Buchwald, S.L., "Highly Efficient Monophosphine-Based Catalyst for the Palladium-Catalyzed Suzuki-Miyaura Reaction of Heteroaryl Halides and Heteroaryl Boronic Acids and Esters," *J. Am. Chem. Soc.* 129:3358-3366, American Chemical Society, United States (2007).

Burger, M.T., et al., "Synthesis and Antibacterial Activity of Novel $C_{12}$ Vinyl Ketolides," *J. Med. Chem.* 49:1730-1743, American Chemical Society, United States (2006).

Cai, D., et al., "Effective lithiation of 3-bromopyridine: synthesis of 3-pyridine boronic acid and variously 3-substituted pyridines," *Tetrahedron Letters* 43:4285-4287, Elsevier Science Ltd., England (2002).

Castro, A., et al., "Synthesis, Biological Evaluation and Modeling Studies of Dual Binding Ache Inhibitors," *Med Chem. Res* 11(4):219-237, Birkhäuser Boston, United States (2002).

Chang, K.Y., et al., "Synthesis and Structure-Activity Relationships of Quaternary Ammonium Cephalosporins with 3-Pyrazolylpyridinium Derivatives," *Bioorganic & Medicinal Chemistry Letters* 10:1211-1214, Elsevier Science Ltd., England (2000).

Cheruvallath, Z.C., et al., "A Novel Solid Support for Synthesis of Oligonucleotide 3'-Phosphorothioate Monoesters," *Bioorganic & Medicinal Chemistry Letters* 13:281-284, Elsevier Science Ltd., England (2003).

Choi-Sledeski, Y.M., et al., "Sulfonamidopyrrolidinone Factor Xa Inhibitors: Potency and Selectivity Enhancements via P-1 and P-4 Optimization," *J. Med. Chem.* 42:3572-3587, American Chemical Society, United States (1999).

Cristau, H.-J., et al., "Mild Conditions for Copper-Catalysed N-Arylation of Pyrazoles," *Eur. J. Org. Chem* 4:695-709,Wiley-VCH Verlag, Germany (2004).

Denton, T.T., et al., "5-Substituted, 6-Substituted, and Unsubstituted 3-Heteroaromatic Pyridine Analogues of Nicotine as Selective Inhibitors of Cytochrome P-450 2A6," *J. Med. Chem.* 48:224-239, American Chemical Society, United States (2005).

Dose, C. and Seitz, O., "New isocysteine building blocks and chemoselective peptide ligation," *Org. Biomol. Chem.* 2:59-65, The Royal Society of Chemistry, England (2004).

Dose, C. and Seitz, O., "Single nucleotide specific detection of DNA by native chemical ligation of fluorescence labeled PNA-probes," *Bioorganic & Medicinal Chemistry* 16:65-77, Elsevier Ltd., England (2008).

Gardner, T.S., et al., "The Synthesis of Compounds for the Chemotherapy of Tuberculosis. IV. the Amide Function," *J. Org. Chem.* 19:753-757, American Chemical Society, United States (1954).

Gezginci, M.H., et al., "Antimycobacterial Activity of Substituted Isosteres of Pyridine- and Pyrazinecarboxylic Acids," *J. Med. Chem.* 44:1560-1563, American Chemical Society, United States (2001).

Gobis, K., et al., "Synthesis and Antibacterial Activity of Novel Pyridine and Pyrazine Derivatives Obtained from Amidoximes," *J. Het. Chem.* 46:1271-1279, HeteroCorporation, United States (2009).

(56) References Cited

OTHER PUBLICATIONS

González, I.C., et al., "Novel thiophenes and analogues with anthelmintic activity against *Haemonchus contortus*" *Bioorganic & Medicinal Chemistry Letters* 14(15):4037-4042, Elsevier Ltd., England (2004).

Gutierrez, C.D., et al., "ClTi(O$^i$Pr)$_3$-Promoted Reductive Amination on the Solid Phase: Combinatorial Synthesis of a Biaryl-Based Sulfonamide Library," *J. Comb. Chem.* 10:280-284, American Chemical Society, United States (2008).

Huhtiniemi, T., et al., "Oxadiazole-carbonylaminothioureas as SIRT1 and SIRT2 Inhibitors," *J. Med. Chem.* 51:4377-4380, American Chemical Society (2008).

Ishiyama, T., et al., "Synthesis of pinacol arylboronates via cross-coupling reaction of bis(pinacolato)diboron with chloroarenes catalyzed by palladium(0)-tricyclohexylphosphine complexes," *Tetrahedron* 57:9813-9816, Elsevier Science Ltd., England (2001).

Johansson, G., et al., "Antimuscarinic 3-(2-Furanyl)quinuclidin-2-ene Derivatives: Synthesis and Structure-Activity Relationshhips," *J. Med. Chem.* 40:3804-3819, American Chemical Society, United States (1997).

Kim, A.Y., et al., "Highly Efficient and Reusable Copper-Catalyzed N-Arylation of Nitrogen-Containing Heterocycles with Aryl Halides," *Molecules* 14:5169-5178, MDPI, Switzerland (2009).

Kotha, S., et al.,"Recent applications of the Suzuki-Miyaura cross-coupling reaction in organic synthesis," *Tetrahedron* 58:9633-9695, Elsevier Science Ltd., England. (2002).

Lee, S., et al., "(2-Aryl-5-methylimidazol-4-ylcarbonyl)guanidines and (2-aryl-5-methyloxazol-4-ylcarbonyl)guanidines as NHE-1 inhibitors," *Bioorganic & Medicinal Chemistry Letters* 19:1329-1331, Elsevier Ltd., England (2009).

Li, W., et al., "An Improved Protocol for the Preparation of 3-Pyridyl- and Some Arylboronic Acids," *J. Org. Chem.* 67:5394-5397, American Chemical Society, United States (2002).

Li, X., et al., "Pyridine-imide oligomers," *Chem. Commun.*:2444-2446, The Royal Society of Chemistry, England (2008).

Lipshutz, B.H., et al., "Copper-in-Charcoal (Cu/C): Heterogeneous, Copper-Catalyzed Asymmetric Hydrosilylations," *Angew. Chem.* 118:1281-1286, Wiley-VCH Verlag, Germany (2006).

Lukevics, E., et al., "Synthesis and Cytotoxicity of Silyl- and Carbonyl-Substituted Isoxazoles," *Chemistry of Heterocyclic Compounds* 36(10):1226-1231, Plenum Publishing Corporation, United States (2000).

Maeda, S., et al., "Syntheses of 2-Mercapto-4-substituted Imidazole Derivatives with Antiinflammatory Properties," *Chem. Pharm. Bull.* 32(7):2536-2543, Pharmaceutical Society of Japan , Japan (1984).

McAllister, L.A., et al., "Superactivation of the Botulinum Neurotoxin Serotype A Light Chain Metalloprotease: A New Wrinkle in Botulinum Neurotoxin," *J. Am. Chem. Soc.* 128:4176-4177, American Chemical Society, United States (2006).
Milcent, R. and Barbier, G., "Thermal Ring Transformation of 5-Aryl-2-carbazoyl-1,2,3,4-tetrazole Derivatives," *J. Het. Chem.* 24:1233-1234, HeteroCorporation, United States (1987).
Miyaura, N. and Suzuki, A., "Palladium-Catalyzed Cross-Coupling Reactions of Organoboron Compunds," *Chem. Rev.* 95-2457-2483, American Chemical Society, United States (1995).
Montalbetti, C.A.G.N. and Falque, V., "Amide bond formation and peptide coupling," *Tetrahedron* 61:10827-10852, Elsevier Ltd., England (2005).
Nam, N.L., et al., "N-o-Chlorophenylsulfonylcarbamoyl Derivatives of Pyrazoles, Pyrazolines, and Imidazole," *Chemistry of Heterocyclic Compounds* 30(1):40-43, Plenum Publishing Corporation, United States (1994).
Price, S., et al., "Identification and optimisation of a series of substituted 5-pyridin-2-yl-thiophene-2-hydroxamic acids as potent histone deacetylase (HDAC) inhibitors," *Bioorganic & Medicinal Chemistry Letters* 17:363-369, Elsevier Ltd., England (2007).
Ryzhova, E.A., et al., "Synthesis, Molecular Docking, and Biological Testing of New Selective Inhibitors of Glycogen Synthase Kinase 3β," *Pharmaceutical Chemistry Journal* 43(3):148-153, Springer Science+Business Media, Inc., United States (2009).
Singh, J.S., et al., "Fused heterocycles: Synthesis and antifungal activities of 3,10-diaryl-2-thiothiazolo[4,5-*d*]pyrido[2,1-*b*]pyrimidines and 3,6,9-triaryl-2-thiothiazolo[4,5-*d*][1,3,4]thiadiazolo[2,3,-*b*]pyrimidines," *Indian Journal of Chemistry* 33B:350-354, Council of Scientific & Industrial Research, India (1994).
Smith, J.A., et al., "The regioselective synthesis of aryl pyrroles," *Org. Biomol. Chem.* 4:2477-2482, The Royal Society of Chemistry, England (2006).
Sorokin, V.I., "Copper (I) Catalyzed *N*-Arylation of Azoles, the Recent Developments," *Mini-Reviews in Organic Chemistry* 5:323-330, Bentham Science Publishers Ltd., United Arab Emirates (2008).
Suryakiran, N., et al., "Synthesis of 3-Amino-substituted *N*-Alkylindazoles via Palladium(II)-catalyzed Intramolecular *N*-Arylation of Tosylhydrazines," *Chemistry Letters* 36(11):1370-1371, The Chemical Society of Japan, Japan (2007).
Szajda, M. and Kedzia, B., "New alkoxycarbonylalkyloxchalcones and their α,β-dibromo derivative of potential antimicrobial activity," *Pharmazie* 44:191-193, Govi-Verlag Pharmazautischer Verlag, Germany (1989).
Tao, Z-F., et al., "Discovery of 4'-(1,4-dihydro-indeno[1,2-*c*]pyrazol-3-yl)-benzonitriles and 4'-(1,4-dihydro-indeno[1,2-*c*]pyrazol-3-yl)-pyridine-2'-carbonitriles as potent checkpoint kinase 1 (Chk1) inhibitors," *Bioorganic & Medicinal Chemistry Letters* 17:5944-5951, 2007 Elsevier Ltd., England (2007).
Wan, Z-K., et al., "Monocyclic thiophenes as protein tyrosine phosphatase 1B inhibitors: Capturing interactions with Asp48," *Bioorganic & Medicinal Chemistry Letters* 16:4941-4945, Elsevier Ltd., England (2006).
Wawzonek, S. and Hansen, G.R., "The Action of Sulfur on Cyclic Amines," *J. Org. Chem.* 31: 3580-3582, American Chemical Society, United States (1966).
Zhang, J., et al., "Potent Nonpeptide Endothelin Antagonists: Synthesis and Structure-Activity Relationships of Pyrazole-5-carboxylic Acids," *Bioorganic & Medicinal Chemistry Letters* 10:2575-2578, Elsevier Science Ltd., England (2000).
English language Abstract of WIPO Patent Publication No. WO 1999/06380 A1, European Patent Office, espacenet database—Worldwide (1999).
English language Abstract of WIPO Patent Publication No. WO 2005/047225 A1, European Patent Office, espacenet database—Worldwide (2005).
English language Abstract of WIPO Patent Publication No. WO 2006/118267 A1, European Patent Office, espacenet database—Worldwide (2006).
International Search Report for International Application No. PCT/EP2011/061949, European Patent Office, The Hague, Netherlands, mailed on Jan. 30, 2012.
Dadkhah, M. and Prijs, B., "42. Über Pyridyloxazole, eine neue Klasse Dipyridyl-ähnlicher Verbindungen," *Helv. Chim. Acta* 45:375-381, Verlag Helvetica Chimica Acta, Switzerland (1962) (Abstract Only).
Delarge, J., et al., "Nouveaux dérivés du Torasémide à propriétés diurétiques," *Eur. J. Med. Chem.* 16:65-68, Editions Scientifiques Elsevier, France (1981) (Abstract only).
Office Action mailed Jan. 11, 2013, in U.S. Appl. No. 13/054,401, inventors: Bretschneider et al., § 371(c) Date: May 17, 2011, U.S. Patent and Trademark Office, Alexandria, Virginia.
Office Action mailed Aug. 9, 2012, in U.S. Appl. No. 12/997,803, inventors: Bretschneider et al., § 371(c) Date: Dec. 13, 2010, U.S. Patent and Trademark Office, Alexandria, Virginia.

* cited by examiner

HETEROCYCLIC COMPOUNDS AS PESTICIDES

The present invention relates to novel heterocyclic compounds, to processes for preparation thereof and to the use thereof for controlling animal pests, which include arthropods and especially insects.

Particular heterocyclic compounds have already become known as insecticidally active compounds (cf. WO1999/006380 A1, EP 0 097 126 B1).

Particular heterocyclic compounds have already become known as herbicidally active compounds (cf. WO 2005/047281 A1).

In addition, the following compounds have become known, but no insecticidal action has been described for them:

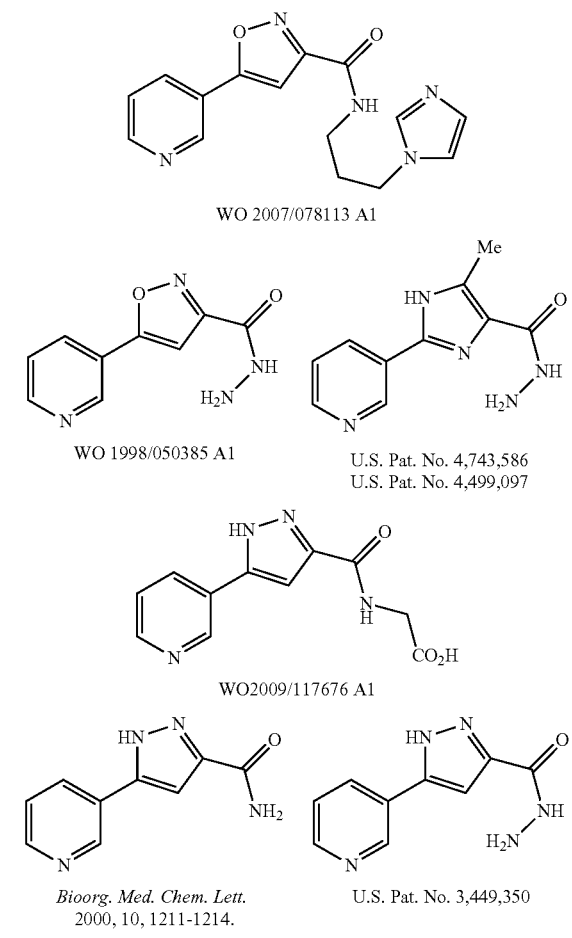

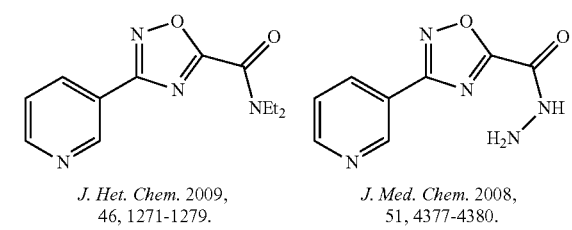

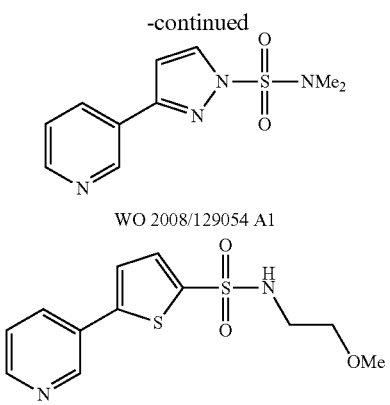

WO 2000/027823 A1, U.S. Pat. No. 6,288,061 B1, WO 1999/033827 A1, DE 28 38 892 A1, *Chem. Heterocycl. Comp.* 2000, 36, 1226-1231, WO 2000/021959 A1, EP 0647 635 A1, *Pharmazie* 1989, 44, 191-193, EP 0 097 126 B1, DE 24 53 082 A1, DE 24 53 083 A1 and U.S. Pat. No. 4,110,456 disclose heterocyclic compounds for which pharmaceutical uses are specified.

Modern crop protection compositions have to meet many demands, for example in relation to efficacy, persistence and spectrum of their action and possible use. Questions of toxicity and of combinability with other active ingredients or formulation auxiliaries play a role, as does the question of the cost and effort involved in the synthesis of an active ingredient. Furthermore, resistances may occur. For all these reasons, the search for novel crop protection compositions cannot be considered to be complete, and there is a constant need for novel compounds having properties which, compared to the known compounds, are improved at least in respect of individual aspects.

It was an object of the present invention to provide compounds which widen the spectrum of the pesticides in various aspects.

This object, and further objects which are not mentioned explicitly and can be derived or deduced from the connections discussed herein, are achieved by novel compounds of the formula (I)

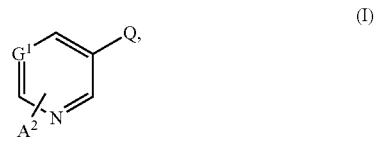

(I)

in which $G^1$ is N or $C-A^1$, $A^1$ is hydrogen, halogen, cyano, nitro, alkyl, cycloalkyl, haloalkyl, or alkoxy, $A^2$ is hydrogen, halogen, cyano, nitro, alkyl, cycloalkyl or alkoxy, Q is one of the following radicals (Q-1) to (Q-64):

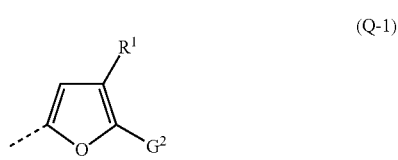

(Q-1)

-continued
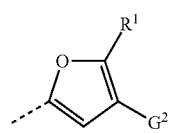 (Q-2)
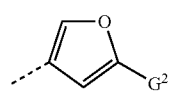 (Q-3)
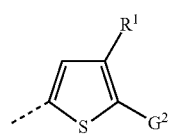 (Q-4)
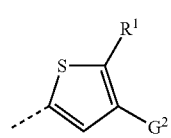 (Q-5)
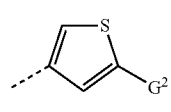 (Q-6)
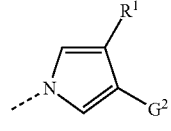 (Q-7)
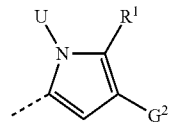 (Q-8)
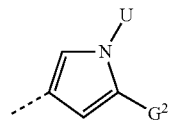 (Q-9)
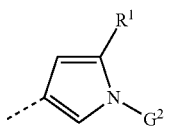 (Q-10)
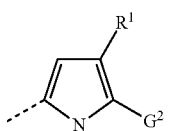 (Q-11)
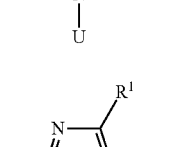 (Q-12)
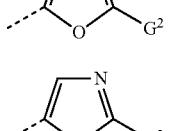 (Q-13)
-continued
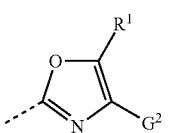 (Q-14)
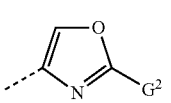 (Q-15)
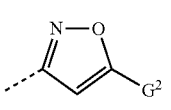 (Q-16)
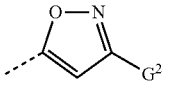 (Q-17)
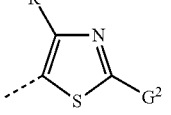 (Q-18)
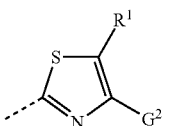 (Q-19)
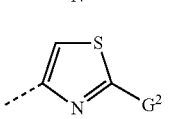 (Q-20)
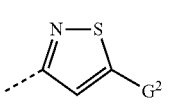 (Q-21)
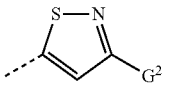 (Q-22)
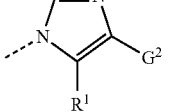 (Q-23)
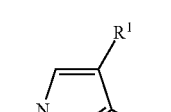 (Q-24)
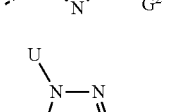 (Q-25)
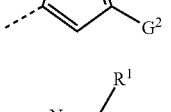 (Q-26)

-continued
(Q-27) 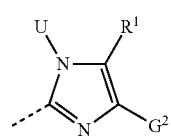
(Q-28) 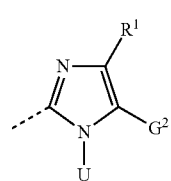
(Q-29) 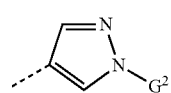
(Q-30) 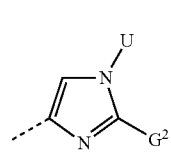
(Q-31) 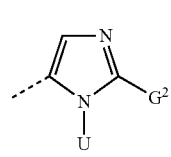
(Q-32) 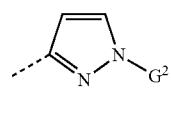
(Q-33) 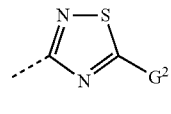
(Q-34) 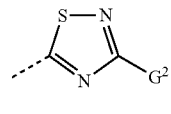
(Q-35) 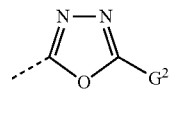
(Q-36) 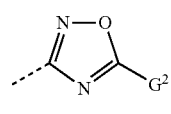
(Q-37) 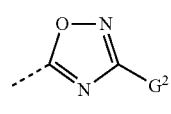
(Q-38) 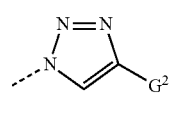
(Q-39) 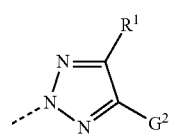
-continued
(Q-40) 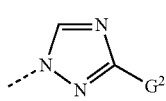
(Q-41) 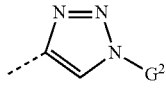
(Q-42) 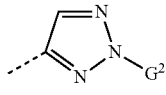
(Q-43) 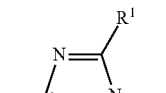
(Q-44) 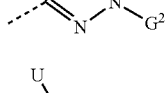
(Q-45) 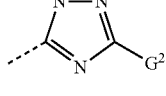
(Q-46) 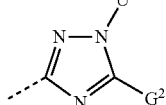
(Q-47) 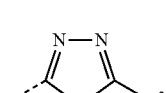
(Q-48) 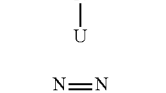
(Q-49) 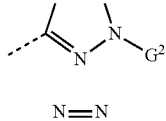
(Q-50) 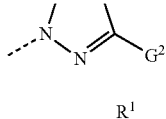
(Q-51) 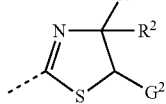
(Q-52) 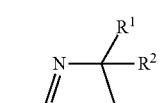

(Q-53) 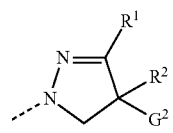

(Q-54) 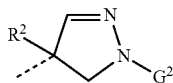

(Q-55) 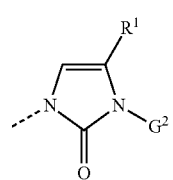

(Q-56) 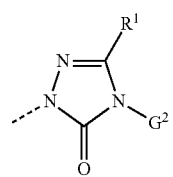

(Q-57) 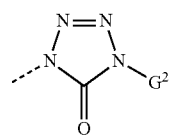

(Q-58) 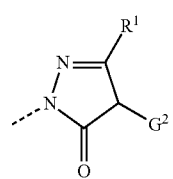

(Q-59) 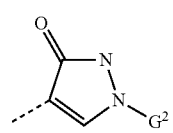

(Q-60) 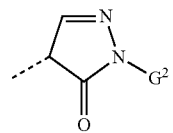

(Q-61) 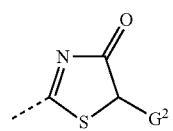

(Q-62) 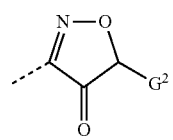

(Q-63) 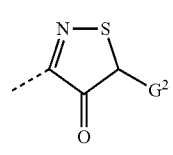

(Q-64) 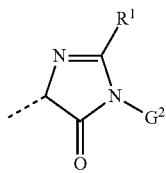

in which
the broken line denotes the bond to the adjacent ring,
U is hydrogen, alkyl, cycloalkyl or haloalkyl,
$R^1$ is hydrogen, alkyl, cycloalkyl, halogen, cyano, haloalkyl, hydroxyl or alkoxy,
$R^2$ is hydrogen, alkyl, cycloalkyl, halogen, cyano, haloalkyl, hydroxyl, alkoxy or alkoxycarbonyl,
in which, in the Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48, Q-49, Q-50, Q-51, Q-52, Q-53, Q-58, Q-61, Q-62 and Q-63 radicals,
$G^2$ is a radical from the group of $C(=X)NR^3R^4$, $C(=X)NR^3C(=Y)R^7$, $C(=X)NR^3C(=Y)OR^7$, $C(=X)NR^3C(=Y)NR^7R^8$, $C(=X)NR^3NR^9C(=Y)R^7$, $C(=X)NR^3NR^9C(=Y)OR^7$, $C(=X)NR^3S(=O)_nR^7$, $C(=X)NR^3NR^9S(=O)_nR^7$, $C(=X)NR^3P(=Y)R^{10}R^{11}$, $S(=O)_nNR^3R^4$, $S(=O)_nNR^3C(=X)R^7$, $S(=O)_nNR^3C(=X)OR^7$, $S(=O)_nNR^3C(=X)NR^7R^8$, $S(=O)_nNR^3NR^9C(=X)R^7$, $S(=O)_nNR^3NR^9C(=X)OR^7$, $S(=O)_nNR^3NR^9C(=X)NR^7R^8$, $S(=O)_nNR^3S(=O)_nR^7$, $S(=O)_nNR^3NR^9S(=O)_nR^7$, $S(=O)_nNR^3P(=Y)R^{10}R^{11}$, $NR^3C(=X)R^4$ and $NR^3S(=O)_nR^4$;
and, in the Q-10, Q-26, Q-29, Q-32, Q-41, Q-42, Q-43, Q-47, Q-54, Q-55, Q-56, Q-57, Q-59, Q-60 and Q-64 radicals,
$G^2$ is a radical from the group of $C(=X)NR^3R^4$, $S(=O)_nNR^3R^4$ and $C(=X)NR^3S(=O)_nR^7$,
in which
X and Y are each independently oxygen or sulphur,
n is 1 or 2,
$R^3$ is a radical from the group of hydrogen, alkyl, cycloalkyl, haloalkyl, cyanoalkyl, alkoxy, haloalkoxy, alkenyl, alkoxyalkyl, optionally halogen-substituted alkylcarbonyl, optionally halogen-substituted alkoxycarbonyl, optionally halogen-, alkyl-, alkoxy-, haloalkyl- and cyano-substituted cycloalkylcarbonyl, optionally substituted arylalkyl and optionally substituted hetarylalkyl, or a cation, for example a mono- or divalent metal ion (these are understood to mean, especially ions of the alkali metals and alkaline earth metals, such as lithium, sodium, potassium, magnesium and calcium,) or an optionally alkyl- or arylalkyl-substituted ammonium ion,
$R^4$ is a radical from the group of hydrogen, cyano, optionally substituted alkyl, optionally substituted alkenyl, optionally substituted alkynyl, alkoxy, haloalkoxy, optionally halogen-substituted alkoxyalkyl, optionally halogen-substituted bis(alkoxy)alkyl, optionally halogen-substituted alkylthioalkyl, optionally halogen-substituted bis(alkylthio)alkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkynyloxy, in each case optionally substituted cycloalkyl, cycloalkenyl, cycloalkylcarbonyl and cycloalkylalkyl, in which the rings may contain at least one heteroatom from the group of sulphur, oxygen (where oxygen atoms must not be immediately adjacent) and nitrogen, optionally substituted aryl, optionally substituted heteroaryl, optionally substituted heterocyclyl, optionally substituted heterocyclylalkyl, optionally substituted arylalkyl, optionally substituted hetarylalkyl and $NR^5R^6$ in which $R^5$ and $R^6$ are each independently a radical from the group of hydrogen, alkyl, haloalkyl, cycloalkyl, alkoxy (with the proviso that $R^5$ and $R^6$ are not both alkoxy), alkylcarbonyl, alkoxycarbonyl, hetaryl and heterocyclyl, or $R^5$ and $R^6$ together with the nitrogen atom to which they are bonded form an optionally substituted hetrocycle, or $R^3$ and $R^4$ together with the nitrogen atom to which they are bonded form an optionally substituted ring optionally containing one or more further heteroatoms from the group of sulphur, oxygen (where oxygen atoms must not be immediately adjacent) and nitrogen, $R^7$ and $R^8$ are each independently hydrogen or an in each case optionally substituted radical from the group of alkyl, alkenyl, alkynyl, cycloalkyl, cycloalkylalkyl, cycloalkenyl, in which the rings may contain at least one heteroatom from the group of sulphur, oxygen (where oxygen atoms must not be immediately adjacent) and nitrogen, and in each case optionally substituted aryl, heteroaryl, arylalkyl and heteroarylalkyl or $R^7$ and $R^8$ together with the nitrogen atom to which they are bonded form a saturated or unsaturated and optionally substituted 4- to 8-membered ring which may contain one or more further heteroatoms from the group of sulphur, oxygen (where oxygen atoms must not be immediately adjacent) and nitrogen, $R^9$ is a radical from the group of hydrogen, alkyl, cycloalkyl, haloalkyl, alkoxy, haloalkoxy, alkenyl, alkoxyalkyl, optionally halogen-substituted alkylcarbonyl, optionally halogen-substituted alkoxycarbonyl, optionally halogen-substituted cycloalkylcarbonyl, optionally substituted arylalkyl and optionally substituted hetarylalkyl, $R^{10}$ and $R^{11}$ are each independently an in each case optionally substituted radical from the group of alkyl, alkenyl, alkoxy, alkenyloxy, alkynyloxy, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, or $R^{10}$ and $R^{11}$ together with the phosphorus atom to which they are bonded form a saturated or unsaturated and optionally substituted 5- to 7-membered ring which may contain one or two heteroatoms from the group of oxygen (where oxygen atoms must not be immediately adjacent) and sulphur, and salts N-oxides and tautomeric forms of the compounds of the formula (I).

The compounds of the formula (I) may, where appropriate, depending on the nature of the substituents, be in the form of geometric and/or optically active isomers or corresponding isomer mixtures of varying composition. The invention relates both to the pure isomers and to the isomer mixtures.

The inventive compounds may also be present as metal complexes, as described for other amides, for example in DE 2221647.

Preferred substituents or ranges of the radicals shown in the compounds of the formula (I) are elucidated below.

G' is N or C-$A^1$.

$A^1$ is hydrogen, halogen, cyano, nitro, $C_1$-$C_6$-alkyl, $C_3$-$C_6$-cycloalkyl, $C_1$-$C_3$-haloalkyl or $C_1$-$C_6$-alkoxy.

$A^2$ is hydrogen, halogen, cyano, nitro, $C_1$-$C_6$-alkyl, $C_3$-$C_6$-cycloalkyl or $C_1$-$C_6$-alkoxy.

Q is Q-1, Q-2, Q-4, Q-7, Q-12, Q-16, Q-19, Q-21, Q-26, Q-29, Q-34, Q-35, Q-37, Q-40, Q-42, Q-48, Q-54 or Q-60.

U is hydrogen, $C_1$-$C_6$-alkyl, $C_3$-$C_6$-cycloalkyl or $C_1$-$C_3$-haloalkyl.

$R^1$ is hydrogen, $C_1$-$C_6$-alkyl, $C_3$-$C_6$-cycloalkyl, halogen, cyano, $C_1$-$C_3$-haloalkyl, hydroxyl or $C_1$-$C_6$-alkoxy.

$R^2$ is hydrogen, $C_1$-$C_6$-alkyl, halogen, cyano, hydroxyl, $C_1$-$C_6$-alkoxy or $C_1$-$C_3$-alkoxycarbonyl.

$G^2$ in the Q-1, Q-2, Q-4, Q-7, Q-12, Q-16, Q-19, Q-21, Q-34, Q-35, Q-37, Q-40 and Q-48 radicals
is a radical from the group of C(=X)$NR^3R^4$, C(=X)$NR^3$C(=Y)$R^7$, C(=X)$NR^3$C(=Y)$OR^7$, C(=X)$NR^3$C(=Y)$NR^7R^8$, C(=X)$NR^3$S(=O)$_n$$R^7$, S(=O)$_n$$NR^3R^4$, S(=O)$_n$$NR^3$C(=X)$R^7$, S(=O)$_n$$NR^3$C(=X)$OR^7$, S(=O)$_n$$NR^3$C(=X)$NR^7R^8$, $NR^3$C(=X)$R^4$ and $NR^3$S(=O)$_n$$R^4$, $G^2$ in the Q-26, Q-29, Q-42, Q-54 and Q-60 radicals
is C(=X)$NR^3R^4$ or S(=O)$_n$$NR^3R^4$.

X and Y are each independently oxygen or sulphur.

n is 1 or 2.

$R^3$ is a radical from the group of hydrogen, $C_1$-$C_6$-alkyl, $C_3$-$C_6$-cycloalkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, optionally halogen-substituted $C_1$-$C_6$-alkylcarbonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or a cation, for example a mono- or divalent metal ion or an optionally $C_1$-$C_6$-alkyl- or aryl-$C_1$-$C_6$-alkyl-substituted ammonium ion.

$R^4$ is a radical from the group of hydrogen, cyano, in each case optionally halogen-, cyano-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl and $C_2$-$C_6$-alkynyl, $C_1$-$C_6$-alkoxy, $C_1$-$C_6$-haloalkoxy, optionally halogen-substituted bis($C_1$-$C_6$-alkoxy)-$C_1$-$C_6$-alkyl, optionally halogen-substituted bis($C_1$-$C_6$-alkylthio)-$C_1$-$C_6$-alkyl, optionally halogen-substituted $C_1$-$C_6$-alkylcarbonyl-$C_1$-$C_6$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, optionally halogen-substituted $C_1$-$C_6$-alkoxycarbonyl-$C_1$-$C_6$-alkyl, $C_2$-$C_4$-alkynyloxy, optionally halogen-substituted $C_3$-$C_6$-cycloalkylcarbonyl, optionally halogen-substituted $C_3$-$C_6$-cycloalkyl-$C_1$-$C_6$-alkyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl and $C_3$-$C_6$-cycloalkenyl, in which the rings may contain one to three heteroatoms from the group of sulphur, oxygen (where oxygen atoms must not be immediately adjacent) and nitrogen, in each case optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, heterocyclyl, heterocyclyl-$C_1$-$C_6$-alkyl, aryl-$C_1$-$C_6$-alkyl, heteroaryl-$C_1$-$C_6$-alkyl, or $NR^5R^6$ in which $R^5$ and $R^6$ are each independently a radical from the group of hydrogen, $C_1$-$C_6$- alkyl, $C_1$-$C_6$-haloalkyl, $C_3$-$C_6$-cycloalkyl, $C_1$-$C_6$-alkoxy, $C_1$-$C_6$-alkylcarbonyl, $C_1$-$C_6$-alkoxylcarbonyl, hetaryl and heterocyclyl, or $R^5$ and $R^6$ together with the nitrogen atom to which they are bonded form an optionally halogen-substituted heterocycle.

$R^3$ and $R^4$ may also, together with the nitrogen atom to which they are bonded, form an optionally $C_1$-$C_6$-alkyl-, $C_1$-$C_6$-alkoxy- or halogen-substituted 3- to 7-membered ring optionally containing one or two heteroatoms from the group of oxygen, nitrogen and sulphur, where oxygen atoms must not be immediately adjacent.

$R^7$ and $R^8$ are each independently hydrogen or an in each case optionally halogen-substituted radical from the group of $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and $C_3$-$C_6$-cycloalkenyl, in which the rings may contain one to three heteroatoms from the group of sulphur, oxygen (where oxygen atoms must not be immediately adjacent) and nitrogen, and in each case optionally halogen-, cyano-, $C_1$-$C_6$-alkyl-substituted aryl, heteroaryl, arylalkyl and heteroarylalkyl.

$R^7$ and $R^8$ may also, together with the nitrogen atom to which they are bonded, form a saturated or unsaturated and optionally substituted 4- to 8-membered ring which may contain one to four further heteroatoms from the group of sulphur, oxygen (where oxygen atoms must not be immediately adjacent) and nitrogen, $R^9$ is a radical from the group of hydrogen, $C_1$-$C_6$-alkyl, $C_3$-$C_6$-cycloalkyl, halo-$C_1$-$C_6$-alkyl, $C_1$-$C_6$-alkoxy, halo-$C_1$-$C_6$-alkoxy, $C_2$-$C_6$-alkenyl, $C_1$-$C_6$-alkoxy-$C_1$-$C_6$-alkyl, optionally halogen-substituted $C_1$-$C_6$-alkylcarbonyl, optionally halogen-substituted $C_1$-$C_6$-alkoxycarbonyl, optionally halogen-substituted $C_3$-$C_6$-cycloalkylcarbonyl, optionally halogen-, cyano-, $C_1$-$C_3$-haloalkyl- or $C_1$-$C_3$-alkoxy-substituted aryl-$C_1$-$C_6$-alkyl and optionally halogen-, cyano-, $C_1$-$C_3$-haloalkyl- or $C_1$-$C_3$-alkoxy-substituted hetaryl-$C_1$-$C_6$-alkyl.

$R^{10}$ and $R^{11}$ are each independently an in each case optionally halogen- or cyano-substituted radical from the group of $C_1$-$C_6$-alkyl, $C_2$-$C_6$-alkenyl, $C_1$-$C_6$-alkoxy, $C_2$-$C_6$-alkenyloxy, $C_2$-$C_6$-alkynyloxy, $C_3$-$C_6$-cycloalkyloxy, $C_3$-$C_6$-cycloalkenyloxy, $C_3$-$C_6$-cycloalkyl-$C_1$-$C_6$-alkyloxy, $C_1$-$C_6$-alkylthio, $C_2$-$C_6$-alkenylthio, phenoxy, phenylthio, benzyloxy, benzylthio, heteroaryloxy, heteroarylthio, heteroarylalkoxy and heteroarylalkylthio.

$R^{10}$ and $R^{11}$ may also, together with the phosphorus atom to which they are bonded, form a saturated or unsaturated and optionally halogen-, cyano-, $C_1$-$C_4$-alkyl-, $C_1$-$C_3$-haloalkyl- or $C_1$-$C_3$-alkoxy-substituted 5- to 7-membered ring which may contain one or two heteroatoms from the group of oxygen (where oxygen atoms must not be immediately adjacent) and sulphur.

Particularly preferred substituents or ranges of the radicals shown in the compounds of the formula (I) are elucidated below.

$G^1$ is N or C-$A^1$, $A^1$ is hydrogen, halogen, cyano, nitro, $C_1$-$C_4$-alkyl, $C_3$-$C_6$-cycloalkyl, $C_1$-$C_3$-haloalkyl or $C_1$-$C_4$-alkoxy.

$A^2$ is hydrogen, halogen, cyano, nitro, $C_1$-$C_4$-alkyl, $C_3$-$C_6$-cycloalkyl or $C_1$-$C_4$-alkoxy.

Q is Q-1, Q-2, Q-4, Q-7, Q-12, Q-16, Q-19, Q-21, Q-26, Q-29, Q-34, Q-35, Q-37, Q-40, Q-42, Q-48, Q-54 and Q-60.

U is hydrogen, $C_1$-$C_4$-alkyl, $C_3$-$C_6$-cycloalkyl or $C_1$-$C_3$-haloalkyl.

$R^1$ is hydrogen, $C_1$-$C_4$-alkyl, $C_3$-$C_6$-cycloalkyl, halogen, cyano, $C_1$-$C_3$-haloalkyl, hydroxyl or $C_1$-$C_4$-alkoxy.

$R^2$ is hydrogen, $C_1$-$C_4$-alkyl, halogen, cyano, hydroxyl, $C_1$-$C_4$-alkoxy or $C_1$-$C_3$-alkoxycarbonyl.

$G^2$ in the Q-1, Q-2, Q-4, Q-7, Q-12, Q-16, Q-19, Q-21, Q-34, Q-35, Q-37, Q-48 and Q-60 radicals
is a radical from the group of $C(=X)NR^3R^4$, $C(=X)NR^3C(=Y)R^7$, $C(=X)NR^3C(=Y)OR^7$, $C(=X)NR^3C(=Y)NR^7R^8$, $C(=X)NR^3S(=O)_nR^7$, $S(=O)_nNR^3R^4$, $S(=O)_nNR^3C(=X)R^7$, $S(=O)_nNR^3C(=X)OR^7$, $S(=O)_nNR^3C(=X)NR^7R^8$, $NR^3C(=X)R^4$ and $NR^3S(=O)_nR^4$.

$G^2$ in the Q-26, Q-29, Q-40, Q-42 and Q-54 radicals
is $C(=X)NR^3R^4$ or $S(=O)_nNR^3R^4$.

X and Y are each independently oxygen or sulphur.

n is 1 or 2.

$R^3$ is a radical from the group of hydrogen, $C_1$-$C_4$-alkyl, $C_3$-$C_6$-cycloalkyl, $C_1$-$C_4$-haloalkyl, cyano-$C_1$-$C_4$-alkyl, $C_1$-$C_4$-alkoxy, $C_1$-$C_4$-haloalkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl, optionally halogen-, $C_1$-$C_4$-alkyl-, $C_1$-$C_4$-alkoxy-, $C_1$-$C_4$-haloalkyl- and cyano-substituted $C_3$-$C_6$-cycloalkylcarbonyl, or a cation, for example a mono- or divalent metal ion or an optionally $C_1$-$C_4$-alkyl- or aryl-$C_1$-$C_4$-alkyl-substituted ammonium ion.

$R^4$ is a radical from the group of hydrogen, cyano, in each case optionally halogen-, cyano-, $C_1$-$C_4$-alkoxy-, $C_1$-$C_4$-haloalkoxy-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_1$-$C_4$-alkenyl and $C_2$-$C_4$-alkynyl $C_1$-$C_4$-alkoxy, $C_1$-$C_4$-haloalkoxy, optionally halogen-substituted bis($C_1$-$C_4$-alkoxy)-$C_1$-$C_4$-alkyl, optionally halogen-substituted bis ($C_1$-$C_4$-alkylthio)-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, optionally halogen-substituted $C_1$-$C_4$-alkoxycarbonyl-$C_1$-$C_4$-alkyl, $C_2$-$C_4$-alkynyloxy, optionally halogen-substituted $C_3$-$C_6$-cycloalkylcarbonyl, optionally halogen-substituted $C_3$-$C_6$-cycloalkyl-$C_1$-$C_4$-alkyl, in each case optionally halogen-, $C_1$-$C_4$-alkyl-, $C_1$-$C_4$-haloalkyl-, $C_1$-$C_4$-alkoxy- or $C_1$-$C_4$-haloalkoxy-substituted $C_3$-$C_6$-cycloalkyl and $C_3$-$C_6$-cycloalkenyl in which the rings may contain one to three heteroatoms from the group of sulphur, oxygen (where oxygen atoms must not be immediately adjacent) and nitrogen, in each case optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, heterocyclyl, heterocyclyl-$C_1$-$C_4$-alkyl, aryl-$C_1$-$C_4$-alkyl, heteroaryl-$C_1$-$C_4$-alkyl, or $NR^5R^6$ in which $R^5$ and $R^6$ are each independently a radical from the group of hydrogen, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylcarbonyl, $C_1$-$C_4$-alkoxylcarbonyl, hetaryl and heterocyclyl, or $R^5$ and $R^6$ together with the nitrogen atom to which they are bonded form an optionally halogen-substituted heterocycle.

$R^3$ and $R^4$ may also, together with the nitrogen atom to which they are bonded, form an optionally $C_1$-$C_4$-alkoxy- or halogen-substituted 3- to 7-membered ring optionally containing one or two heteroatoms from the group of oxygen, nitrogen and sulphur, where oxygen atoms must not be immediately adjacent.

$R^7$ and $R^8$ are each independently hydrogen or an in each case optionally halogen-substituted radical from the group of $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl and $C_3$-$C_6$-cycloalkenyl, in which the rings may contain one to three heteroatoms from the group of sulphur, oxygen (where oxygen atoms must not be immediately adjacent) and nitrogen, and in each case optionally halogen-, cyano-, $C_1$-$C_4$-alkyl-substituted aryl, heteroaryl, arylalkyl and heteroarylalkyl.

$R^7$ and $R^8$ may also, together with the nitrogen atom to which they are bonded, form a saturated or unsaturated and optionally substituted 4- to 8-membered ring which may contain one to four further heteroatoms from the group of sulphur, oxygen (where oxygen atoms must not be immediately adjacent) and nitrogen, for example a radical from the group of pyrrolidine, piperidine, morpholine and thiomorpholine.

$R^9$ is a radical from the group of hydrogen, $C_1$-$C_4$-alkyl, $C_3$-$C_6$-cycloalkyl, halo-$C_1$-$C_4$-alkyl, $C_1$-$C_4$-alkoxy, halo-$C_1$-$C_4$-alkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl, optionally halogen-substituted $C_3$-$C_6$-cycloalkylcarbonyl, optionally halogen-, cyano-, $C_1$-$C_3$-haloalkyl- or $C_1$-$C_3$-alkoxy-substituted aryl-$C_1$-$C_4$-alkyl and optionally halogen-, cyano-, $C_1$-$C_3$-haloalkyl- or $C_1$-$C_3$-alkoxy-substituted hetaryl-$C_1$-$C_4$-alkyl.

$R^{10}$ and $R^{11}$ are each independently an in each case optionally halogen- or cyano-substituted radical from the group of $C_1$-$C_4$-alkyl, $C_2$-$C_4$-alkenyl, $C_1$-$C_4$-alkoxy, $C_2$-$C_4$-alkenyloxy, $C_2$-$C_4$-alkynyloxy, $C_3$-$C_6$-cycloalkyloxy, $C_3$-$C_6$-cycloalkenyloxy, $C_3$-$C_6$-cycloalkyl-$C_1$-$C_4$-alkyloxy, $C_1$-$C_4$-alkylthio, $C_2$-$C_4$-alkenylthio, phenoxy, phenylthio, benzyloxy, benzylthio, heteroaryloxy, heteroarylthio, heteroarylalkyloxy and heteroarylalkylthio.

$R^{10}$ and $R^{11}$ may also, together with the phosphorus atom to which they are bonded, form a saturated or unsaturated and optionally halogen-, cyano-, $C_1$-$C_4$-alkyl-, $C_1$-$C_3$-haloalkyl- or $C_1$-$C_3$-alkoxy-substituted 5- to 7-membered ring which may contain one or two heteroatoms from the group of oxygen (where oxygen atoms must not be immediately adjacent) and sulphur.

Very particularly preferred substituents or ranges of the radicals shown in the compounds of the formula (I) are elucidated below.

$G^1$ is C-$A^1$.
$A^1$ is hydrogen.
$A^2$ is hydrogen.
Q is Q-1, Q-2, Q-4, Q-7, Q-12, Q-16, Q-17, Q-19, Q-21, Q-23, Q-26, Q-34, Q-35, Q-37, Q-38 or Q-49.
$R^1$ is hydrogen or $C_1$-$C_4$-alkyl.
$G^2$ is C(=X)NR$^3$R$^4$,
X is oxygen.
$R^3$ is a radical from the group of hydrogen and $C_1$-$C_4$-alkyl.
$R^4$ is a radical from the group of hydrogen, in each case optionally halogen-, cyano- and $C_1$-$C_4$-alkylthio-substituted $C_1$-$C_4$-alkyl and $C_2$-$C_4$-alkenyl, is $C_2$-$C_4$-alkynyl, optionally halogen-substituted $C_3$-$C_6$-cycloalkyl-$C_1$-$C_4$-alkyl and optionally $C_1$-$C_4$-haloalkyl-substituted heteroaryl-$C_1$-$C_4$-alkyl.

$R^3$ and $R^4$ may also, together with the nitrogen atom to which they are bonded, form a 3- to 7-membered ring which does not contain any further heteroatoms.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (including as part of a larger unit, for example hetarylalkyl) is selected from the group of thienyl, pyrimidyl, oxadiazolyl, oxazolyl, pyrazinyl, imidazolyl, thiazolyl and furanyl.

In the very particularly preferred definitions, unless stated otherwise, halogen is selected from the group of fluorine, chlorine, bromine and iodine, preferably in turn from the group of fluorine, chlorine and bromine, hetaryl (including as part of a larger unit, for example hetarylalkyl) is selected from the group of thienyl, pyrimidyl and thiazolyl.

Halogen-substituted radicals, for example haloalkyl, are mono- or polyhalogenated up to the maximum possible number of substituents. In the case of polyhalogenation, the halogen atoms may be the same or different. Halogen here is fluorine, chlorine, bromine or iodine, especially fluorine, chlorine or bromine.

Preference, particular preference and very particular preference is given to compounds which bear the substituents specified under preferred, particularly preferred and very particularly preferred, respectively.

Saturated or unsaturated hydrocarbon radicals, such as alkyl or alkenyl, may in each case be straight-chain or branched as far as possible, including in combination with heteroatoms, as, for example, in alkoxy.

Optionally substituted radicals may be mono- or polysubstituted, where the substituents in the case of polysubstitations may be identical or different.

If, in the definitions given above, two radicals, together with a nitrogen atom to which they are bonded, can form a ring, this ring is, for example, a radical from the group of pyrrolidine, piperidine, morpholine and thiomorpholine.

The radical definitions or elucidations given above, in general terms or within areas of preference, apply both to the end products and correspondingly to the starting materials and intermediates.

These radical definitions can be combined with one another as desired, i.e. including combinations between the respective preferred ranges.

Preference is given in accordance with the invention to the compounds of the formula (I) in which a combination of the definitions listed above as preferred is present.

Particular preference is given in accordance with the invention to the compounds of the formula (I) in which a combination of the definitions listed above as particularly preferred is present.

Very particular preference is given in accordance with the invention to the compounds of the formula (I) in which a combination of the definitions listed above as very particularly preferred is present.

In a preferred embodiment, the invention relates to compounds of the formula (I-1a)

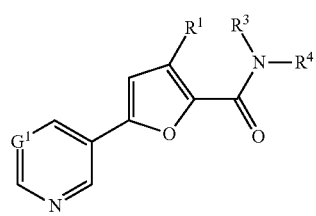

(I-1a)

in which $G^1$, $R^1$, $R^3$ and $R^4$ are each as defined above.

In a further preferred embodiment, the invention relates to compounds of the formula (I-2a)

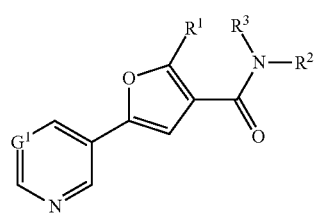

(I-2a)

in which $G^1$, $R^1$, $R^3$ and $R^4$ are each as defined above.

In a further preferred embodiment, the invention relates to compounds of the formula (I-4-a)

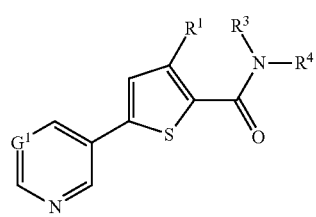

(I-4a)

in which $G^1$, $R^1$, $R^3$ and $R^4$ are each as defined above.

In a further preferred embodiment, the invention relates to compounds of the formula (I-7a)

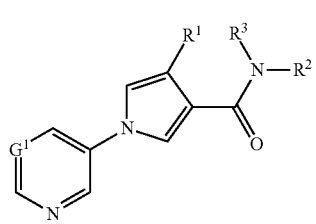

(I-7a)

in which $G^1$, $R^1$, $R^3$ and $R^4$ are each as defined above.

In a further preferred embodiment, the invention relates to compounds of the formula (I-12a)

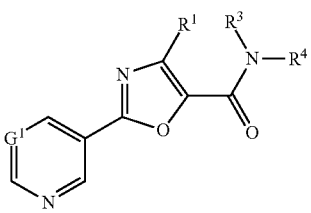

(I-12a)

in which $G^1$, $R^1$, $R^3$ and $R^4$ are each as defined above.

In a further preferred embodiment, the invention relates to compounds of the formula (I-16a)

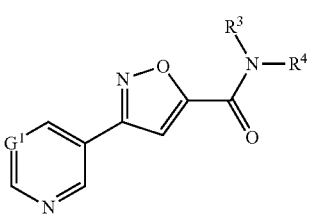

(I-16a)

in which $G^1$, $R^3$ and $R^4$ are each as defined above.

In a further preferred embodiment, the invention relates to compounds of the formula (I-17a)

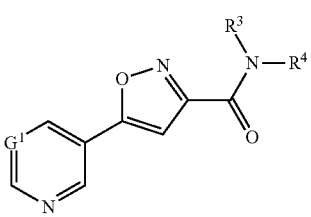

(I-17a)

in which $G^1$, $R^3$ and $R^4$ are each as defined above.

In a further preferred embodiment, the invention relates to compounds of the formula (I-18a)

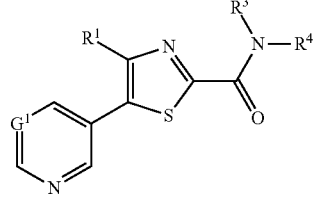
(I-18a)

in which $G^1$, $R^1$, $R^3$ and $R^4$ are each as defined above.

In a further preferred embodiment, the invention relates to compounds of the formula (I-19a)

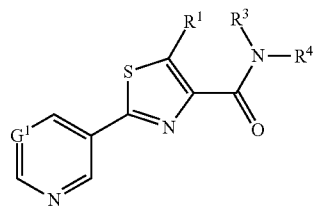
(I-19a)

in which $G^1$, $R^1$, $R^3$ and $R^4$ are each as defined above.

In a further preferred embodiment, the invention relates to compounds of the formula (I-21a)

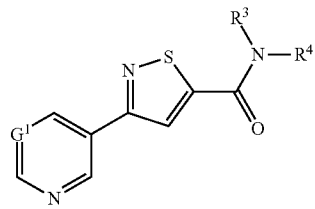
(I-21a)

in which $G^1$, $R^3$ and $R^4$ are each as defined above.

In a further preferred embodiment, the invention relates to compounds of the formula (I-23a)

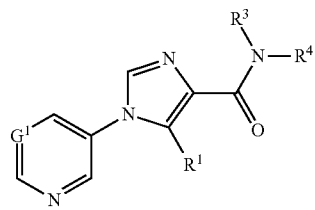
(I-23a)

in which $G^1$, $R^1$, $R^3$ and $R^4$ are each as defined above.

In a further preferred embodiment, the invention relates to compounds of the formula (I-26a)

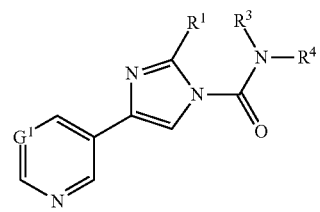
(I-26a)

in which $G^1$, $R^1$, $R^3$ and $R^4$ are each as defined above.

In a further preferred embodiment, the invention relates to compounds of the formula (I-29a)

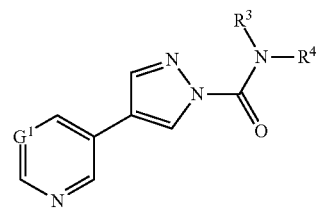
(I-29a)

in which $G^1$, $R^3$ and $R^4$ are each as defined above.

In a further preferred embodiment, the invention relates to compounds of the formula (I-35a)

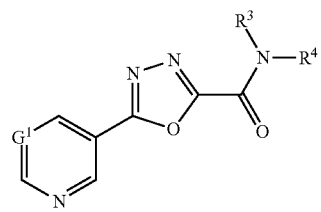
(I-35a)

in which $G^1$, $R^3$ and $R^4$ are each as defined above.

In a further preferred embodiment, the invention relates to compounds of the formula (I-38a)

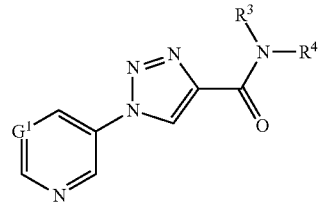
(I-38a)

in which $G^1$, $R^3$ and $R^4$ are each as defined above.

In a farther preferred embodiment, the invention relates to compounds of the formula (I-49a)

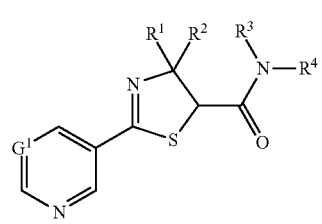
(I-49a)

in which $G^1$, $R^1$, $R^2$, $R^3$ and $R^4$ are each as defined above.

The inventive compounds can be prepared by customary methods known to those skilled in the art.

The preparation of the heterocyclic base skeletons in compounds of the formula (I) is possible by one or more synthesis variants, which are shown in reaction schemes 1 to 8.

Compounds of the formula (I) in which Q is Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48, Q-49, Q-50, Q-51, Q-52, Q-53, Q-58, Q-61, Q-62 or Q-63 are preparable, for example, according to reaction scheme 1.

preparation of amide bonds are known (cf. Bodansky et al., Peptide Synthesis $2^{nd}$ ed, Wiley & Sons, New York, 1976). For examples of the amine coupling partners described, for (I-a) see WO 2006/100591 [Q-19], WO 2007/139816 [Q-5], Bioorg. Med. Chem. Lett. 2007, 17, 363-369 [Q-4], for (I-b) see U.S. Pat. No. 4,053,608, X. Li et al., Chem. Commun. 2008, 2444-2446, for (I-c) see WO 2005/47225, T. S. Gardner et al., J. Org. Chem. 1954, 19, 753-757; (I-d) see U.S. Pat. No. 4,778,802, J. Delarge et al., Eur. J. Med. Chem. 1981, 16, 65-68, for (I-e) see WO 2004/67524, for (I-f) see U.S. Pat. No. 6,576,627, for (I-g) see Chem. Lett. 2007, 36, 1370-1371, for Reaction scheme 1

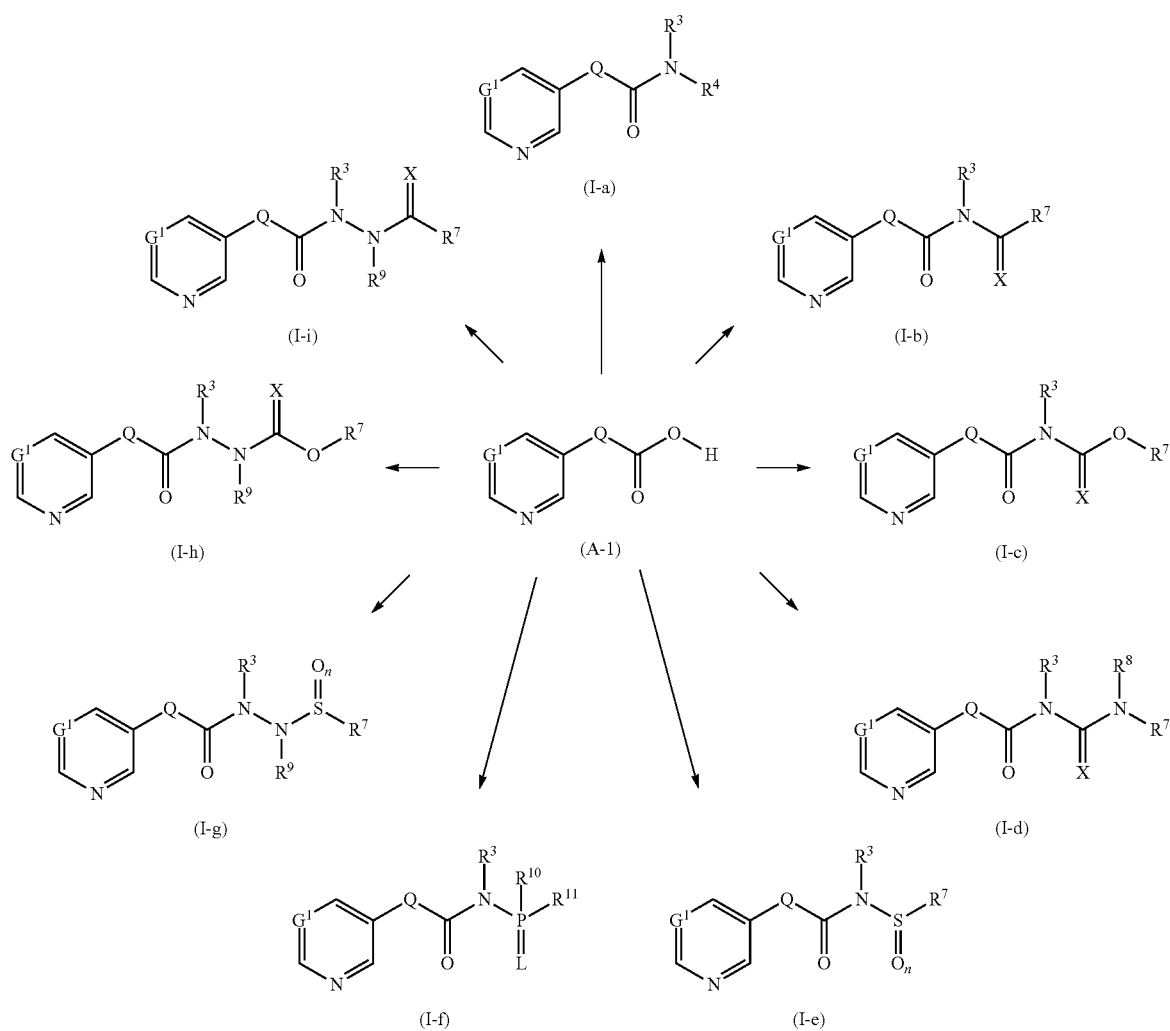

Compounds of the formula (I-a) to (I-i) can be prepared by activating the carboxylic acids of the formula (A-1) by conversion to acid chlorides, acid fluorides or mixed anhydrides, or by reaction with coupling reagents, for example BOPCl (cf., for example, Houben-Weyl, Methoden der organischen Chemie [Methods of Organic Chemistry], volume 15/2; M. Bodanszky et al., The Practice of Peptide Synthesis, Springer, N.Y., 1984; C. A. G. N. Montalbetti et al., Tetrahedron 2005, 61, 10827-10852) and then reacting them with the appropriate amines, amides, carbamates, ureas or hydrazine derivatives, optionally in the presence of a coupling reagent and of a basic reaction auxiliary. Coupling reagents suitable for (1-h) see WO 2006/45514, WO 2005/103043 and for (I-i) see WO 2005/82866, and WO 2005/97750.

2-Bromo-2,2-difluoroethanamine can be obtained by commonly known methods (cf. WO 2004/916113 A2).

Compounds of the formula (A-1) in which Q is Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48, Q-49, Q-50, Q-51, Q-52, Q-53, Q-58, Q-61, Q-62 or Q-63 are preparable, for example, according to reaction scheme 2.

Reaction scheme 2

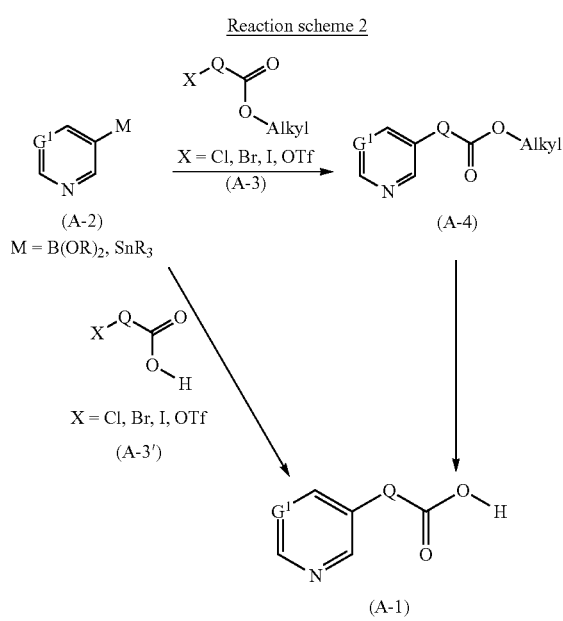

To prepare the inventive compounds, (hetero)arylboronic acids or (hetero)arylboronic esters of the formula (A-2) are first reacted with the appropriate halogenated esters of the formula (A-3) by known methods (*Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), $2^{nd}$ ed., Wiley-VCH, Weinheim, 2004) with transition metal salt catalysis to give compounds of the formula (A-4). For example, the reaction of pyridin-3-ylboronic acid with methyl 5-bromo-2-furanate [Q-1] or methyl 5-bromothiophene-2-carboxylate [Q-4] is described (cf. L. A. McAllister et al., *J. Am. Chem. Soc.* 2006, 128, 4176-4177). Analogous reactions with substituted thiophenes are described in WO 2005/61494 and Z.-K. Wan et al., *Bioorg. Med. Chem. Lett.* 2006, 16, 4941-4945. Similar coupling reactions are described for the following substituted or unsubstituted halogenated carboxylic esters of the formula (A-3) or the analogous acids of the formula (A-3'): methyl 2-iodo-4-methyl-1H-imidazole-5-carboxylate (WO 2004/50636, Q-28), benzyl 4-iodo-1-[(4-methylphenyl)sulphonyl]-1H-pyrrole-2-carboxylate (US 2004/138269, Q-8), 4-bromo-2-furancarboxylic acid (US 2005/54626, Q-3), methyl 5-bromothiophene-3-carboxylate (WO 2005/9941, Q-5), methyl 5-chloro-3-furanate [U.S. Pat. No. 6,302,047 B1, Q-2], ethyl 2-chloro-1,3-oxazole-4-carboxylate (US 2007/123504, Q-14), ethyl 2-bromo-1,4-dimethyl-1H-imidazole-5-carboxylate (WO 2008/111794, Q-28), ethyl 2-bromo-1,3-thiazole-4-carboxylate (US 2009/163486, Q-19), methyl 4-iodo-1H-pyrrole-2-carboxylate (J. A. Smith et al., *Org. Biomol. Chem.* 2006, 4, 2477-2482, Q-9) and ethyl 4-bromo-1-(1-ethoxyethyl)-1H-imidazole-2-carboxylate, ethyl 2-chloro-5-methyl-1,3-oxazole-4-carboxylate (S. Lee et al., *Bioorg. Med. Chem. Lett.* 2009, 19, 1329-1331, Q-30, Q-14).

Corresponding reactions have also been described with trialkyltin heteroaryl compounds (cf. J. Zhang et al., *Bioorg. Med. Chem. Lett.* 2000, 10, 2575-2578).

Boronic acids and boronic esters of the formula (A-2) are commonly known and are preparable by commonly known methods [pyridin-3-ylboronic acid (cf. WO 2005/66162), pyrimidin-5-ylboronic acid (cf. WO 2005/103019), (5-fluoropyridin-3-yl)boronic acid (cf. WO 2009/61875), 344,4,5,5-tetramethyl-1,3,2-dioxaborolan-2-yl)pyridine (cf. T. Ishiyama et al., *Tetrahedron* 2001, 57, 9813-9816)]. Trialkyltin heteroaryl compounds of the formula (A-2) are commonly known and preparable by commonly known methods [3-(trimethylstannyl)pyridine (cf. U.S. Pat. No. 6,544,985, WO 2003/72553). Halogenated carboxylic esters of the formula (A-3) or acids thereof are commonly known and are preparable by commonly known methods [ethyl 5-bromo-2-furanate (cf. WO 2004/33440), methyl 5-bromo-3-furanate (cf. G. Johansson et al., *J. Med. Chem.* 1997, 40, 3804-3819), methyl 5-bromothiophene-2-carboxylate (cf. WO 2005/79791), methyl 2-chloro-1,3-oxazole-5-carboxylate (cf. WO 2007/131953), ethyl 3-bromo-1,2-oxazole-5-carboxylate (cf. WO 2005/26149)].

Compounds of the formula (A-4) in which alkyl is preferably methyl or ethyl can be converted by ester cleavage of the carboxylic ester to the compound of the formula (A-1). The ester cleavage can be performed by the known methods (cf. *Greene's protective groups in organic synthesis*, $4^{th}$ ed., P. G. M. Wuts, T. W. Greene, John Wiley & Sons, Inc., Hoboken, N.J., 2007); for example, the compound of the formula (A-4) can be reacted with aqueous lithium hydroxide solution in tetrahydrofuran and subsequent acidification or with aqueous sodium hydroxide solution in alcohols and subsequent acidification to give the corresponding acid of the formula (A-1).

Compounds of the formula (A-1) in which Q is Q-1, Q-2, Q-3, Q-4, Q-5, Q-6, Q-8, Q-9, Q-10, Q-11, Q-12, Q-13, Q-14, Q-15, Q-16, Q-17, Q-18, Q-19, Q-20, Q-21, Q-22, Q-25, Q-26, Q-27, Q-28, Q-29, Q-30, Q-31, Q-32, Q-33, Q-34, Q-35, Q-36, Q-37, Q-41, Q-42, Q-43, Q-44, Q-45, Q-46, Q-47, Q-49, Q-50, Q-51, Q-52, Q-59, Q-61, Q-62 or Q-63 are preparable, for example, according to reaction scheme 3.

Reaction scheme 3

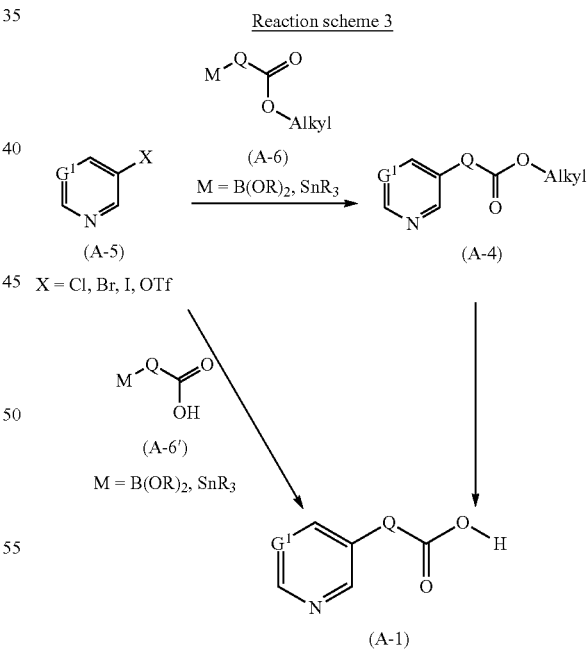

To prepare the inventive compounds, halides or triflates (A-5) are first reacted with the appropriate (hetero)arylboronic acids or (hetero)arylboronic esters of the formula (A-6) or (A-6') by known methods (see reaction scheme 2) with transition metal salt catalysis to give compounds of the formula (A-4) or (A-1). For example, the reaction of 5-(dihydroxyboryl)thiophene-2-carboxylic acid [Q-4] with 3-bromopyridine has been described (cf. WO 2004/13130). Similar coupling reactions have been described for the following substituted or unsubstituted (hetero)arylboronic acids or (hetero)arylboronic esters of the formulae (A-6) and (A-6'): tert-butyl 4-(4,4,5,5-tetramethyl-1,3,2-dioxaborolan-2-yl)-1H-pyrazole-1-carboxylate (WO 2007/75567 [Q-29]), 5-(dihydroxyboryl)-2-furancarboxylic acid (*Bioorg. Med. Chem. Lett.* 2007, 17, 5944-5951 [Q-1]) and tert-butyl 3-(4,4,5,5-tetramethyl-1,3,2-dioxaborolan-2-yl)-1H-pyrrole-1-carboxylate (*Angew. Chem.* 2008, 120, 3046-3049 [Q-10]).

Corresponding reactions have also been described with trialkyltin heteroaryl compounds (U.S. Pat. No. 6,544,985 [Q-25], US 2004/0214870 (7,381,736) [Q-17], WO 2007/107758 [Q-18], *Bioorg. Med. Chem.* 2003, 11, 281-292 [Q-1]).

The conversion of esters of the formula (A-4) to carboxylic acids of the formula (A-1) can be performed as described in reaction scheme 3.

Compounds of the formula (A-1) in which Q is Q-7, Q-23, Q-24, Q-38, Q-39, Q-40, Q-48, Q-53, Q-55, Q-56, Q-57 or Q-58 are preparable, for example, according to reaction scheme 4.

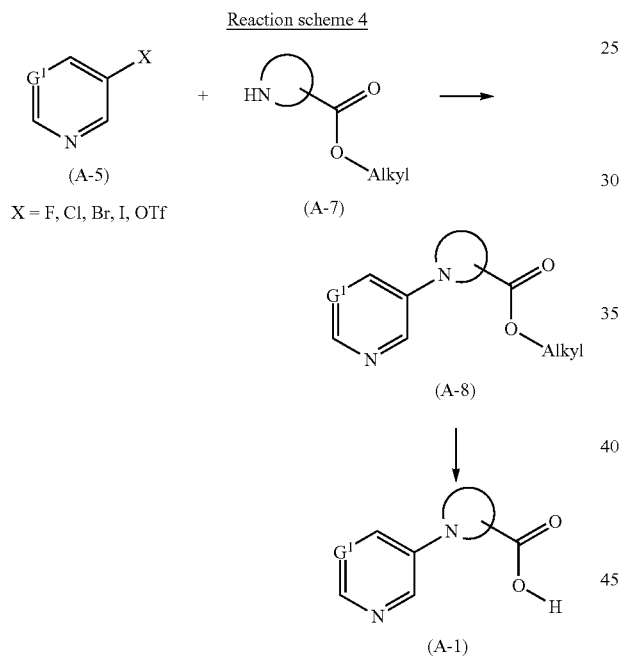

To prepare the inventive compounds, halides or triflates of the formula (A-5) are first reacted with the esters of the formula (A-7) by known methods (Mini-Reviews in *Organic Chemistry* 2008, 5, 323-330; *Molecules* 2009, 14, 5169-5178; pyrazole: *Eur. J. Org. Chem.* 2004, 4, 695-709) with transition metal salt catalysis to give compounds of the formula (A-8). For example, the reaction of methyl 1H-pyrrole-3-carboxylate [Q-7] with 4-bromoisoquinoline has been described (cf. WO 2004/7478). Similar coupling reactions have been described for the following substituted or unsubstituted heterocyclylcarboxylic esters of the formula (A-7): methyl 1H-imidazole-4-carboxylate (US 2005/0192302 [Q-23]), methyl 1H-pyrazole-3-carboxylate (WO 2007/75749 [Q-24]) and methyl 1H-1,2,4-triazole-3-carboxylate (US 2005/0267105 [Q-40]).

The conversion of esters of the formula (A-8) to carboxylic acids of the formula (A-1) can be performed as described in reaction scheme 3.

Compounds of the formula (A-1) in which Q is Q-21 or Q-34 are preparable, for example, according to reaction scheme 5,

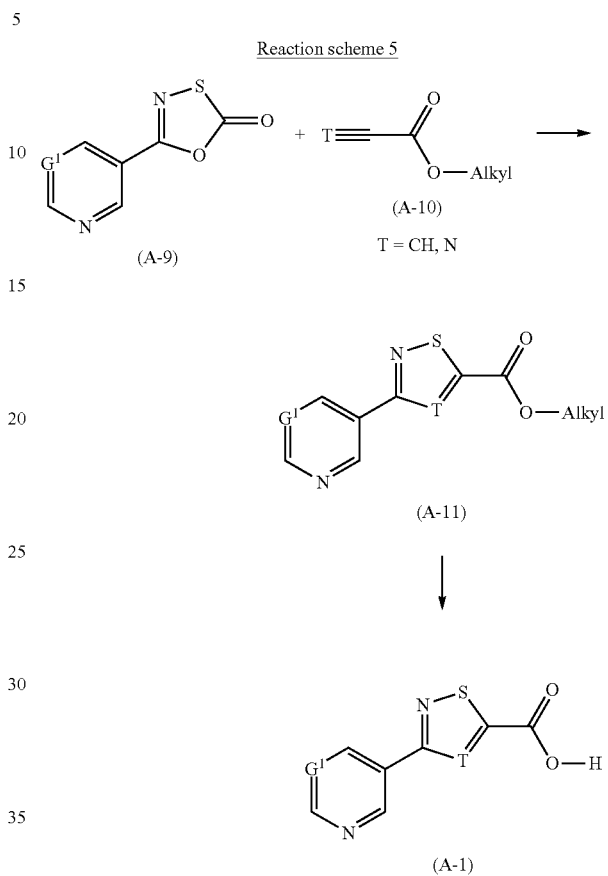

To prepare the inventive compounds, 1,3,4-oxathiazol-2-ones (A-9, for preparation see, for example: *J. Med. Chem.* 2001, 44, 1560-1563) are first reacted with the appropriate compounds of the formula (A-10) to give compounds of the formula (A-11). Reactions of this kind are described, for example, in the following publications: US 2007/0244094, U.S. Pat. No. 4,144,047, [Q-21], WO 2009/37485 and US 2005/96362 [Q-34].

The conversion of esters of the formula (A-11) to carboxylic acids of the formula (A-1) can be performed as described in reaction scheme 3.

Inventive compounds of the formula (I) in which Q is Q-10, Q-26, Q-29, Q-32, Q-41, Q-42, Q-43, Q-47 and Q-59, and the other moieties and substituents are defined in accordance with the invention, are preparable according to reaction scheme 6.

Compounds of the formula (A-1) in which Q is Q-13 can also be prepared, for example, by deprotonating the oxazole with a strong base and then carboxylating, for example with carbon dioxide (cf. Preparation Examples-Example F).

Compounds of the formula (A-4) in which Q is Q-20 can also be prepared, for example, by the reaction of thioamides with alkyl 3-halo-2-oxopropanoate (cf. *Justus Liebigs Ann. Chem.* 1959, 621, 106-119) and then reacted by the processes described in reaction scheme 3 to give compounds of the formula (A-1) (cf. Preparation Examples-Example H).

Reaction scheme 6

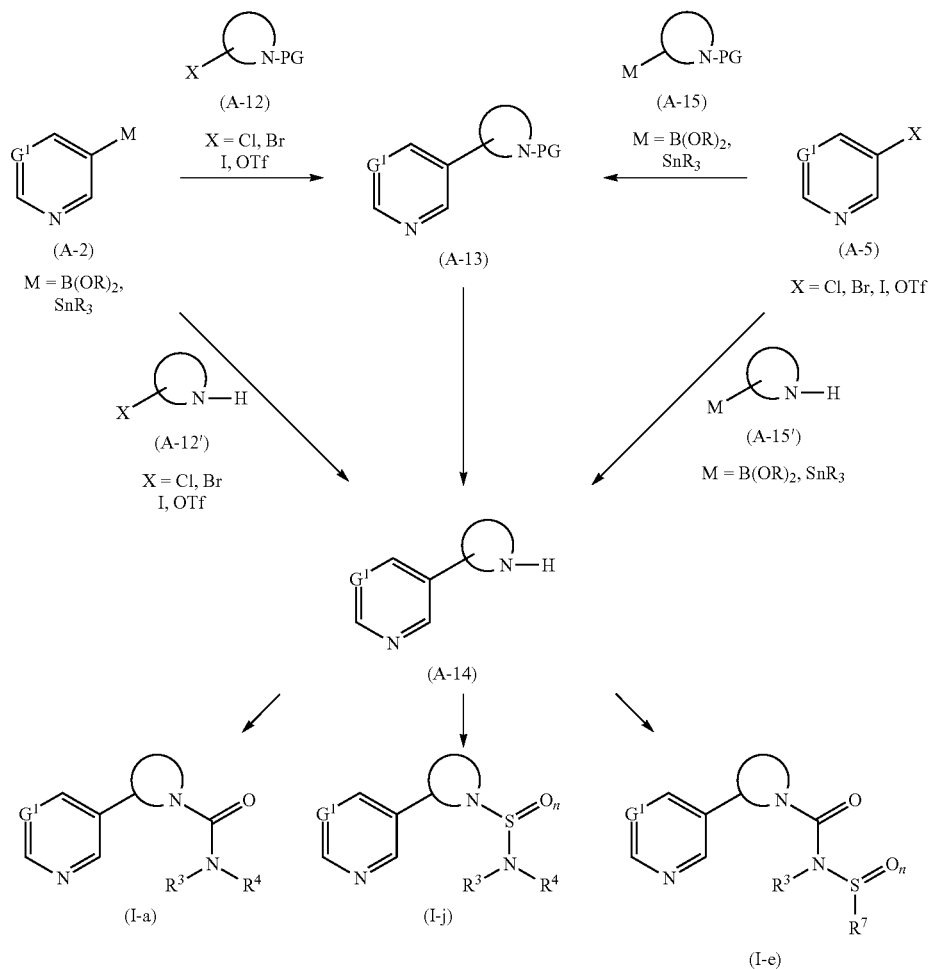

To prepare the inventive compounds of the (I-a), (I-e) and (I-j) type, analogously to the reactions shown in reaction scheme 2, (hetero)arylboronic acids or (hetero)arylboronic esters of the formula (A-2) are first reacted with the appropriate halogenated compounds (A-12, PG corresponds, for example, to trityl) or of the formula (A-12') by known methods (see above) under transition metal salt catalysis to give compounds of the formulae (A-13) and (A-14). For example, the reaction of pyridin-3-ylboronic acid with 4-bromo-1H-pyrazole [Q-29] (cf. N. Kudo et al., Angew. Chem. IE 2006, 45, 1282-1284) and the reaction with 4-bromo-1H-imidazole (cf. T. Denton et al., J. Med. Chem. 2005, 28, 224-239) have been described. Analogous reactions of the following compounds with substituted pyridinylboronic acids have been described: 2-[(benzyloxy)methyl]-5-bromo-2H-tetrazole (EP 2002/779936, Q-46), 1-[2-(benzyloxy)ethyl]-3-bromo-1H-pyrazole (U.S. Pat. No. 6,340,759, Q-32), 3-bromo-1-(triisopropylsilyl)-1H-pyrrole (J. Am. Chem. Soc. 2007, 129, 3358-3366, Q-7). The reaction of 3-bromo-1H-1,2,4-triazol-1-yl compounds with pyridinylboronic acids is known (cf. WO 2009/32861, Q-43).

Alternatively, compounds of the formulae (A-13) and (A-14), analogously to the reactions shown in reaction scheme 3, can be prepared by transition metal salt-catalysed reaction of halides or triflates of the formula (A-5) with the appropriate (hetero)arylboronic acids or (hetero)arylboronic esters of the formulae (A-15) or (A-15'). For example, the reaction of 3-bromopyridine with [1-(triisopropylsilyl)-1H-pyrrol-3-yl]boronic acid [Q-10] has been described (cf. A. Alvarez et al., J. Org. Chem. 1992, 57, 1653-1656). Similar reactions have been described, for example, for the following compounds: (1-trityl-1H-pyrazol-4-yl)boronic acid (cf. EP 2002/722791, Q-289), 4-(tributylstannyl)-1-trityl-1H-imidazole (cf. WO 2005/35521, Q-26), 1H-pyrazol-3-ylboronic acid (cf. WO 2007/71455, Q-32), 2-[(benzyloxy)methyl]-5-(tributylstannyl)-2H-tetrazole (cf. WO 2007/88999, Q-47).

The conversion of the compound of the formula (A-13) to the unprotected compound of the formula (A-14) can be performed by commonly known methods (cf. Greene's protective groups in organic synthesis, 4$^{th}$ ed., P. G. M. Wuts, T. W. Greene, John Wiley & Sons, Inc., Hoboken, N.J., 2007); for example, (A-X, PG=Trityl) can be reacted with hydrochloric acid in ethanol to give the corresponding unprotected compound of the formula (A-14) (cf. M. T. Burger et al., J. Med. Chem. 2006, 49, 1730-1743).

To prepare the inventive compounds of the (I-a), (I-e) and (I-j) type, the corresponding compounds of the formula (A-14) are reacted with the appropriate acylating reagents, optionally in the presence of an activator and of a basic reaction auxiliary. Literature examples of the amine coupling partners described are listed below: (I-a) cf. U.S. Pat. No. 5,506,191 [Q-32], US 2009/0239810 [Q-29], R. Milcent et al., *J. Het. Chem.* 1987, 24, 1233-1234 [Q-47], A. Castro et al., *Med. Chem. Res.* 2002, 11, 219-237 [26]; (I-j) cf. WO 2008/129054 [Q-32], EP 2004/747746 [Q-26], EP 2000/929908 [Q-43]; (I-e) cf. N. L. Nam et al., *Chem. Het. Comp.* 1994, 30, 40-43 [Q-32].

Compounds of the formula (I-a) in which Q is Q-41 or Q-47, and the other moieties and substituents are defined in accordance with the invention, are preparable, for example, according to reaction scheme 7.

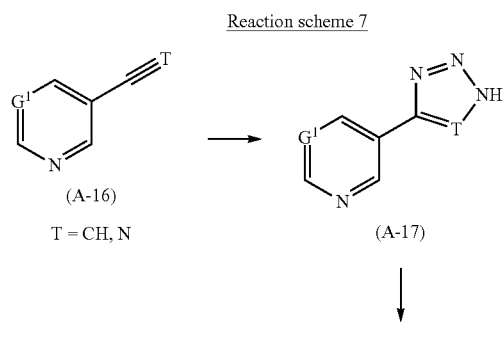

To prepare the inventive compounds, cyanides or acetylides of the formula (A-16) are first reacted with metal azides, for example sodium azide, or other sources of nitrogen-hydrogen acid, for example trimethylsilyl azide, under transition metal salt catalysis (for example copper catalysis) to give compounds of the formula (A-17). For example, the reaction of nicotinonitrile with sodium azide and ammonium chloride in DMF (cf. WO 2005/66162) has been described. The reaction of 3-ethynylpyridine with trimethylsilyl cyanide (cf. U.S. Pat. No. 4,866,077) has also been described. The acylation of compounds of the structure (A-17), which leads to compounds of the I-a type, is described, for example, in *J. Het. Chem.* 1987, 24, 1233-1234.

Compounds of the formula (I-j) in which Q is Q-1, Q-2, Q-3, Q-4, Q-5, Q-6, Q-8, Q-9, Q-10, Q-11, Q-12, Q-13, Q-14, Q-15, Q-16, Q-17, Q-18, Q-19, Q-20, Q-21, Q-22, Q-25, Q-26, Q-27, Q-28, Q-29, Q-30, Q-31, Q-32, Q-33, Q-34, Q-35, Q-36, Q-37, Q-41, Q-42, Q-43, Q-44, Q-45, Q-46, Q-47, Q-49, Q-50, Q-51, Q-52, Q-59, Q-61, Q-62 or Q-63, and the other moieties and substituents are defined in accordance with the invention, are preparable, for example, according to reaction scheme 8.

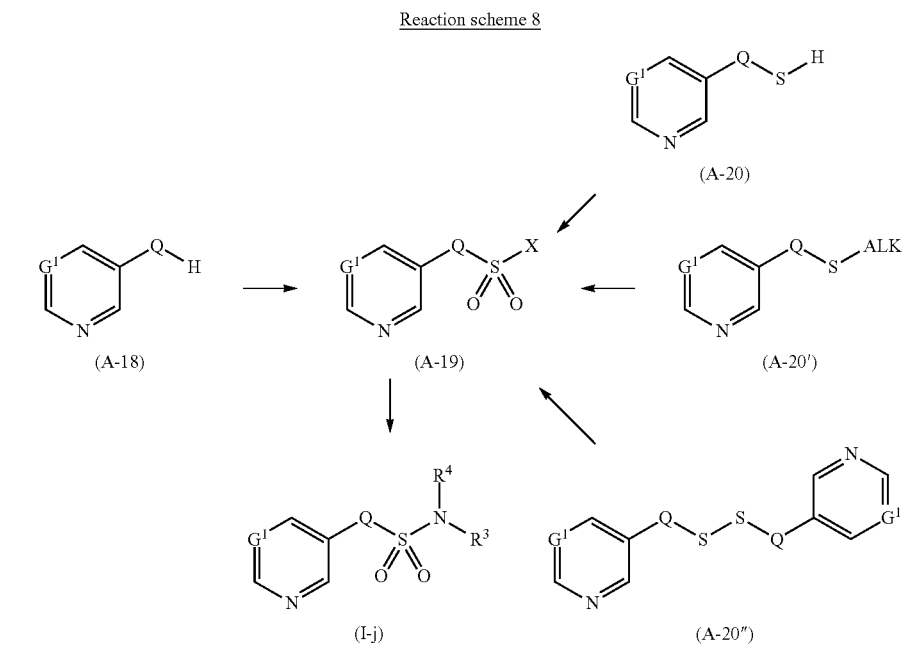

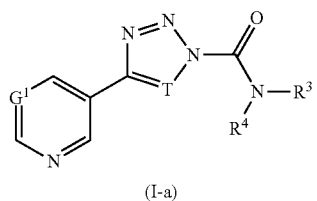

To prepare the inventive compounds, the compounds of the formula (A-18) are first deprotonated, reacted with a sulphur source, for example sulphur dioxide, and then with an oxidizing agent (for example sulphuryl dichloride) to give the corresponding chlorosulphonyl compounds of the formula (A-19) where X=Cl. For example, the conversion of 3-(2-thienyl)pyridine to 5-(pyridin-3-yl)thiophene-2-sulphonyl chloride has been described (U.S. Pat. No. 6,034,093 [Q-4]). Alternatively, the oxidation of sulphanyl compounds (of the formula A-20), alkylsulphanediyl compounds (of the formula A-20') or disulphane compounds (of the formula A-20") with appropriate oxidizing agents, for example chlorine, in appropriate solvents, for example water, to give the chlorosulphonyl compounds of the formula (A-19) is known (*J. Het. Chem.* 1972, 9, 695-697 [Q-16], Indian J. Chem. 1994, 33, 350-353 [Q-34]).

For example, the preparation of sulphanyl compounds of the formula (A-20) has been described: U.S. Pat. No. 4,894,380 [Q-35], U.S. Pat. No. 5,750,686 [Q-20], U.S. Pat. No. 4,866,077 [Q-44, Q-45], *Chem. Pharm. Bull.* 1984, 32, 2536-2543 [Q-31]. For example, the preparation of alkylsulphanediyl compounds of the formula (A-20') has been described: U.S. Pat. No. 6,506,747 [Q-25], *Arzneimittel Forschung* 1994, 44, 863-866 [Q-16], *Bioorg. Med. Chem. Lett.* 2004, 14, 4037-4044 [Q-6]. For example, the preparation of disulphane compounds of the formula (A-20'') has been described: *J. Org. Chem.* 1966, 31, 3580-3582 [Q-11].

Compounds of the (I-j) type can be prepared in analogy to reaction scheme 1 from the chlorosulphonyl compounds of the formula (A-19) with the appropriate reaction partners. For example, 5-(pyridin-3-yl)thiophene-2-sulphonyl chloride has been reacted in pyridine with a primary amine (cf. *J. Med. Chem.* 1999, 42, 3572-3587).

The inventive active ingredients, in combination with good plant tolerance, favorable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttalatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostongulus* spp., *Trichuris trichuria, Wuchereria bancrofti.*

It is also possible to control protozoa, such as Eimeria.

From the order of the heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotas* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chroma-*

*phis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus* and *Porcellio scaber.*

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia* kuehniella, *Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp, *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

The inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms). They can also be used as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances.

These formulations are produced in a known manner, for example by mixing the active ingredients with extenders, i.e. liquid solvents, and/or solid carriers, optionally with use of surfactants, i.e. emulsifiers and/or dispersants, and/or foam formers. The formulations are produced either in suitable production plants or else before or during application.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Useful solid carriers include:
for example ammonium salts and natural rock flours, such as kaolins, aluminas, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Further suitable oligomers or polymers are, for example, those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

In the formulations it is possible to use tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as low-temperature stabilizers, preservatives, antioxidants, light stabilizers or other agents which improve chemical and/or physical stability.

The formulations contain generally between 0.01 and 98% by weight of active ingredient, preferably between 0.5 and 90%.

The inventive active ingredients may be used as such or in formulations thereof, including in a mixture with one or more suitable fungicides, bactericides, acaricides, nematicides, insecticides, microbicides, fertilizers, attractants, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. Furthermore, active ingredient combinations of this kind can improve plant growth, increase tolerance to high or low temperatures, to drought or to increased levels of water and/or soil salinity, improve flowering performance, facilitate harvesting and increase yields, accelerate ripening, increase the quality and/or nutritional value of the harvested products, prolong storage life and/or improve the processability of the harvested products. By combining the inventive active ingredients with mixing partners, synergistic effects are obtained, i.e. the efficacy of the particular mixture is greater than expected on the basis of the efficacies of the individual components. Generally, the combinations can be used either as seed treatments or in premixes, tankmixes or readymixes.

Any additional active ingredient can be mixed with the inventive active ingredients within a wide range, preferably in a ratio of 100:1 to 1:100, more preferably of 5:1 to 1:5.

Particularly favourable mixing partners are, for example, the following:

Insecticides/Acaricides/Nematicides:

The active ingredients identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, for example pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, eto-fenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmetlyin, RU 15525, silafluofen, tefluthrin, tetramethrin [(1R)-isomers], tralomethrin, transtiuthrin and ZXI 8901; or DDT; or methoxychlor.

(4) Nicotinergic acetylcholine receptor agonists, for example neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), for example spinosyns, for example spinetoram and spinosad.

(6) Chloride channel activators, for example
avermectins/milbemycins, for example abamectin, emamectin benzoate, lepimectin and milbemectin.
(7) Juvenile hormone analogues, for example hydroprene, kinoprene, methoprene; or fenoxycarb; pyriproxyfen.
(8) Active ingredients with unknown or nonspecific mechanisms of action, for example
fumigants, for example methyl bromide and other alkyl halides; or
chloropicrin; sulphuryl fluoride; borax; tartar emetic.
(9) Selective antifeedants, for example pymetrozine; or flonicamid.
(10) mite growth inhibitors, for example clofentezine, diflovidazin, hexythiazox, etoxazole.
(11) microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors, for example diafenthiuron; or
organotin compounds, for example azocyclotin, cyhexatin, fenbutatin oxide; or
propargite; tetradifon.
(13) Oxidative phosphorylation decouplers acting by interrupting the H proton gradient, for example chlorfenapyr and DNOC.
(14) Nicotinergic acetylcholine receptor antagonists, for example bensultap, cartap (hydrochloride), thiocylam, and thiosultap (sodium).
(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, for example buprofezin.
(17) Moulting disruptors, for example cyromazine.
(18) Ecdysone agonists/disruptors, for example
diacylhydrazines, for example chromafenozide, halofenozide, methoxyfenozide and tebufenozide.
(19) Octopaminergic agonists, for example amitraz.
(20) Complex-III electron transport inhibitors, for example hydramethylnone; acequinocyl; fluacrypyrim.
(21) Complex-I electron transport inhibitors, for example from the group of the METI acaricides, for example fenazaquin, fenpyroximate, pyrimidifen, pyridaben, tebufenpyrad, tolfenpyrad; or
rotenone (Derris).
(22) Voltage-dependent sodium channel blockers, for example indoxacarb; metaflumizone.
(23) Inhibitors of acetyl-CoA carboxylase, for example tetronic acid derivatives, for example spirodiclofen and spiromesifen; or tetramic acid derivatives, for example spirotetramat.
(24) Complex-IV electron transport inhibitors, for example phosphines, for example aluminium phosphide, calcium phosphide, phosphine, zinc phosphide; or cyanide.
(25) Complex-II electron transport inhibitors, for example cyenopyrafen.
(28) Ryanodine receptor effectors, for example diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2001043677).

Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (I-1582, BioNeem, Votivo) and the following compounds:
4-{[(6-bromopyrid-3-yl)methyl](2-fluoroethyl)amino}furan-2(5H)-one (known from WO 2007/115644),
4-{[(6-fluoropyrid-3-yl)methyl](2,2-difluoroethyl)amino}furan-2(5H)-one (known from WO 2007/115644),
4-{[(2-chloro-1,3-thiazol-5-yl)methyl](2-fluoroethyl)amino}furan-2(5H)-one (known from WO 2007/115644),
4-{[(6-chloropyrid-3-yl)methyl](2-fluoroethyl)amino}furan-2(5H)-one (known from WO 2007/115644),
4-{[(6-chloropyrid-3-yl)methyl](2,2-difluoroethyl)amino}furan-2(5H)-one (known from WO 2007/115644),
4-{[(6-chloro-5-fluoropyrid-3-yl)methyl](methyl)amino}furan-2(5H)-one (known from WO 2007/115643),
4-{[(5,6-dichloropyrid-3-yl)methyl] m(2-fluoroethyl)amino}furan-2(5H)-one (known from WO 2007/115646),
4-{[(6-chloro-5-fluoropyrid-3-yl)methyl](cyclopropyl)amino}furan-2(5H)-one (known from WO 2007/115643),
4-{[(6-chloropyrid-3-yl)methyl](cyclopropyl)amino}furan-2(5H)-one (known from EP-A-0 539 588),
4-{[(6-chloropyrid-3-yl)methyl](methyl)amino}furan-2(5H)-one (known from EP-A-0 539 588), {[1-(6-chloropyridin-3-yl)ethyl](methyl)oxido-λ$^4$-sulphanylidene}cyanamide (known from WO2007/149134) and its diastereomers {[(1R)-1-(6-chloropyridin-3-yl)ethyl](methyl)oxido-λ$^4$-sulphanylidene}cyanamide (A) and {[(1S)-1-(6-chloropyridin-3-yl)ethyl]methyl)oxido-λ$^4$-sulphanylidene}cyanamide (B) (likewise known from WO2007/149134) and sulfoxaflor (likewise known from WO2007/149134) and its diastereomers [(R)-methyl (oxido){(1R)-1-[6-(trifluoromethyl)pyridin-3-yl]ethyl}-λ$^4$-sulphanylidene]cyanamide (A1) and [(S)-methyl (oxido){(1S)-1-[6-(trifluoromethyl)pyridin-3-yl]ethyl}-λ$^4$-sulphanylidene]-cyanamide (A2), designated as diastereomer group A (known from WO 2010/074747, WO 2010/074751), [(R)-methyl(oxido) {(1S)-1-[6-(trifluoromethyl)pyridin-3-yl]ethyl}-λ$^4$-sulphanylidene]cyanamide (B1) and [(S)-methyl(oxido){(1R)-1-[6-(trifluoromethyl)pyridin-3-yl]ethyl}-λ$^4$-sulphanylidene]cyanamide (B2), designated as diastereomer group B (likewise known from WO 2010/074747, WO 2010/074751), and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911),
1-[2-fluoro-4-methyl-5-[(2,2,2-trifluoroethyl)sulphinyl]phenyl]-3-(trifluoromethyl)-1H-1,2,4-triazole-5-amine (know from WO 2006/043635),
[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2006/129714),
2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288),
2-cyano-3-(difluoromethoxy)-N-ethylbenzenesulphonamide (known from WO2005/035486),
4-(difluoromethoxy)-N-ethyl-N-methyl-1,2-benzothiazole-3-amine 1,1-dioxide (known from WO2007/057407) and
N-[1-(2,3-dimethylphenyl)-2-(3,5-dimethylphenyl)ethyl]-4,5-dihydro-1,3-thiazole-2-amine (known from WO2008/104503).

In a preferred embodiment of the invention, a penetrant is additionally added to the crop protection compositions to enhance the action. Useful penetrants also include, for example, substances which promote the availability of the compounds of the formula (I) in the spray coating. These include, for example, mineral and vegetable oils. Useful oils include all mineral or vegetable oils—modified or otherwise—which are typically usable in agrochemical compositions. Examples include sunflower oil, rapeseed oil, olive oil, castor oil, colza oil, cornseed oil, cottonseed oil and soybean oil or the esters of the oils mentioned. Preference is given to rapeseed oil, sunflower oil and their methyl or ethyl esters, especially rapeseed oil methyl ester.

The concentration of penetrant in the inventive compositions can be varied within a wide range. In the case of a formulated crop protection composition, it is generally 1 to 95% by weight, preferably 1 to 55% by weight, more preferably 15-40% by weight. In the ready-to-use compositions (spray liquors), the concentrations are generally between 0.1 and 10 g/l, preferably between 0.5 and 5 g/l.

When used as insecticides, the inventive active ingredients may also be present in their commercially available formulations and in the use forms, prepared from these formulations, as a mixture with synergists. Synergists are compounds which enhance the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations may vary within wide limits. The active ingredient concentration of the use forms may be from 0.00000001 to 95% by weight of active ingredient, preferably between 0.00001 and 1% by weight.

The compounds are applied in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Examples include the important crop plants, such as cereals (wheat, rice), maize, soya, potatoes, sugarbeet, tomatoes, peas and other vegetable species, cotton, tobacco, oilseed rape and also fruit plants (the fruits produced being apples, pears, citrus fruits and grapes). Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. The plant parts also include harvested material and vegetative and generative propagation material, for example cuttings, tubers, rhizomes, slips and seeds.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a farther preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are understood to mean plants having new properties ("traits") and which have been obtained by conventional breeding, by mutagenesis or by recombinant DNA techniques. They can be cultivars, biotypes or genotypes.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processibility of the harvested products, which exceed the effects normally to be expected.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, increased flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF, and also combinations thereof) (referred to hereinafter as "Bt plants"). Traits that are also particularly emphasized are the improved defence of the plants against fungi, bacteria and viruses by systemic acquired resistance (SAR), systemin, phytoalexins, elicitors and also resistance genes and correspondingly expressed proteins and toxins. Traits that are additionally particularly emphasised are the increased tolerance of the plants to certain active herbicidal ingredients, for example imidazolinones, sulphonylureas, glyphosate or phosphinotricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) also include the varieties sold under the Clearfield® name (for example maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis, Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophoras* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the inventive active ingredients.

The inventive active ingredients are used in the veterinary sector and in animal husbandry in a known manner, by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

It has also been found that the inventive compounds have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon*

*aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina*.

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional mixing partners, reference is made to the insecticides and fungicides mentioned above.

At the same time, the inventive compositions can be employed for protection of objects which come into contact with saltwater or brackish water, especially hulls, screens, nets, buildings, moorings and signaling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:

From the order of the Scorpionidea, for example, *Buthus occitanus*.

From the order of the Acarina, for example, *Argas persicus, Argas ret exus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae. Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola* bisselliella.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

PREPARATION EXAMPLES

Example A 4-(Pyridin-3-yl)-N-(2,2,2-trifluoroethyl)-1H-imidazole-1-carboxamide

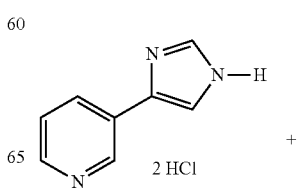

-continued

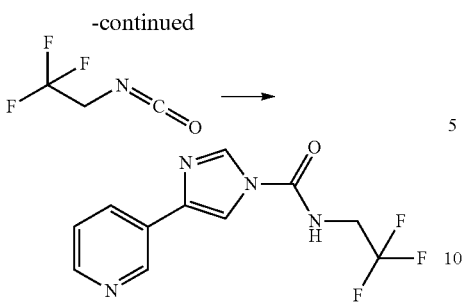

To 500 mg (2.29 mmol) of 3-(1H-imidazol-4-yl)pyridine dihydrochloride in 5 ml of dichloromethane was added dropwise, under argon, 0.96 ml (6.87 mmol) of triethylamine. The reaction mixture was stirred at room temperature for 30 minutes and then 287 mg (2.29 mmol) of 1,1,1-trifluoro-2-isocyanatoethane were added dropwise. The reaction mixture was stirred at room temperature overnight and then the solvent was removed on a rotary evaporator. Dichloromethane and water were added to the residue, and the solid obtained was filtered off with suction.

Yield: 500 mg (81% of theory); HPLC-MS: logP (HCOOH)=0.65; mass (m/z): 271.1 (M+H)$^+$;

$^1$H NMR (d$_6$-DMSO): 4.14-4.20 (m, 1H), 7.44-7.46 (m, 1H), 8.17-8.19 (m, 1H), 8.36 (d, 1H), 8.47 (d, 1H), 8.49-8.50 (m, 1H), 9.05 (d, 1H), 9.34-9.37 ppm (m, 1H).

Example B

N,N-Dimethyl-3-(pyridin-3-yl)-1,2-oxazole-5-carboxamide

Stage 1: 3-(Pyridin-3-yl)-1,2-oxazole-5-carboxylic acid

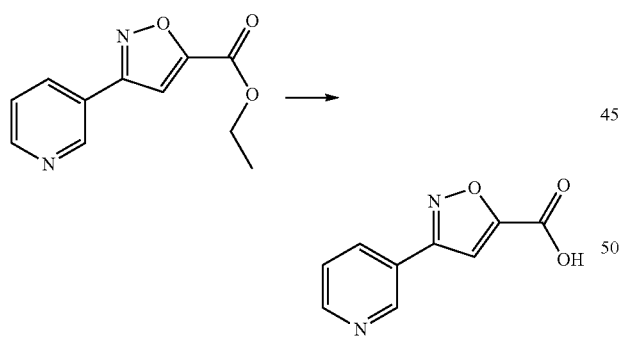

300 mg (1.38 mmol) of ethyl 3-(pyridin-3-yl)-1,2-oxazole-5-carboxylate (for preparation see *Chem. Heterocyclic Comp.* 2000, 36, 1226-1231) were dissolved in 20 ml of dioxane. While cooling with ice, 7 ml of water and 0.35 ml of 45% aqueous sodium hydroxide solution were added to the solution. The mixture was stirred at room temperature for two hours, then the dioxane was removed on a rotary evaporator under reduced pressure. Ice-water was added to the residue, and it was acidified with concentrated hydrochloric acid. The solution was stirred at room temperature overnight, and the precipitated solid was filtered off with suction and dried.

Yield: 90 mg (34% of theory)

$^1$H NMR (d$_6$-DMSO): 7.54-7.57 (m, 1H), 7.78 (s, 1H), 8.29-8.32 (m, 1H), 8.70-8.72 (m, 1H), 9.11-9.12 ppm (m, 1H).

Stage 2: 3-(Pyridin-3-yl)-1,2-oxazole-5-carbonyl chloride

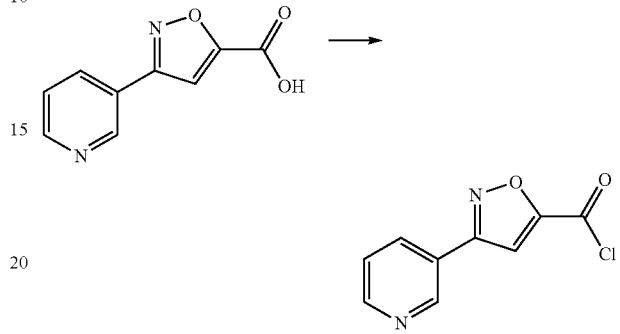

600 mg (3.16 mmol) of 3-(pyridin-3-yl)-1,2-oxazole-5-carboxylic acid were initially charged in dichloromethane, and three drops of DMF were added. 1.16 g (9.15 mmol) of oxalyl chloride were added dropwise under argon (vigorous evolution of gas). The reaction solution was stirred at room temperature and then the solvent was removed on a rotary evaporator. 30 ml of toluene were added to the residue. After the toluene had been removed on a rotary evaporator, the residue was converted further directly.

Stage 3: N,N-Dimethyl-3-(pyridin-3-yl)-1,2-oxazole-5-carboxamide

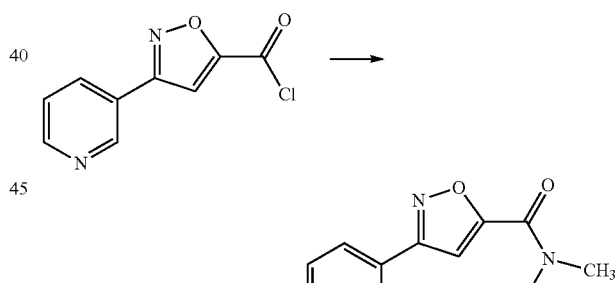

To 143 mg (3.16 mmol) of dimethylamine in 30 ml of dioxane were added dropwise 1.23 g (9.49 mmol) of N,N-diisopropylethylamine. 660 mg (3.16 mmol) of 3-(pyridin-3-yl)-1,2-oxazole-5-carbonyl chloride were slurried in 30 ml of dioxane and added dropwise at room temperature. The reaction mixture was stirred at room temperature overnight. The solvent was removed on a rotary evaporator and the residue was stirred with diethyl ether. The solid was filtered off with suction and the mother liquor was washed with water. The organic phase was dried with magnesium sulphate and then the solvent was removed under reduced pressure on a rotary evaporator.

Yield: 230 mg (33% of theory); HPLC-MS: logP (HCOOH)=0.78; mass (m/z): 218.1 (M+H)$^+$;

$^1$H NMR (d$_6$-DMSO): 3.06 (s, 6H), 7.53-7.57 (m, 2H), 8.28-8.31 (m, 1H), 8.70-8.72 (m, 1H), 9.10-9.11 ppm (m, 1H).

Example C

4-Methyl-2-(pyridin-3-yl)-N-(2,2,2-trifluoroethyl)-1,3-oxazole-5-carboxamide

Stage 1: 4-Methyl-2-(pyridin-3-yl)-1,3-oxazole-5-carboxylic acid

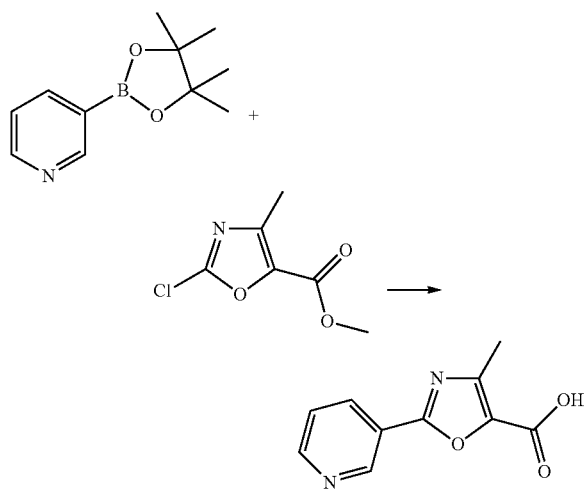

1.25 g (6.09 mmol) of 3-(4,4,5,5-tetramethyl-1,3,2-dioxaborolan-2-yl)pyridine, 0.86 g (4.87 mmol) of the 2-chlorooxazole-5-carboxylic ester and 0.28 g (0.24 mmol) of tetrakis (triphenylphosphine)palladium(0) were initially charged under argon in a mixture of 100 ml of toluene, 25 ml of ethanol and 25 ml of water, and heated under reflux for 12 hours. For workup, the aqueous phase was acidified with hydrochloric acid, and the precipitate was filtered off with suction and purified by means of chromatography on silica gel (eluent: dichloromethane/methanol).

Yield: 178 mg (18% of theory); HPLC-MS: logP=0.56; mass (m/z): 205.1 (M+H)$^+$;

$^1$H NMR (400 MHz, d$_6$-DMSO): 2.45 (s, 3H), 7.55 (m, 1H), 8.28 (m, 1H), 8.69 (m, 1H), 9.13 ppm (m, 1H).

Stage 2: 4-Methyl-2-(pyridin-3-yl)-N-(2,2,2-trifluoroethyl)-1,3-oxazole-5-carboxamide

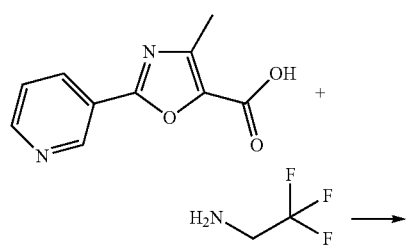

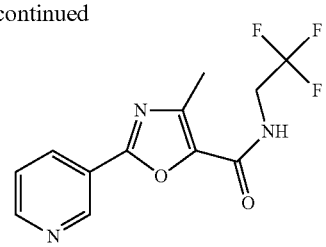

160 mg (0.78 mmol) of the oxazolecarboxylic acid and 1.32 g (10.2 mmol) of N,N-diisopropylamine were initially charged in 5 ml of acetonitrile. First 240 mg (0.94 mmol) of bis(2-oxo-3-oxazolidinyl)phosphinyl chloride (BOP—Cl) and, after 20 minutes, 233 mg (2.35 mmol) of trifluoroethylamine were added, then the mixture was stirred at room temperature for 16 hours. For workup, the mixture was substantially concentrated under reduced pressure, the residue was stirred with phosphate buffer solution (pH 7), and the crystals were filtered off with suction and purified by means of chromatography on silica gel (eluent: dichloromethane/methanol).

Yield: 27.0 mg (12% of theory); HPLC-MS: logP (HCOOH)=1.46; mass (m/z): 286.1 (M+H)$^+$;

1H NMR (400 MHz, d$_6$-DMSO): 3.32 (s, 3H), 4.10 (m, 2H), 7.63 (m, 1H), 8.50 (m, 1H), 8.78 (m, 1H), 9.22 (m, 1H), 9.35 ppm (m, 1H).

Example D

3-Methyl-5-(pyridin-3-yl)-N-(2,2,2-trifluoroethyl)thiophene-2-carboxamide

Stage 1: 3-Methyl-5-(pyridin-3-yl)thiophene-2-carboxylic acid

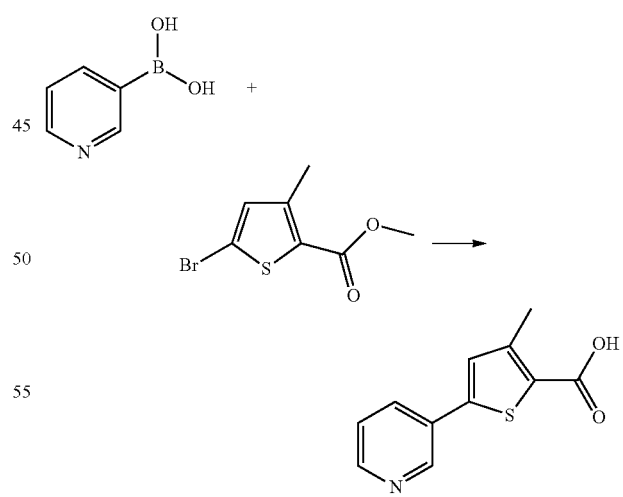

443 mg (3.60 mmol) of pyridyl-3-boronic acid, 705 mg (3.00 mmol) of the 5-bromo-3-methylthiophene-2-carboxylic ester and 208 mg (0.18 mmol) of tetrakis (triphenylphosphine)palladium(0) were initially charged under argon in a mixture of 15 ml of dimethoxyethane and 14 ml of 20% sodium carbonate solution, and the mixture was heated to 80° C. for four hours. For workup, the aqueous phase was acidified with hydrochloric acid, and the precipitate was filtered off with suction and purified by means of chromatography on silica gel (eluent: dichloromethane/methanol).

Yield: 73 mg (11% of theory); HPLC-MS: logP (HCOOH)=1.96; mass (m/z): 220.0 (M+H)$^+$;

1H NMR (400 MHz, d$_6$-DMSO): 2.50 (s, 3H), 7.45 (m, 1H), 7.50 (m, 1H), 8.05 (m, 1H), 8.55 (m, 1H), 8.90 ppm (m, 1H).

Stage 2: 3-Methyl-5-(pyridin-3-yl)-N-(2,2,2-trifluoroethyl)thiophene-2-carboxamide

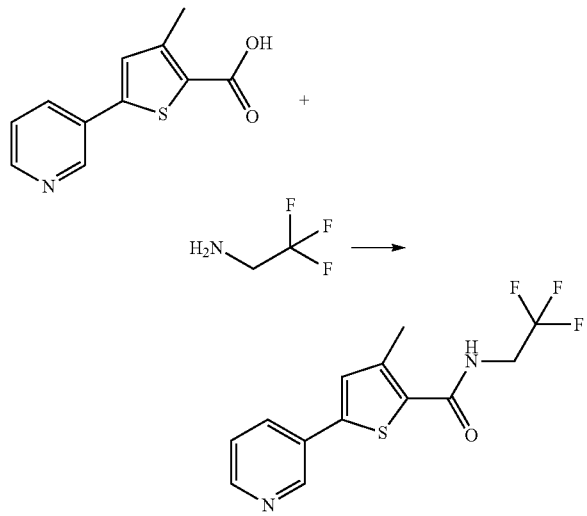

40 mg (0.18 mmol) of the thiophenecarboxylic acid and 71.0 mg (0.54 mmol) of N,N-diisopropylamine are initially charged in 10 ml of acetonitrile. 56.0 mg (0.21 mmol) of bis(2-oxo-3-oxazolidinyl)phosphinyl chloride (BOP—Cl) and, after 20 minutes, 22 mg (0.21 mmol) of trifluoroethylamine were added, and the mixture was stirred at room temperature for 16 hours. For workup, the mixture was concentrated under reduced pressure, the residue was stirred with phosphate buffer solution (pH 7), and the crystals were filtered off with suction and purified by means of chromatography on RP-18 silica gel (eluent: acetonitrile/water).

Yield: 19.0 mg (32% of theory); HPLC-MS: logP (HCOOH)=1.62; mass (m/z): 301.1 (M+H)$^+$;

1H NMR (400 MHz, d$_6$-DMSO): 2.42 (s, 3H), 4.05 (m, 2H), 7.45 (m, 2H), 8.05 (m, 1H), 8.48 (m, 1H), 8.53 (m, 1H), 8.88 ppm (m, 1H).

Example E 5-(Pyridin-3-yl)-N-(2,2,2-trifluoroethyl)furan-3-carboxamide

Stage 1: 5-(Pyridin-3-yl)furan-3-carboxylic acid

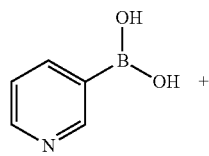

-continued 31 mg (0.17 mmol) of palladium(II) chloride and 250 mg (0.95 mmol) of triphenylphosphine were stirred with 0.5 g of tetrabutylammonium chloride in 50 ml of DMF under argon at 95° C. for 5 min, then a solution in DMF of 6.20 g (50.4 mmol) of pyridine-3-boronic acid (obtained according to *Tetrahedron Lett.* 2002, 4285 or *J. Org. Chem.* 2002, 5394) and 8.20 g (42.9 mmol) of 5-bromo-furan-3-carboxylic acid (contaminated, obtained according to *Bull. Chem. Soc. France* 1971, 990) and 16.0 g (114 mmol) of potassium carbonate as a solution in 30 ml of water were added, and the mixture was stirred under argon at 95° C. for 16 hours. Aqueous citric acid was added, the mixture was concentrated and dissolved in dilute sodium hydroxide solution, aqueous sodium chloride, n-butanol, sodium chloride was added to saturation, the mixture was extracted three times with n-butanol and the combined organic phases were concentrated. 400 ml of methanol were added, the mixture was stirred at 40° C., filtered and concentrated until it turned cloudy, the precipitate was filtered off with suction and the procedure was repeated with the filtrate. The combined filtercakes were dried on a rotary evaporator and purified by chromatography on silica gel (eluent: acetone/30% MTBE→acetone/20% methanol).

Yield 1.68 g (15% of theory); HPLC-MS: logP (HCOOH)=0.07; mass (m/z): 190.1 (M+H)$^+$;

$^1$H NMR (d$_6$-DMSO): 7.30 (s, 1H), 7.45 (m, 1H), 8.10 (d, 1H), 8.30 (s, 1H), 8.50 (m, 1H), 8.95 ppm (s, 1H).

Stage 2: 5-(Pyridin-3-yl)-N-(2,2,2-trifluoroethyl)furan-3-carboxamide 245 mg (1.30 mmol) of 5-(pyridin-3-yl)furan-3-carboxylic acid were dissolved in acetonitrile with 3.00 ml (17 mmol) of N,N-diisopropylethylamine, and 0.52 g (2 mmol) of BOP—Cl were added.

After 20 minutes, 0.30 ml (3.90 mmol) of 2,2,2-trifluoroethylamine was added, the mixture was stirred for 16 hours, then concentrated, ethyl acetate, aqueous sodium chloride and phosphate buffer pH 7 were added, and the mixture was extracted twice with ethyl acetate. The combined organic phases were dried with $Na_2SO_4$ and concentrated. The residue was purified by chromatography on silica gel (eluent: cyclohexane/acetone).

Yield: 30.0 mg (7% of theory); HPLC-MS: logP (HCOOH)=1.13; mass (m/z): 271.0 (M+H)$^+$;

$^1$H NMR (CD$_3$CN): 4.05 (m, 2H), 7.20 (s, 1H), 7.25 (br, 1H), 7.40 (m, 1H), 8.00 (m, 1H), 8.15 (s, 1H), 8.55 (m, 1H), 8.95 ppm (s, 1H).

Example F

N,N-Dimethyl-2-(pyridin-3-yl)-1,3-oxazole-5-carboxamide

Stage 1: 2-(Pyridin-3-yl)-1,3-oxazole-5-carboxylic acid

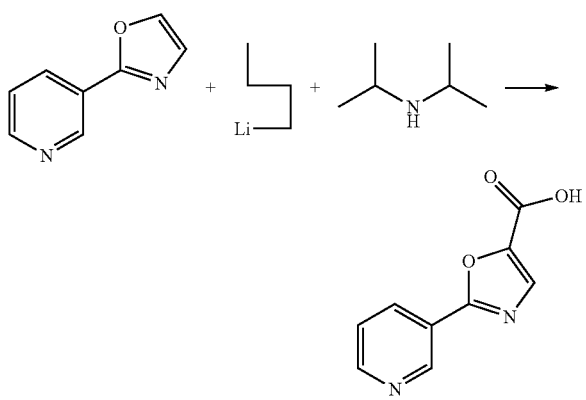

Under argon, 8.80 g (86.5 mmol) of diisopropylamine were dissolved in 250 ml of THF, 40 ml (100 mmol) of n-butyllithium in hexane (2.5 M) were added at 0° C. and, after 10 minutes, 12.4 g (84.5 mmol) of 3-(1,3-oxazol-2-yl)pyridine (obtained according to Helv. Chim. Acta 1962, 45, 375-381) as a solution in 10 ml of after 20 minutes, a few pieces of dry ice were added to the mixture. The mixture was allowed to thaw, aqueous citric acid was added up to pH 6, and the mixture was saturated with sodium chloride and extracted five times with ethyl acetate. The combined organic phases were dried with sodium sulphate and concentrated, the residue was stirred with 200 ml of hot ethanol, insolubles were filtered off and the filtrate was poured into one litre of MTBE (methyl tert-butyl ether). The precipitate was filtered off with suction, dried and purified by chromatography on silica gel (eluent: acetone/methanol).

Yield 9.80 g (55% of theory); HPLC-MS: logP (HCOOH)=−0.06; mass (m/z): 190.9 (M+H)$^+$;

$^1$H NMR (d$_6$-DMSO): 7.35 (s, 1H), 7.55 (dd, 1H), 8.30 (d, 1H), 8.65 (m, 1H), 9.15 ppm (s, 1H).

Stage 2: N,N-Dimethyl-2-(pyridin-3-yl)-1,3-oxazole-5-carboxamide

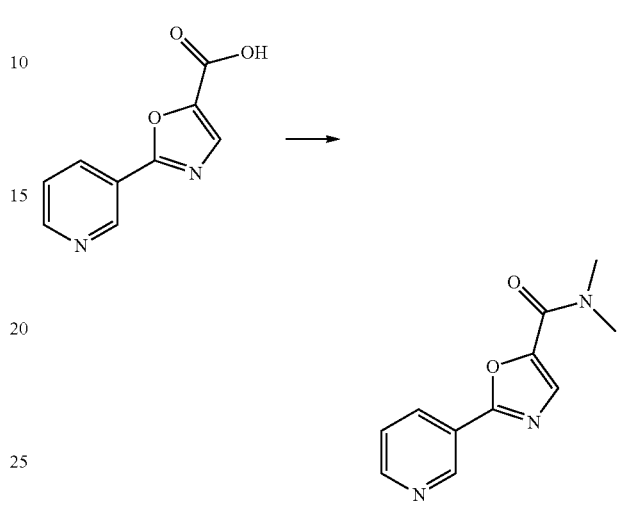

0.70 ml (4.00 mmol) of diisopropylamine was added to 0.30 g (1.60 mmol) of 2-(pyridin-3-yl)-1,3-oxazole-5-carboxylic acid in 15 ml of dichloromethane, and 0.16 ml (1.70 mmol) of ethyl chloroformate was added while cooling in an ice bath. The mixture was stirred for three hours, 0.16 g (1.90 mmol) of dimethylamine hydrochloride was added and the mixture was stirred for two days. The mixture was diluted with dichloromethane, aqueous citric acid and aqueous sodium chloride were added, and the organic phase was dried with sodium sulphate and concentrated. The residue was purified by chromatography on silica gel (cyclohexane/acetone).

Yield: 31.0 mg (9% of theory); HPLC-MS: logP (HCOOH)=1.43; mass (m/z): 272.1 (M+H)$^+$;

$^1$H NMR (CD$_3$CN): 3.05 (br, 3H), 3.30 (br, 3H), 7.50 (m, 1H), 7.65 (s, 1H), 8.35 (d, 1H), 8.70 (m, 1H), 9.25 ppm (s, 1H).

Example G

N-Methyl-5-(pyridin-3-yl)furan-2-carboxamide

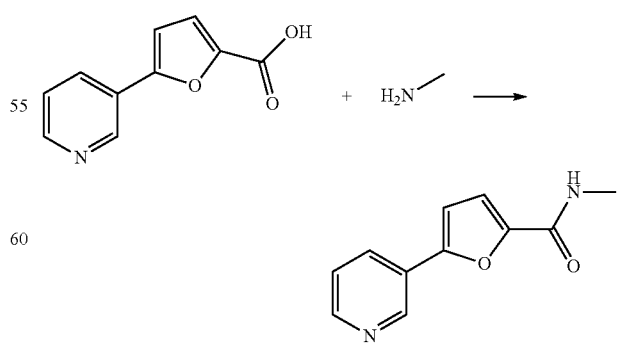

5-(Pyridin-3-yl)furan-2-carboxylic acid (200 mg, 1.06 mmol) (for preparation see U.S. Pat. No. 3,927,008) was initially charged in 30 ml of dioxane, and N-(3-dimethylaminopropyl)-N'-ethylcarbodiimide hydrochloride (253 mg, 1.32 mmol) was added. While stirring, a 2 M solution of methylamine in tetrahydrofuran (41.0 mg, 1.32 mmol) was added dropwise. The mixture was stirred for 3 hours and then 1 ml of water was added. The reaction mixture was stirred at room temperature overnight and then the solvent was removed under reduced pressure. The residue was taken up in water and extracted with ethyl acetate. The organic phase was dried over magnesium sulphate, the solvent was removed on a rotary evaporator and the residue was chromatographed using silica gel (eluent: cyclohexane, ethyl acetate, 1:1 mixture).

Yield: 171 mg (75% of theory); HPLC-MS: logP (HCOOH)=0.42; mass (m/z): 203.1 (M+H)$^+$;

$^1$H NMR (d$_6$-DMSO): 2.56 (d, 3H), 7.50-7.55 (m, 2H), 7.66 (m, 1H), 8.30 (m, 1H), 8.80 (m, 1H), 9.23 (m, 1H), 9.32 ppm (m, 1H).

Example H

N-(2,2-Difluoroethyl)-2-(pyridin-3-yl)-1,3-thiazole-4-carboxamide

Stage 1: Ethyl 2-(pyridin-3-yl)-1,3-thiazole-4-carboxylate hydrobromide

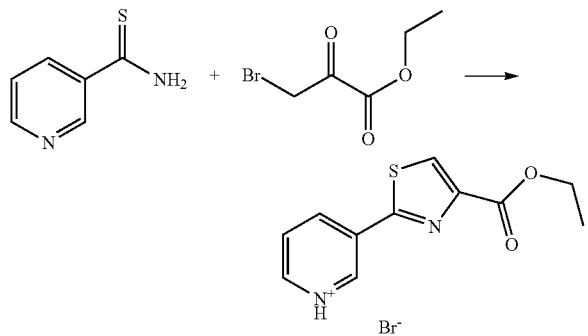

Ethyl 2-(pyridin-3-yl)-1,3-thiazole-4-carboxylate hydrobromide was prepared analogously to literature methods (David A. Degoey et al., US 2005131017 A1, p. 107 ex. 19A).

Stage 2: 2-(Pyridin-3-yl)-1,3-thiazole-4-carboxylic acid

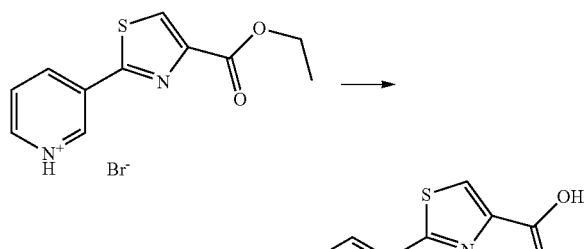

5.90 g (19.0 mmol) of ethyl 2-(pyridin-3-yl)-1,3-thiazole-4-carboxylate hydrobromide were dissolved in 2 ml of water, and 3.30 g (38.0 mmol) of 45% aqueous sodium hydroxide solution were added. After evolution of heat had ended, the mixture was left to react for two hours at room temperature. After cooling with ice-water, the precipitated solid was removed and, while cooling with ice, the reaction solution was adjusted to pH 4 with dilute hydrochloric acid. The precipitated solid was filtered off, washed with water and acetone, and dried under high vacuum.

Yield: 2.03 g (52% of theory); HPLC-MS: logP (HCOOH)=0.35; mass (m/z): 207.0 (M+H)$^+$;

$^1$H NMR (d$_6$-DMSO): 7.55 (m, 1H), 8.35 (m, 1H), 8.50 (s, 1H), 8.70 (m, 1H) 9.15 ppm (m, 1H).

Stage 3: N-(2,2-Difluoroethyl)-2-(pyridin-3-yl)-1,3-thiazole-4-carboxamide

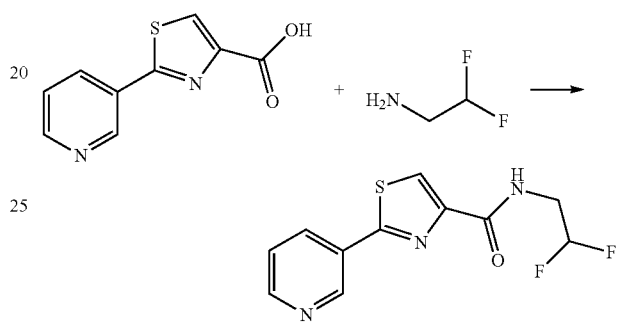

200 mg (0.97 mmol) of 2-(pyridin-3-yl)-1,3-thiazole-4-carboxylic acid were initially charged in 5 ml of toluene, 807 mg (6.78 mmol) of thionyl chloride were added and the mixture was heated under reflux until a clear solution was present. After cooling and removing the solvent on a rotary evaporator, the residue obtained was taken up in toluene and concentrated again. The residue was taken up in 2 ml of acetonitrile, 94.3 mg (1.16 mmol) of N-(2,2-difluoroethyl)amine were initially charged in 2 ml of acetonitrile, and 125 mg (970 μmol) of N,N-diisopropylethylamine were added. The solution of the acid chloride in acetonitrile was added dropwise. The mixture was stirred at room temperature for 15 hours, water and ethyl acetate were added to the reaction solution, and the organic phase was removed. After concentrating, the residue was purified by means of medium pressure chromatography.

Yield: 28.9 mg (10% of theory); HPLC-MS: logP (HCOOH)=1.18; mass (m/z): 270.1 (M+H)$^+$;

$^1$H NMR (d$_6$-DMSO): 3.65-3.80 (m, 2H), 6.00-6.30 (m, 1H), 7.55 (m, 1H), 8.40 (m, 2H), 8.70 (m, 2H), 9.25 ppm (m, 1H).

Example I

N-(2-Methylmercaptoethyl)-5-(pyridin-3-yl)-1,3,4-oxazole-2-carboxamide

Stage 1: Ethyl 5-(pyridin-3-yl)-1,3,4-oxazole-2-carboxylate

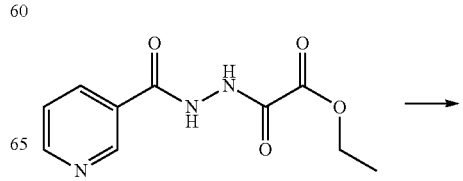

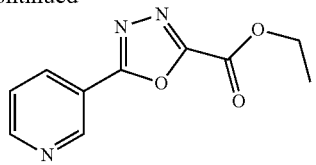

Ethyl 5-(pyridin-3-yl)-1,3,4-oxazole-2-carboxylate was prepared analogously to literature methods.

Ethyl ester: E. Ryzhova, *Pharm. Chem. J.* 2009, 43, 148.
Methyl ester: D. Boger, WO 2006/044617 A1, page 27 line 25.

Stage 2: N-(2-Methylmercaptoethyl)-5-(pyridin-3-yl)-1,3,4-oxazole-2-carboxamide

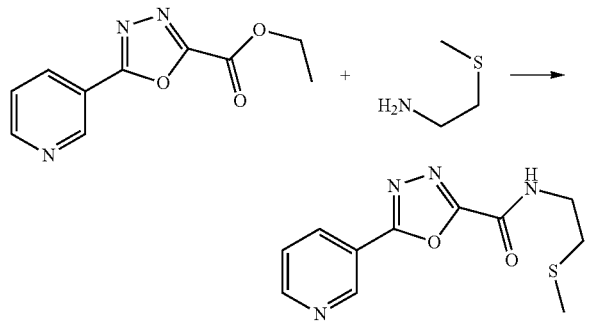

74.5 mg (0.34 mmol) of ethyl 5-(pyridin-3-yl)-1,3,4-oxazole-2-carboxylate and 62.0 mg (0.68 mmol) of 2-methylmercaptoamine were heated to reflux temperature for 15 hours. After cooling, the N-(2-methylmercaptoethyl)-5-(pyridin-3-yl)-1,3,4-oxazole-2-carboxamide was purified by chromatography (eluent: cyclohexane/ethyl acetate 1:1).

Yield: 71.0 mg (94% of theory); HPLC-MS: logP (HCOOH)=1.13; mass (m/z): 265.10 (M+H)$^+$;

$^1$H NMR (d$_6$-DMSO): 2.10 (s, 3H), 2.70 (m, 2H), 3.55 (m, 2H), 7.65 (m, 1H), 8.40 (m, 1H), 8.85 (m, 1H), 9.25 ppm (m, 2H).

Example J 1-(Pyridin-3-yl)-N-(2,2,2-trifluoroethyl)pyrrole-3-carboxamide

Stage 1: Methyl 1-(pyridin-3-yl)pyrrole-3-carboxylate

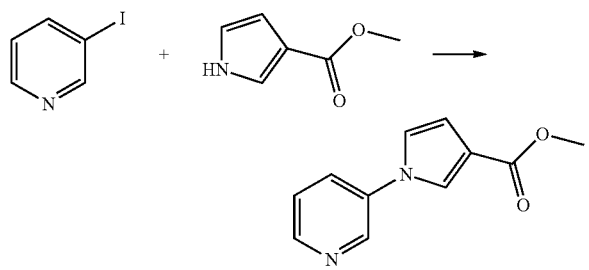

Under argon, 123 mg (0.98 mmol) of methyl 1H-pyrrole-3-carboxylate, 28.1 mg (0.14 mmol) of Cu(I) iodide, 21.5 mg (0.14 mmol) of 8-hydroxyquinoline and 150 mg (1.08 mmol) of potassium carbonate in 1 ml of dimethylformamide were added to 250 mg (1.18 mmol) of 3-iodopyridine, and reacted in a microwave reactor. After 40 minutes (200 watts, 150° C.), the reaction mixture was cooled and filtered through a 1 g silica gel cartridge, the cartridge was washed once again with dimethylformamide, and the solutions were combined and concentrated under reduced pressure. Ethyl acetate/water was added to the residue, which was extracted by shaking. The organic phase was removed and dried over sodium sulphate. The product was obtained after concentrating the solution under reduced pressure.

Yield: 146 mg (85% purity, 52% of theory); HPLC-MS: logP (HCOOH)=1.26; mass (m/z): 203.0 (M+H)$^+$, Stage 2: 1-(Pyridin-3-yl)pyrrole-3-carboxylic acid lithium salt

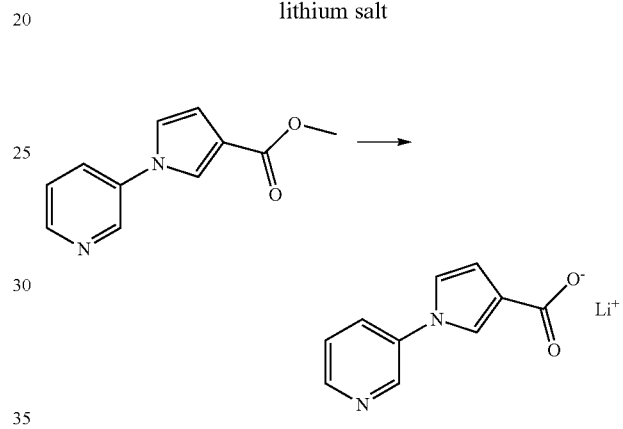

147 mg (720 mop of methyl 1-(pyridin-3-yl)pyrrole-3-carboxylate were initially charged in 1 ml of tetrahydrofuran, and a solution of 88.8 mg (3.62 mmol) of lithium hydroxide in a little methanol/water (1:1) was added. The suspension which formed at first after addition of the lithium hydroxide solution went into a clear solution. After 48 hours at room temperature, the mixture was stirred at 50° C. for 15 hours. After concentration under reduced pressure, the crude lithium salt was obtained, which was used in the next reaction step without further purification.

Yield: 149 mg (100% of theory)

Stage 3: 1-(Pyridin-3-yl)-N-(2,2,2-trifluoroethyl)pyrrole-3-carboxamide

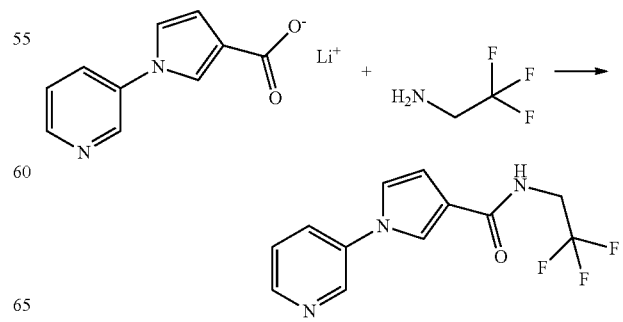

149 mg (760 μmol) of lithium salt of 1-(pyridin-3-yl)pyrrole-3-carboxylic acid were dissolved in 3 ml of N,N-dimethylformamide and the mixture was stirred at room temperature for 10 minutes. After addition of 82.0 mg (8.30 mmol) of trifluoroethylamine and a solution of N,N-diisopropylethylamine in dimethylformamide, the mixture was stirred at room temperature for 15 hours. After the reaction solution had been concentrated, the remaining residue was purified by means of medium pressure chromatography.

Yield: 101 mg (10% of theory); HPLC-MS: logP (HCOOH)=1.24; mass (m/z): 270.0 (M+H)$^+$;

$^1$H NMR (d$_6$-DMSO): 4.05 (m, 2H), 6.81 (m, 1H), 7.50-7.55 (m, 2H), 8.07 (m, 2H), 8.50 (m, 2H), 8.90 ppm (m, 1H).

Example K

N-(2,2-Difluoropropyl)-1-(pyridin-3-yl)-1H-1,2,3-triazole-4-carboxamide

Stage 1: Ethyl 1-(pyridin-3-yl)-1H-1,2,3-triazole-4-carboxylate

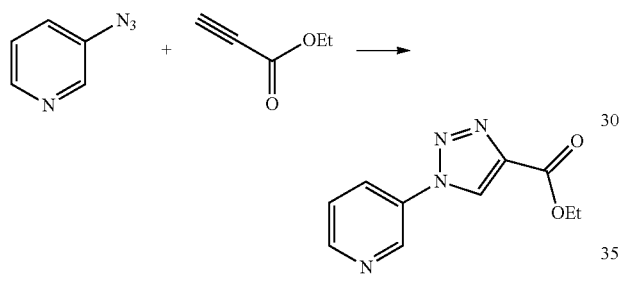

1.70 g (14.2 mmol) of 3-azidopyridine (for preparation see US 1987/49196, CAUTION explosive!) and 1.38 g (14.2 mmol) of ethyl prop-2-ynoate were initially charged in a mixture of 15 ml of water and 15 ml of tert-butanol, 280 mg (1.42 mmol) of sodium salt of L-ascorbic acid and 383 mg (1.42 mmol) of copper(II) sulphate pentahydrate were added, and then the mixture was stirred at room temperature for 17 hours. The reaction mixture was added to water and extracted repeatedly with tert-butyl methyl ether, and the organic phases were dried over magnesium sulphate, filtered and concentrated. The product was obtained after chromatographic purification.

Yield 573 mg (19% of theory); HPLC-MS: logP (HCOOH)=1.15; mass (m/z) 219.1 (M+H)$^+$;

$^1$H NMR (d$_6$-DMSO) 1.35 (t, 3H), 4.38 (q, 2H), 7.68 (dd, 1H), 8.41 (ddd, 1H), 8.74 (dd, 1H), 9.20 ppm (d, 1H).

Stage 2: 1-(Pyridin-3-yl)-1H-1,2,3-triazole-4-carboxylic acid

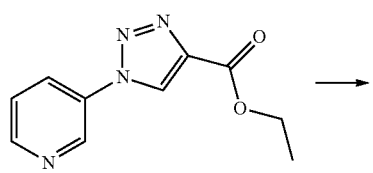

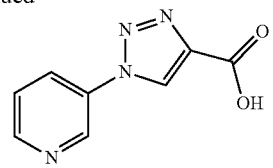

557 mg (2.30 mmol) of ethyl 1-(pyridin-3-yl)-1H-1,2,3-triazole-4-carboxylate were dissolved in 15 ml of ethanol, 4.60 ml (4.60 mmol) of 1 M sodium hydroxide solution were added and the mixture was stirred at room temperature for three days. The reaction mixture was concentrated, water and ethyl acetate were added and the pH was adjusted to 4 by adding 1 M hydrochloric acid. After extracting repeatedly with ethyl acetate, the combined organic phases were dried over magnesium sulphate, filtered and concentrated under reduced pressure. The product was obtained as a colourless solid.

Yield 120 mg (27% of theory); HPLC-MS: logP (HCOOH)=−0.03; mass (m/z): 191.1 (M+H)$^+$;

$^1$H NMR (d$_6$-DMSO): 7.68 (dd, 1H), 8.40 (ddd, 1H), 8.74 (dd, 1H), 9.20 (d, 1H), 9.47 ppm (s, 1H).

Stage 3: N-(2,2-Difluoropropyl)-1-(pyridin-3-yl)-1H-1,2,3-triazole-4-carboxamide

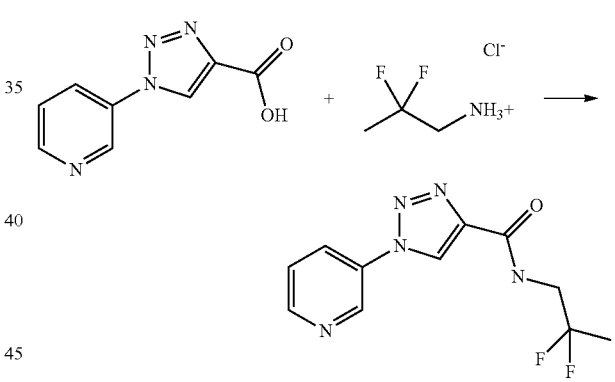

110 mg (578 mmol) of 1-(pyridin-3-yl)-1H-1,2,3-triazole-4-carboxylic acid were dissolved in 8 ml of dichloromethane, and 99.0 μl (1.16 mmol) of oxalyl chloride and one drop of N,N-dimethylformamide were added. The reaction mixture was stirred at room temperature for 4 hours and then concentrated on a rotary evaporator. The residue in 10 ml of dichloromethane was added to a solution of 105 mg (798 mmol) of 2,2-difluoropropan-1-amine hydrochloride and 157 μl (1.43 mmol) of N-methylmorpholine in 15 ml of dichloromethane, and the mixture was stirred at room temperature overnight. The reaction mixture was filtered through silica gel (ethyl acetate), the filtrate was washed with saturated ammonium chloride solution, and the latter was extracted with ethyl acetate. The combined organic phases were dried over magnesium sulphate, filtered and concentrated.

Yield 114 g (75% of theory); HPLC-MS: logP (HCOOH)=1.25; mass (m/z): 267.9 (M+H)$^+$;

¹H NMR (d₆-DMSO) 1.64 (t, 3H), 3.75 (dt, 2H), 7.68 (dd, 1H), 8.40 (ddd, 1H), 8.74 (dd, 1H), 8.97 (t, 1H), 9.19 (d, 1H), 9.42 ppm (s, 1H).

Example L

N-(2,2-Difluoropropyl)-3-(pyridin-3-yl)-1,2-thiazole-5-carboxamide

Stage 1: Ethyl 3-(6-chloropyridin-3-yl)-1,2-thiazole-5-carboxylate

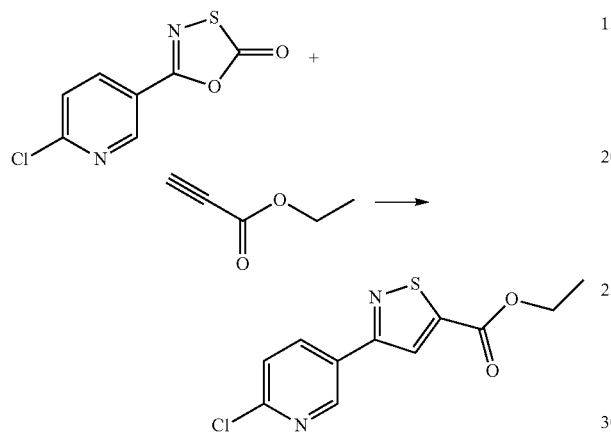

2.26 g (10.5 mmol) of 5-(6-chloropyridin-3-yl)-1,3,4-oxathiazol-2-one (preparation in analogy to *J. Med. Chem.* 2001, 44, 1560-1563) and 5.33 ml (52.6 mmol) of ethyl prop-2-ynoate were dissolved in 100 ml of 1,2-dichlorobenzene and stirred at 150° C. overnight. The solvent was removed under reduced pressure and the crude product was purified by chromatography.

Yield 880 mg (31% of theory); HPLC-MS: logP (HCOOH)=3.33; mass (m/z) 268.9 (M+H)⁺;

¹H NMR (d₆-DMSO) 1.35 (t, 3H), 4.40 (q, 2H), 7.67 (d, 1H), 8.52 (dd, 1H), 8.65 (s, 1H, 9.13 ppm (d, 1H).

Stage 2: 3-(6-Chloropyridin-3-yl)-1,2-thiazole-5-carboxylic acid

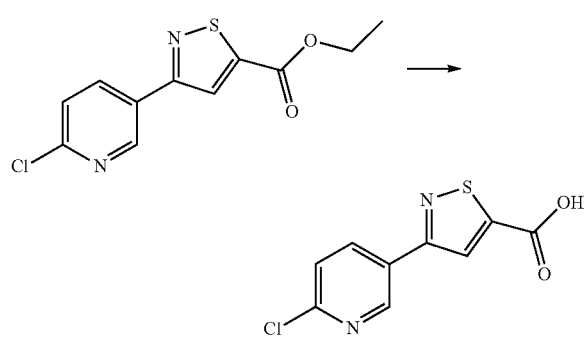

350 mg (1.30 mmol) of ethyl 3-(6-chloropyridin-3-yl)-1,2-thiazole-5-carboxylate were dissolved in 30 ml of methanol, 2.61 ml (2.61 mmol) of 1 M sodium hydroxide solution were added and the mixture was stirred at room temperature overnight. The reaction mixture was concentrated, water and ethyl acetate were added and the pH was adjusted to 4 by adding 1 M hydrochloric acid. After extracting repeatedly with ethyl acetate, the combined organic phases were dried over magnesium sulphate, filtered and concentrated under reduced pressure.

Yield 311 mg (99% of theory); HPLC-MS: logP (HCOOH)=1.56; mass (m/z) 241.0 (M+H)⁺;

¹H NMR (d₆-DMSO) 7.66 (d, 1H), 8.51 (dd, 1H), 8.54 (s, 1H), 9.12 ppm (d, 1H).

Stage 3: 3-(6-Chloropyridin-3-yl)-N-(2,2-difluoropropyl)-1,2-thiazole-5-carboxamide

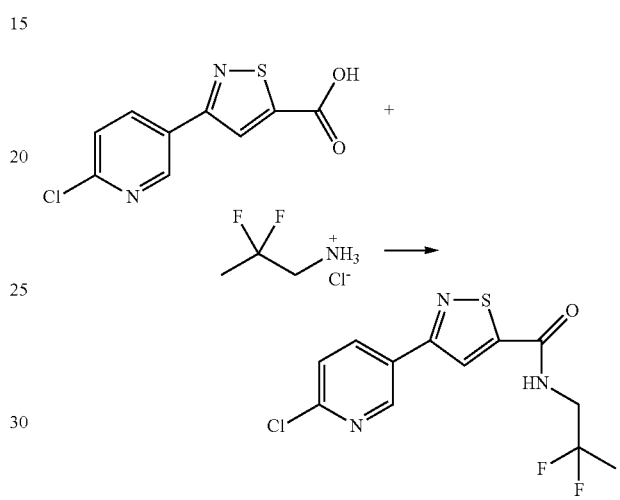

186 mg (772 µmol) of 3-(6-chloropyridin-3-yl)-1,2-thiazole-5-carboxylic acid were dissolved in 4 ml of dichloromethane, and 133 µl (1.54 mmol) of oxalyl chloride and one drop of dimethylformamide were added. The reaction mixture was stirred at room temperature for four hours and then concentrated on a rotary evaporator. The residue in 10 ml of dichloromethane was added to a solution of 142 mg (1.08 mmol) of 2,2-difluoropropan-1-amine hydrochloride and 212 µl (1.93 mmol) of N-methylmorpholine in 15 ml of dichloromethane, and the mixture was stirred at room temperature overnight. The reaction mixture was filtered through silica gel (dichloromethane, ethyl acetate), the filtrate was concentrated and the residue was purified by chromatography.

Yield 68.2 mg (28% of theory); HPLC-MS: logP (HCOOH)=2.45; mass (m/z): 318.0 (M+H)⁺;

¹H NMR (d₆-DMSO) 1.67 (t, 3H), 3.78 (dt, 2H), 7.71 (d, 1H), 8.39 (dd, 1H), 8.61 (s, 1H), 8.99 (d, 1H), 9.26 ppm (t, 1H).

Stage 4: N-(2,2-Difluoropropyl)-3-(pyridin-3-yl)-1,2-thiazole-5-carboxamide

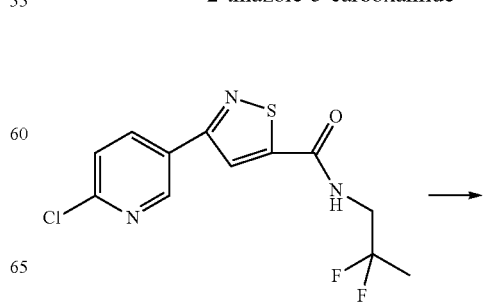

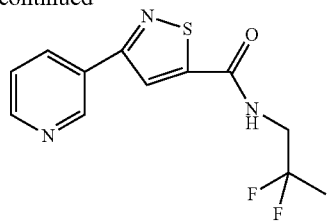

53.0 mg (163 μmmol) of 3-(6-chloropyridin-3-yl)-N-(2,2-difluoropropyl)-1,2-thiazole-5-carboxamide were initially charged in 5 ml of methanol, 17.4 mg of palladium on activated carbon (10%) were added and the mixture was stirred under a hydrogen atmosphere overnight. The reaction mixture was filtered through Celite/silica gel (ethyl acetate) and the filtrate was concentrated on a rotary evaporator.

Yield 23.2 g (58% of theory); HPLC-MS: logP (HCOOH)=1.33; mass (m/z): 284.1 (M+H)$^+$;

$^1$H NMR (d$_6$-DMSO) 1.67 (t, 3H), 3.77 (dt, 2H), 7.58 (dd, 1H), 8.34 (m, 1H), 8.68 (dd, 1H), 8.72 (s, 1H), 9.17 (d, 1H), 9.38 ppm (t, 1H).

Example M 5-(Pyridin-3-yl)-N-(2,2,2-trifluoroethyl)-1,2-oxazole-3-carboxamide

Stage 1: 5-(Pyridin-3-yl)-1,2-oxazole-3-carbonyl chloride

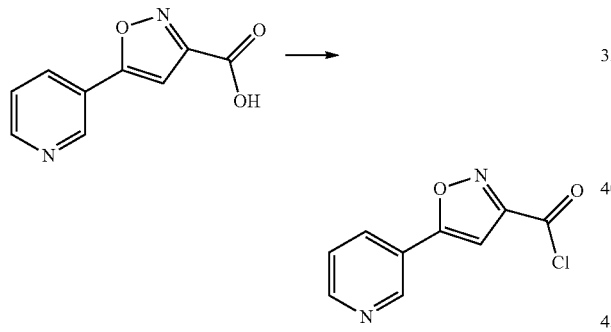

0.5 g (2.63 mmol) of 5-(pyridin-3-yl)-1,2-oxazole-3-carboxylic acid (known from the literature, no reference) in 25 ml of dichloromethane was admixed with 2 drops of N,N-dimethylformamide. Subsequently, 0.97 g (7.63 mmol) of oxalyl chloride was added dropwise under argon and the reaction mixture was stirred at room temperature for 1 hour. The solvent was removed under reduced pressure and the crude product was converted farther immediately.

Stage 2: 5-(Pyridin-3-yl)-N-(2,2,2-trifluoroethyl)-1,2-oxazole-3-carboxamide

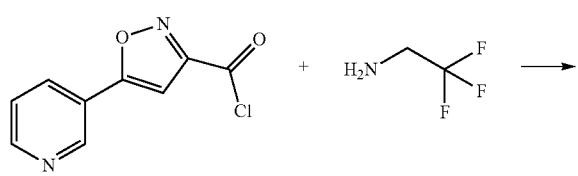

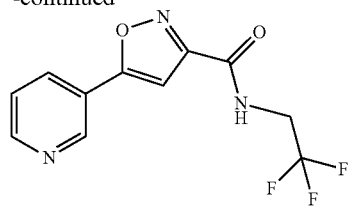

0.29 g (2.92 mmol) of 1,1,1-trifluoroethylamine in 30 ml of dioxane was admixed with 1.13 g (8.77 mmol) of diisopropylethylamine. Thereafter, 0.61 g (2.92 mmol) of 5-pyridin-3-yl)-1,2-oxazole-3-carbonyl chloride, slurried in 30 ml of dioxane, was added in portions. The reaction mixture was stirred at room temperature for 16 hours, then the solvent was removed under reduced pressure. The residue was taken up in ethyl acetate and washed with water. The organic phase was dried over magnesium sulphate and the solvent was removed under reduced pressure.

Yield 0.33 g (42% of theory); HPLC-MS: logP (HCOOH)=1.51; mass (m/z) 272.0 (M+H)$^+$;

$^1$H NMR (d$_6$-DMSO) 4.04-4.13 (m, 2H), 7.49 (s, 1H), 7.56-7.60 (m, 1H), 8.28-8.31 (m, 1H), 8.70-8.72 (m, 1H), 9.12-9.13 (m, 1H), 9.29 ppm (bs, 1H).

Example N (R,S)-4,5-Dihydro-N,N-dimethyl-2-(3-pyridinyl)-1,3-thiazole-5-carboxamide Stage 1: (R,S)-4,5-Dihydro-2-(3-pyridinyl)-1,3-thiazole-5-carboxylic acid

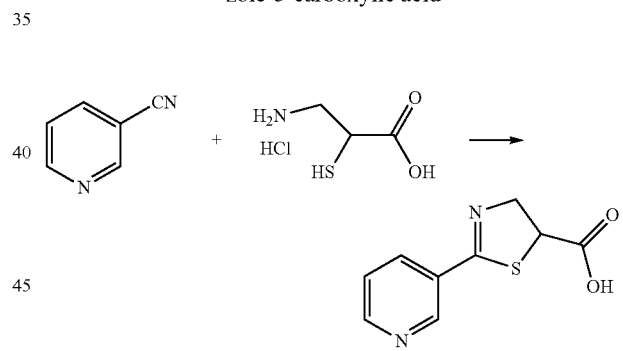

654.3 mg (6.28 mmol) of 3-cyanopyridine were initially charged with 691.6 mg (8.23 mmol) of sodium bicarbonate in 33 ml of phosphate buffer solution (pH 6), and admixed with 1297.6 mg (8.23 mmol) of isocysteine hydrochloride (preparation in analogy to Ch. Dose, O. Seitz Org. Biomol. Chem. 2004, 2, 59-65; Bioorg. Med. Chem. 2008, 16, 65-77), dissolved in 50 ml of methanol. Thereafter, the reaction mixture was stirred at 60° C. for 15 hours. After cooling, the reaction mixture was concentrated under reduced pressure and the remaining residue was stirred successively with acetonitrile, acetone, N,N-dimethylformamide and chloroform. The remaining solid was purified by means of medium-pressure chromatography (RP column, eluent: water).

Yield 750 mg (57% of theory); HPLC-MS: logP (HCOOH)=0.75; mass (m/z) 209.0 (M+H)$^+$;

$^1$H NMR (d$_6$-DMSO) 4.35-4.45 (m, 2H), 4.61-4.72 (m, 1H), 7.49 (d, 1H), 8.06 (dd, 1H), 8.67 (d, 1H), 8.88 ppm (d, 1H).

Stage 2: (R,S)-4,5-Dihydro-N,N-dimethyl-2-(3-pyridinyl)-1,3-thiazole-5-carboxamide

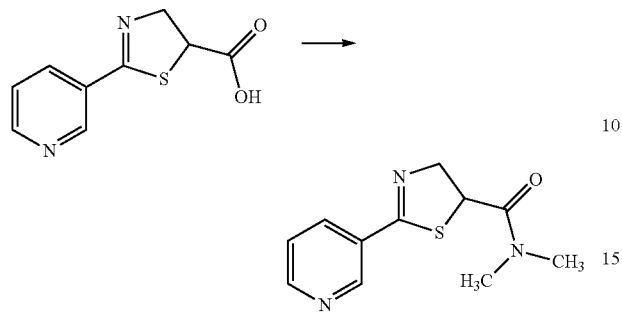

A mixture of 300.0 mg (1.44 mmol) of (R,S)-4,5-dihydro-2-(3-pyridinyl)-1,3-thiazole-5-carboxylic acid and 77.9 mg (0.86 ml; 1.72 mmol) of a 2M solution of dimethylamine in tetrahydrofuran was admixed successively with 146.0 mg (1.08 mmol) of I-hydroxy-1H-benzotriazole in 10 ml of N,N-dimethylformamide and 201.2 mg (1.29 mmol) of N-ethyl-N'-(3-dimethylaminopropyl)carbo-diimide, and then the mixture was stirred at room temperature for approx. 18 hours. For workup, the mixture was first admixed with water and then extracted with dichloromethane and ethyl acetate. After the removal of the organic phase, drying and concentration under reduced pressure, the remaining residue was purified by means of medium-pressure chromatography (silica gel, eluent: cyclohexane-acetone).

Yield 46 mg (12% of theory).

$^{13}$C with $^{1}$H decoupling (CPD), 2D NMR (CDCl$_3$) 36.3, 37.9 (N—CH$_3$), 48.3 (CH), 67.8 (CH$_2$), 161.7 (C=N), 123.4, 128.6, 135.4, 149.4, 151.9 (Py-C), 169.5 (C=O) ppm.

Example O (R,S)-4,5-Dihydro-N-(pyrimidin-2-ylmethyl)-2-(5-pyrimidinyl)-1,3-thiazole-5-carboxamide Stage 1: (R,S)-4,5-Dihydro-2-(5-pyrimidinyl)-1,3-thiazole-5-carboxylic acid

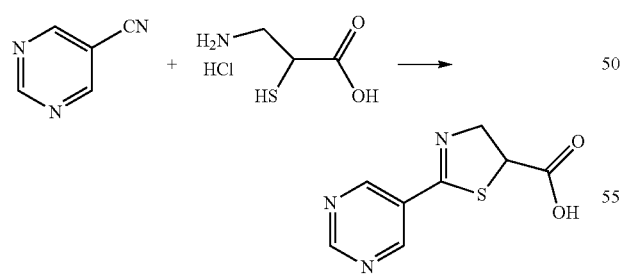

1.00 g (9.51 mmol) of 5-cyanopyrimidine were initially charged with 1.04 g (12.3 mmol) of sodium bicarbonate in 50 ml of phosphate buffer solution (pH 6), and admixed with 1.95 g (12.3 mmol) of isocysteine hydrochloride (preparation in analogy to Ch. Dose, O. Seitz *Org. Biomol. Chem.* 2004, 2, 59-65; *Bioorg. Med. Chem.* 2008, 16, 65-77), dissolved in 50 ml of methanol. Thereafter, the reaction mixture was stirred at 60° C. for 15 hours. After cooling, the mixture was concentrated under reduced pressure and the remaining residue was stirred successively with acetonitrile, acetone, N,N-dimethylformamide and chloroform. The remaining solid was purified by means of medium-pressure chromatography (RP column, eluent: water).

HPLC-MS: logP (HCOOH)=0.30; mass (m/z) 210.0 (M+H)$^+$;

$^{1}$H NMR (d$_6$-DMSO) 4.28-4.71 (m, 3H), 9.06 (d, 1H), 9.30 ppm (d, 2H).

Stage 2: (R,S)-4,5-Dihydro-N-(pyrimidin-2-ylmethyl)-2-(5-pyrimidinyl)-1,3-thiazole-5-carboxamide

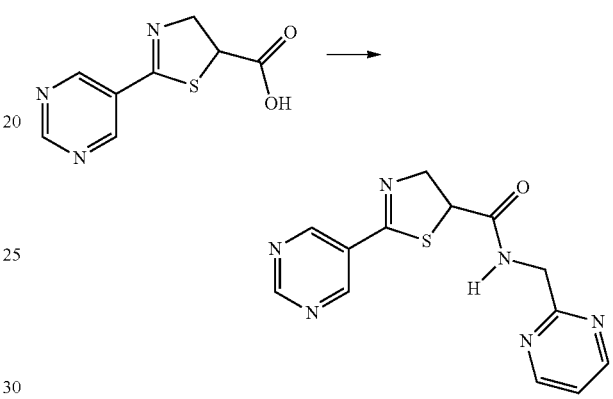

A mixture of 376.7 mg (1.80 mmol) of (R,S)-4,5-dihydro-2-(5-pyrimidinyl)-1,3-thiazole-5-carboxylic acid and 314.6 mg (2.16 mmol) of 2-pyrimidinemethanamine in 10 ml of N,N-dimethylformamide was admixed successively with 182.5 mg (1.35 mmol) of 1-hydroxy-1H-benzotriazole and 251.6 mg (1.62 mmol) of N-ethyl-N'-(3-dimethylaminopropyl)carbodiimide, and then the mixture was stirred at room temperature for approx. 18 hours. For workup, the mixture was first admixed with water and then extracted with dichloromethane and ethyl acetate. After the removal of the organic phase, drying and concentration under reduced pressure, remaining residue was purified by means of medium-pressure chromatography (silica gel, eluent: cyclohexane-acetone).

Yield: 156 mg (28% of theory); HPLC-MS: logP (HCOOH)=0.90; mass (m/z) 301.1 (M+H)$^+$;

$^{1}$H NMR (d$_6$-DMSO) 4.66-4.86 (m, 5H), 7.41-7.42 (m, 1H), 8.77-8.79 (m, 2H), 8.87-8.89 (m, 1H), 9.11 (d, 2H), 9.34 ppm (d, 1H).

Example P

4-Methyl-5-(3-pyridyl)-N-(2,2,2-trifluoroethyl)-1,3-thiazole-2-carboxamide

Stage 1: Ethyl 4-methyl-5-(3-pyridinyl)-1,3-thiazole-2-carboxylate

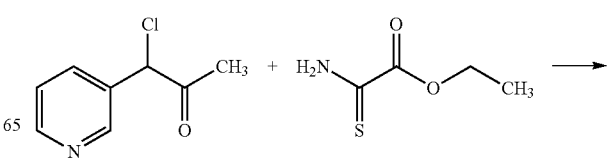

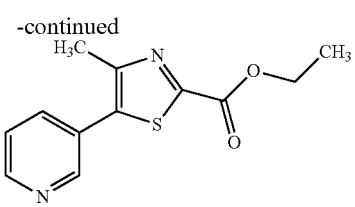

2.50 g (14.7 mmol) of 1-chloro-1-(3-pyridinyl)-2-propane (for preparation cf. EP 0 117 082) were dissolved in 10 ml of N,N-dimethylformamide, admixed with 1.96 g (14.7 mmol) of ethyl thiooxamate and stirred at 100° C. for 30 min. For workup, the mixture was cooled, diluted with water and extracted with ethyl acetate, and the organic phase was dried and concentrated under reduced pressure. A further purification was effected by means of column chromatography on silica gel (cyclohexane/ethyl acetate).

Yield: 0.68 g (18% of theory); HPLC-MS: logP (HCOOH)=0.45.

Stage 2: 4-Methyl-5-(3-pyridyl)-N-(2,2,2-trifluoroethyl)-1,3-thiazole-2-carboxamide 0.40 ml (58 mg, 0.80 mmol) of trimethylaluminium solution were added dropwise under argon to 40 mg (0.40 mmol) of 2,2,2-trifluoroethylamine in 8 ml of toluene. After 15 minutes, a solution of 100 mg (0.40 mmol) of ethyl 4-methyl-5-(3-pyridinyl)-1,3-thiazole-2-carboxylate (cf. stage 1) in 2 ml of toluene was added dropwise and the mixture was heated at reflux overnight. For workup, the mixture was cooled, 1 ml of 1N hydrochloric acid was added dropwise, and the whole mixture was transferred into 5 ml of 1N sodium hydroxide solution and extracted with dichloromethane. Subsequently, the organic phase was dried and concentrated under reduced pressure. The remaining residue was purified by means of column chromatography on silica gel (cyclohexane/ethyl acetate).

Yield: 10 mg (7% of theory); HPLC-MS: logP (HCOOH)=1.74; mass (m/z)=302.1 (M$^+$);

$^1$H NMR (CDCl$_3$)=2.54 (s, 3H), 4.11 (m, 2H), 7.41 (m, 1H), 7.55 (br, 1H), 7.78 (m, 1H), 8.68 (m, 1H), 8.75 (m, 1H) ppm.

Example Q

4-Methyl-5-(3-pyridyl)-N-(2,2,2-trifluoroethyl)-1,3-thiazole-2-carboxamide 100 mg (0.68 mmol) of 3-(1H-pyrazol-4-yl)pyridine and 86 mg (0.68 mmol) of 1,1,1-trifluoro-2-isocyanatoethane were stirred in 10 ml of tetrahydrofuran at room temperature for 16 h, then the solvent was removed under reduced pressure.

Yield: 179 mg (96% of theory); HPLC-MS: logP (HCOOH)=0.95; mass (m/z)=271.0 (M$^+$);

$^1$H NMR (d$_6$-DMSO)=4.08 (m, 2H), 7.40 (m, 1H), 8.10 (m, 1H), 8.38 (m, 1H), 8.48 (m, 1H), 8.89 (m, 1H), 9.00 (m, 2H) ppm.

Example R 5-(Pyridin-3-yl)-N-(2,2,2-trifluoroethyl)-1,3,4-oxadiazole-2-carboxamide Stage 1: Ethyl 5-(pyridin-3-yl)-1,3,4-oxadiazole-2-carboxylate

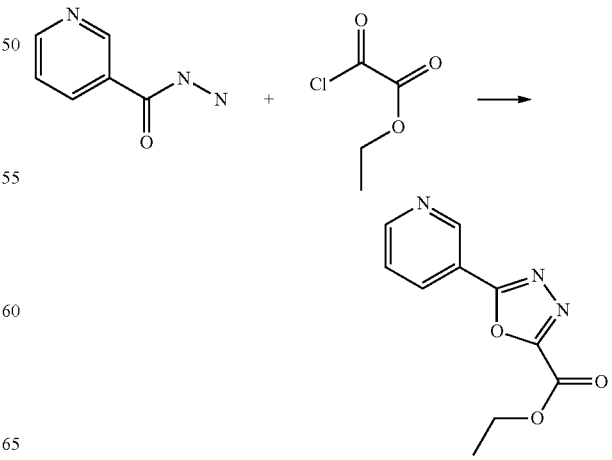

11.6 g (83 mmol) of ethyl oxalyl chloride (commercially available) in 50 ml of dichloromethane were added dropwise while cooling with ice to a mixture of 10 g (73 mmol) of nicotine hydrazide (commercially available) and 22 g (219 mmol) of triethylamine in 200 ml of dichloromethane. The reaction mixture was stirred at room temperature for 4 hours. Subsequently, 13.9 g (73 mmol) of para-toluenesulphonyl chloride were added in portions. The reaction mixture was stirred at room temperature overnight, then the solvent was removed on a rotary evaporator. The residue was admixed with ethyl acetate and water. The organic phase was dried over sodium sulphate, the solvent was removed on a rotary evaporator, and the residue was chromatographed using silica gel (gradient: cyclohexane/ethyl acetate).

Yield: 12.6 g (78.8% of theory); HPLC-MS: logP (HCOOH)=1.21; mass (m/z): 219.2 (M+H)$^+$;

$^1$H NMR (d$_6$-DMSO): 1.4 (t, 3H) 4.5 (m, 2H), 7.65 (m, 1H) 8.4 (m, 1H), 8.85 (m, 1H) 9.2 ppm (s, 1H).

Stage 2: 5-(Pyridin-3-yl)-N-(2,2,2-trifluoroethyl)-1,3,4-oxadiazole-2-carboxamide

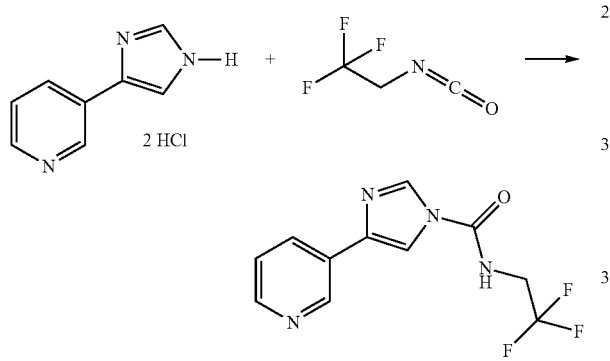

A mixture of 100 mg (0.456 mmol) of ethyl 5-(pyridin-3-yl)-1,3,4-oxadiazole-2-carboxylate (stage 1) and 90.38 mg (0.912 mmol) of 2,2,2-trifluoroethylamine (commercially available) was heated in a microwave at 300 watts and 140° C. for 10 minutes. After cooling, the reaction mixture was dissolved in dichloromethane and the precipitate which formed was filtered off with suction.

Yield: 8.2 mg (6.6% of theory); HPLC-MS: logP (HCOOH)=1.21; mass (m/z) 272.2 (M+H)$^+$, $^1$H NMR (d$_6$-DMSO): 4.15 (m, 2H) 7.7 (m, 1H) 8.45 (m, 1H) 8.85 (m, 1H) 9.25 (s, 1H) 10 ppm (m, 1H).

Example S

5-Methyl-1-(pyridin-3-yl)-N-(2,2,2-trifluoroethyl)-1H-imidazole-4-carboxamide

Stage 1: Ethyl 5-methyl-1-(pyridin-3-yl)-1H-imidazole-4-carboxylate

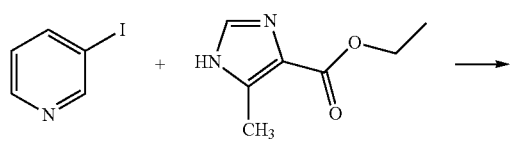

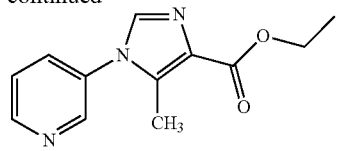

A mixture of 250 mg (1.183 mmol) of 3-iodopyridine (commercially available), 155.1 mg (0.986 mmol) of ethyl 5-methyl-1H-imidazole-4-carboxylate (commercially available), 28.2 mg (0.15 mmol) of copper(I) iodide, 21.5 mg (0.15 mmol) of 8-hydroxyquinoline and 150 mg (1.084 mmol) of potassium carbonate were initially charged in 1 ml of dimethyl sulphoxide in a microwave vessel. In the microwave, the reaction mixture was heated at 200 watts and 150° C. for 40 minutes. Subsequently, the mixture was filtered through a 1 g silica gel cartridge and washed with ethyl acetate. Then the reaction mixture was washed once with water, the organic phase was dried over sodium sulphate and the solvent was removed on a rotary evaporater.

Yield: 88.5 mg (32.4% of theory); logP (HCOOH)=1.03; mass (m/z): 231.3 (M+H)$^+$ Stage 2: 5-Methyl-1-(pyridin-3-yl)-N-(2,2,2-trifluoroethyl)-1H-imidazole-4-carboxamide

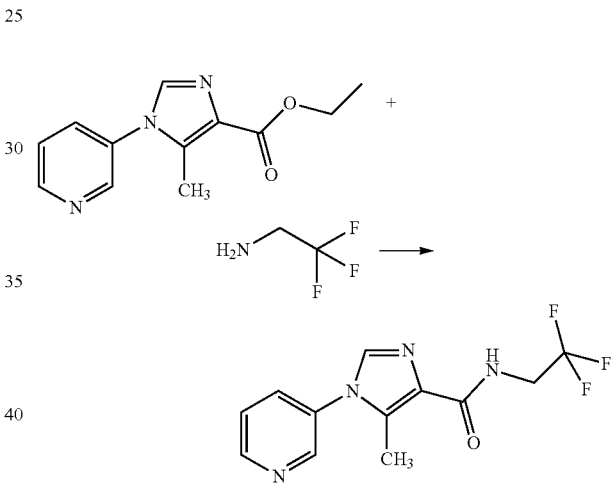

45.8 mg (1.9 mmol) of lithium hydroxide, dissolved in 1:1 methanol/water, were added to 88.5 mg (0.383 mmol) of ethyl 5-methyl-1-(pyridin-3-yl)-1H-imidazole-4-carboxylate in 2 ml of tetrahydrofuran. Then the mixture was stirred at 50° C. overnight. The solvent was removed on a rotary evaporator and the residue was dried under high vacuum.

The residue was taken up in 1 ml of N,N-dimethylformamide and added to an initial charge composed of 41.3 mg (0.42 mmol) of 2,2,2-trifluoroethylamine (commercially available), 133.8 mg (0.417 mmol) of N-[(1H-benzotriazol-1-yloxy)(dimethylamino)methylene]-N-methylmethanaminium tetrafluoroborate (TBTU) and 73.5 mg (0.57 mmol) of N,N-diisopropylethylamine in 1 ml of N,N-dimethylformamide. Subsequently, the mixture was stirred at room temperature overnight. The solvent was removed on a rotary evaporator and the residue was purified by means of high-pressure chromatography.

Yield: 7.4 mg (6.87% of theory); HPLC-MS: logP (HCOOH)=1.28; mass (m/z): 284.2 (M+H)$^+$ $^1$H NMR (d$_6$-DMSO): 2.45 (s, 3H), 4.0 (m, 1H), 7.65 (m, 1H), 8 (s, 1H), 8.05 (m, 1H), 8.55 (m, 1H), 8.7 (m, 1H), 8.75 ppm (s, 1H).

Analogously to or in accordance with the general details regarding the preparation, the compounds listed in the following table were prepared:

| Compound number | Structure | logP[1] (HCO$_2$H) | (M + H)$^+$ | NMR data[2] |
|---|---|---|---|---|
| 1 (Example A) | 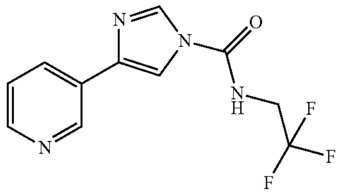 [SMILES: O=C(NCC(F)(F)F)n1cnc(-c2cccnc2)c1] | 0.65 | 271.1 | $^1$H NMR (d$_6$-DMSO): 4.14-4.20 (m, 1H), 7.44-7.46 (m, 1H), 8.17-8.19 (m, 1H), 8.36 (d, 1H), 8.47 (d, 1H), 8.49-8.50 (m, 1H), 9.05 (d, 1H), 9.34-9.37 ppm (m, 1H). |
| 2 (Example B) | 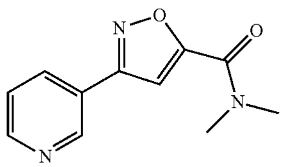 [SMILES: CN(C)C(=O)c1cc(-c2cccnc2)no1] | 0.78 | 218.1 | $^1$H NMR (d$_6$-DMSO): 3.06 (s, 6H), 7.53-7.57 (m, 2H), 8.28-8.31 (m, 1H), 8.70-8.72 (m, 1H), 9.10-9.11 ppm (m, 1H). |
| 3 | 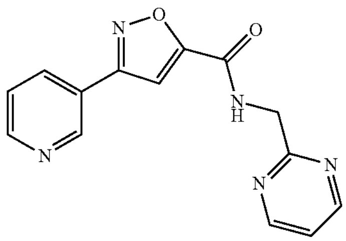 [SMILES: O=C(NCc1ncccn1)c1cc(-c2cccnc2)no1] | 0.62 | 282.1 | $^1$H NMR (d$_6$-DMSO): 4.44-4.70 (m, 1H), 7.39 (t, 1H), 7.55-7.58 (m, 1H), 7.69 (s, 1H), 8.28-8.31 (m, 1H), 8.71-8.73 (m, 1H), 8.77 (d, 2H), 9.09-9.11 (m, 1H), 9.31 ppm (broad, NH). |
| 4 (Example C) | 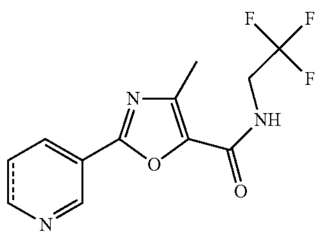 | 1.46 | 286.1 | $^1$H NMR (d$_6$-DMSO): 3.32 (s, 3H), 4.10 (m, 2H), 7.63 (m, 1H), 8.50 (m, 1H), 8.78 (m, 1H), 9.22 (m, 1H), 9.35 ppm (m, 1H). |
| 5 (Example D) | 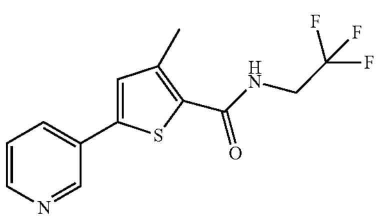 [SMILES: Cc1cc(-c2cccnc2)sc1C(=O)NCC(F)(F)F] | 1.62 | 301.1 | $^1$H NMR (d$_6$-DMSO): 2.42 (s, 3H), 4.05 (m, 2H), 7.45 (m, 2H), 8.05 (m, 1H), 8.48 (m, 1H), 8.53 (m, 1H), 8.88 ppm (m, 1H). |
| 6 | 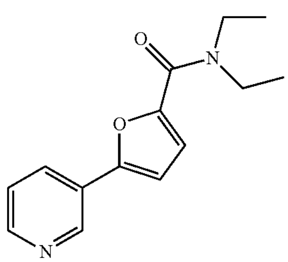 [SMILES: CCN(CC)C(=O)c1ccc(-c2cccnc2)o1] | 1.23 | 245.1 | $^1$H NMR (CD$_3$CN): 1.30 (br, 6H), 3.60 (br, 4H), 6.95 (d, 1H), 7.05 (d, 1H), 7.40 (m, 1H), 8.05 (m, 1H), 8.55 (m, 1H), 8.95 ppm (s, 1H). |
| 7 | 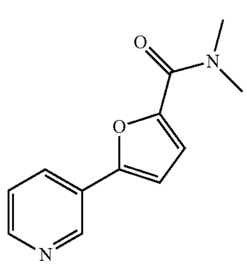 [SMILES: CN(C)C(=O)c1ccc(-c2cccnc2)o1] | 0.51 | 217.1 | $^1$H NMR (CD$_3$CN): 3.00-3.40 (br, 6H), 6.95 (d, 1H), 7.05 (d, 1H), 7.40 (m, 1H), 8.05 (m, 1H), 8.55 (m, 1H), 8.95 ppm (m, 1H). |

-continued

| Compound number | Structure | logP[1] (HCO$_2$H) | (M + H)$^+$ | NMR data[2] |
|---|---|---|---|---|
| 8 | 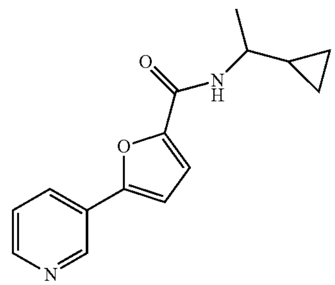 [SMILES: CC(NC(=O)c1ccc(-c2cccnc2)o1)C1CC1] | 1.36 | 257.0 | $^1$H NMR (CD$_3$CN): 0.25 (m, 1H), 0.35 (m, 1H), 0.45 (m, 1H), 0.55 (m, 1H), 1.05 (m, 1H), 1.30 (m, 3H), 3.45 (m, 1H), 6.95 (m, 1H), 7.10 (m, 2H), 7.40 (m, 1H), 8.15 (m, 1H), 8.55 (m, 1H), 9.05 ppm (m, 1H). |
| 9 | 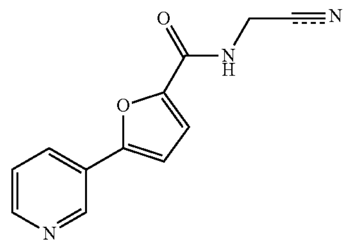 [SMILES: N=CCNC(=O)c1ccc(-c2cccnc2)o1] | 0.43 | 228.1 | $^1$H NMR (CD$_3$CN): 4.25 (m, 2H), 7.00 (d, 1H), 7.20 (d, 1H), 7.45 (m, 1H), 7.70 (br, 1H), 8.15 (d, 1H), 8.55 (m, 1H), 9.05 ppm (s, 1H). |
| 10 | 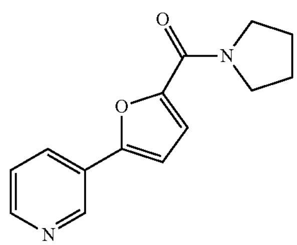 [SMILES: O=C(c1ccc(-c2cccnc2)o1)N1CCCC1] | 1.06 | 243.2 | $^1$H NMR (CD$_3$CN): 1.90 (m, 4H), 3.55 (m, 2H), 3.90 (m, 2H), 7.00 (d, 1H), 7.01 (d, 1H), 7.40 (m, 1H), 8.05 (m, 1H), 8.55 (m, 1H), 9.00 ppm (s, 1H). |
| 11 | 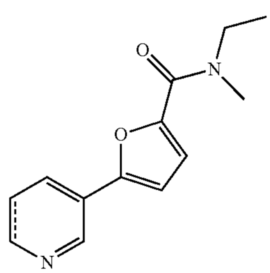 | 1.00 | 231.1 | $^1$H NMR (CD$_3$CN): 1.20 (br, 3H), 3.10 (br, 3H), 3.60 (br, 2H), 6.95 (d, 1H), 7.05 (d, 1H), 7.40 (m, 1H), 8.05 (m, 1H), 8.55 (m, 1H), 8.95 ppm (s, 1H). |
| 12 (Example E) | 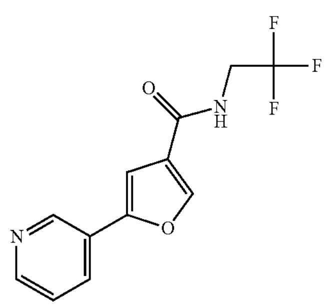 [SMILES: O=C(NCC(F)(F)F)c1coc(-c2cccnc2)c1] | 1.13 | 271.0 | $^1$H NMR (CD$_3$CN): 4.05 (m, 2H), 7.20 (s, 1H), 7.25 (br, 1H), 7.40 (m, 1H), 8.00 (m, 1H), 8.15 (s, 1H), 8.55 (m, 1H), 8.95 ppm (s, 1H). |
| 14 | 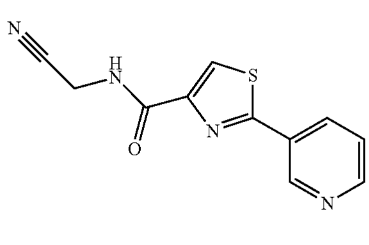 [SMILES: N#CCNC(=O)c1csc(-c2cccnc2)n1] | 0.80 | 245.0 | $^1$H NMR (CD$_3$CN): 4.30 (d, 2H), 7.50 (m, 1H), 8.20 (s, 1H), 8.25 (br, 1H), 8.30 (d, 1H), 8.70 (m, 1H), 9.2 ppm (s, 1H). |

-continued

| Compound number | Structure | logP[1] (HCO$_2$H) | (M + H)[+] | NMR data[2] |
|---|---|---|---|---|
| 15 | 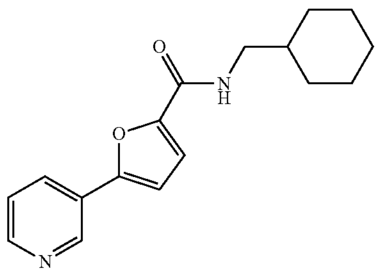 [SMILES: O=C(NCC1CCCCC1)c1ccc(-c2cccnc2)o1] | 2.02 | 285.2 | $^1$H NMR (CD$_3$CN): 1.00-1.90 (m, 11H), 3.20 (m, 2H), 6.90 (d, 1H), 7.10 (d, 1H), 7.40 (m, 1H), 8.10 (m, 1H), 8.50 (m, 1H), 9.00 ppm (s, 1H). |
| 16 | 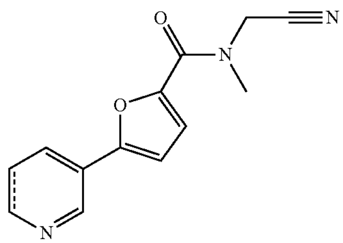 | 0.72 | 242.1 | $^1$H NMR (CD$_3$CN): 3.35 (s, 3H), 4.50 (s, 2H), 7.00 (d, 1H), 7.20 (d, 1H), 7.40 (m, 1H), 8.05 (m, 1H), 8.55 (m, 1H), 9.00 ppm (s, 1H). |
| 17 | 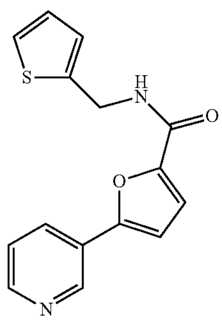 [SMILES: O=C(NCc1cccs1)c1ccc(-c2cccnc2)o1] | 1.46 | 285.1 | $^1$H NMR (CD$_3$CN): 4.70 (m, 2H), 7.00 (m, 2H), 7.05 (m, 1H), 7.20 (m, 1H), 7.30 (m, 1H), 7.40 (m, 1H), 7.80 (br, 1H), 8.10 (m, 1H), 8.50 (m, 1H), 9.00 ppm (s, 1H). |
| 18 | 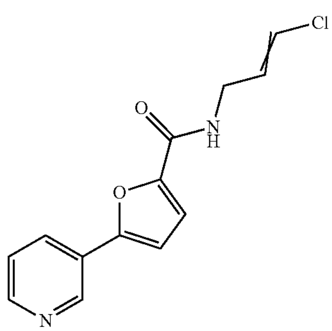 [SMILES: O=C(NCC=CCl)c1ccc(-c2cccnc2)o1] | 1.27; 1.33 (Isomer mixture) | 263.1 | $^1$H NMR (CD$_3$CN): 3.95 (m, 1H), 4.15 (m, 1H), 5.90-6.10 (m, 1H), 6.20-6.30 (m, 1H), 7.00 (d, 1H), 7.10 (d, 1H), 7.40 (m, 2H), 8.10 (m, 1H), 8.50 (m, 1H), 9.00 ppm (s, 1H). |
| 19 | 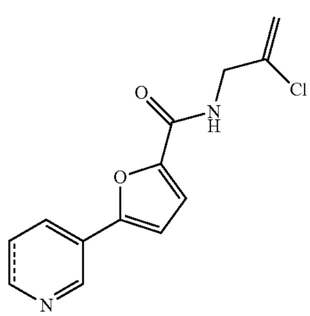 | 1.28 | 263.1 | $^1$H NMR (CD$_3$CN): 4.10 (m, 2H), 5.35 (s, 1H), 5.50 (m, 1H), 7.00 (d, 1H), 7.10 (d, 1H), 7.45 (m, 1H), 7.60 (br, 1H), 8.15 (m, 1H), 8.55 (m, 1H), 9.05 ppm (s, 1H). |

-continued

| Compound number | Structure | logP[1] (HCO$_2$H) | (M + H)[+] | NMR data[2] |
|---|---|---|---|---|
| 20 | 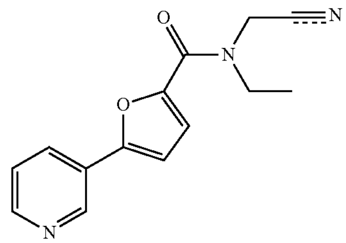 [SMILES: CCN(CC=N)C(=O)c1ccc(-c2cccnc2)o1] | 1.11 | 256.0 | $^1$H NMR (CD$_3$CN): 1.35 (t, 3H), 3.80 (br, 2H), 4.40 (br, 2H), 7.00 (d, 1H), 7.20 (d, 1H), 7.45 (m, 1H), 8.10 (d, 1H), 8.6 (m, 1H), 9.00 ppm (s, 1H). |
| 21 | 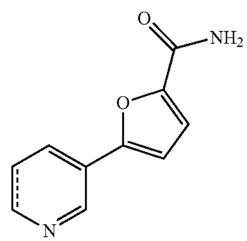 | — | 189.1 | $^1$H NMR (CD$_3$CN): 6.00 (br, 1H), 6.90 (br, 1H), 7.00 (d, 1H), 7.10 (d, 1H), 7.40 (m, 1H), 8.10 (m, 1H), 8.55 (m, 1H), 9.00 ppm (s, 1H). |
| 22 | 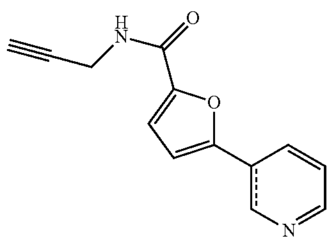 | 0.72 | 227.1 | $^1$H NMR (CD$_3$CN): 2.40 (s, 1H), 4.10 (m, 2H), 7.00 (d, 1H), 7.15 (d, 1H), 7.40 (m, 2H), 8.10 (m, 1H), 8.55 (m, 1H), 9.00 ppm (s, 1H). |
| 23 | 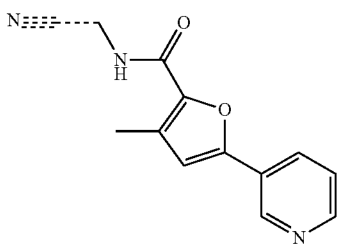 | 1.07 | 242.1 | $^1$H NMR (CD$_3$CN): 2.40 (s, 3H), 4.20 (m, 2H), 6.85 (s, 1H), 7.40 (m, 1H), 7.50 (br, 1H), 8.10 (d, 1H), 8.55 (m, 1H), 9.00 ppm (s, 1H). |
| 24 | 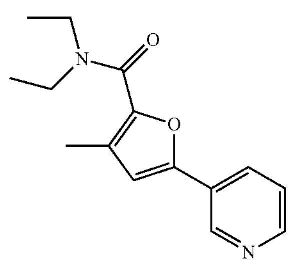 [SMILES: CCN(CC)C(=O)c1oc(-c2cccnc2)cc1C] | 1.58 | 259.2 | $^1$H NMR (CD$_3$CN): 1.25 (t, 6H), 2.25 (s, 3H), 3.50 (q, 4H), 6.80 (s, 1H), 7.35 (m, 1H), 8.00 (d, 1H), 8.50 (m, 1H), 8.90 ppm (s, 1H). |
| 25 (Example F) | 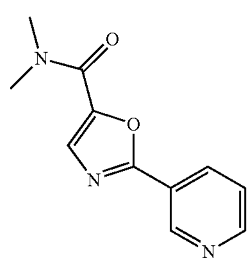 [SMILES: CN(C)C(=O)c1cnc(-c2cccnc2)o1] | 1.43 | 272.1 | $^1$H NMR (CD$_3$CN): 3.05 (br, 3H), 3.30 (br, 3H), 7.50 (m, 1H), 7.65 (s, 1H), 8.35 (d, 1H), 8.70 (m, 1H), 9.25 ppm (s, 1H). |

-continued

| Compound number | Structure | logP[1] (HCO$_2$H) | (M + H)$^+$ | NMR data[2] |
|---|---|---|---|---|
| 26 | 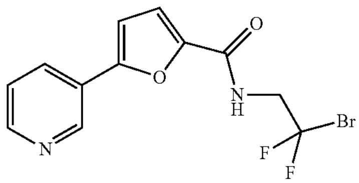 [SMILES: O=C(NCC(F)(F)Br)c1ccc(-c2cccnc2)o1] | 1.49 | 332.9 | $^1$H NMR (CD$_3$CN): 4.25 (m, 2H), 7.00 (d, 1H), 7.20 (d, 1H), 7.40 (m, 1H), 7.60 (br, 1H), 8.10 (d, 1H), 8.55 (m, 1H), 9.05 ppm (s, 1H). |
| 27 | 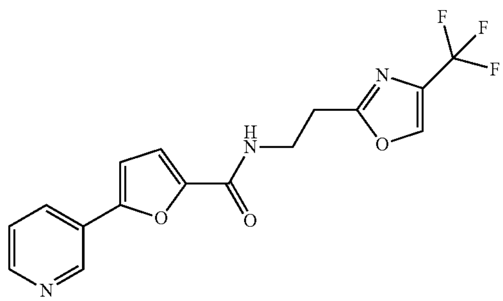 [SMILES: O=C(NCCc1nc(C(F)(F)F)co1)c1ccc(-c2cccnc2)o1] | 1.69 | 368.0 | $^1$H NMR (CD$_3$CN): 3.35 (m, 2H), 3.80 (m, 2H), 7.00 (d, 1H), 7.10 (d, 1H), 7.40 (m, 2H), 7.90 (m, 1H), 8.15 (m, 1H), 8.50 (m, 1H), 9.00 ppm (s, 1H). |
| 28 | 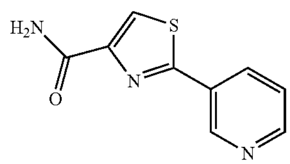 [SMILES: NC(=O)c1csc(-c2cccnc2)n1] | — | 206.0 | $^1$H NMR (d$_6$-DMSO): 7.40 (br. s, 1H), 7.49 (dd, 1H), 7.57 (br. s, 1H), 8.23 (s, 1H), 8.34 (m, 1H), 8.65 (dd, 1H), 9.23 ppm (dd, 1H). |
| 29 | 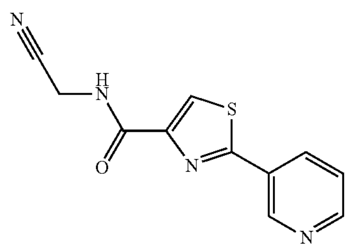 [SMILES: N#CCNC(=O)c1csc(-c2cccnc2)n1] | — | — | $^1$H NMR (CDCl$_3$): 4.43 (d, 2H), 7.46 (dd, 1H), 7.77 (br. t, 1H), 8.22 (m, 1H), 8.25 (s, 1H), 8.76 (dd, 1H), 9.20 ppm (d, 1H). |
| 30 | 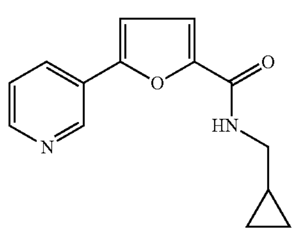 [SMILES: O=C(NCC1CC1)c1ccc(-c2cccnc2)o1] | 1.39 | 243.2 | $^1$H NMR (d$_6$-DMSO): 0.50 (m, 2H), 0.80 (m, 2H), 1.00 (m, 1H), 3.13 (m, 2H), 7.50-7.55 (m, 2H), 7.65 (m, 1H), 8.32 (m, 1H), 8.75 (m, 1H), 9.20 (m, 1H), 9.33 ppm (m, 1H). |
| 31 (Example G) | 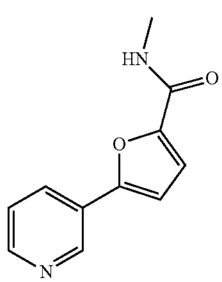 | 0.42 | 203.1 | $^1$H NMR (d$_6$-DMSO): 2.56 (d, 3H), 7.50-7.55 (m, 2H), 7.66 (m, 1H), 8.30 (m, 1H), 8.80 (m, 1H), 9.23 (m, 1H), 9.32 ppm (m, 1H). |

-continued

| Compound number | Structure | logP[1] (HCO₂H) | (M + H)⁺ | NMR data[2] |
|---|---|---|---|---|
| 32 | 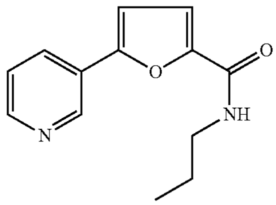 [SMILES: CCCNC(=O)c1ccc(-c2cccnc2)o1] | 0.83 | 231.1 | — |
| 33 (Example H) | 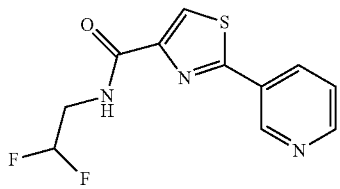 [SMILES: O=C(NCC(F)F)c1csc(-c2cccnc2)n1] | 1.22 | 270.0 | ¹H NMR (d₆-DMSO): 3.65-3.80 (m, 2H), 6.00-6.30 (m, 1H), 7.55 (m, 1H), 8.40 (m, 2H), 8.7 (m, 2H), 9.25 ppm (m, 1H). |
| 34 (Example I) | 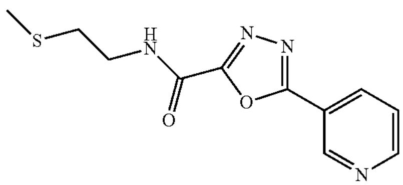 [SMILES: CSCCNC(=O)c1nnc(-c2cccnc2)o1] | 1.13 | 265.1 | ¹H NMR (d₆-DMSO): 2.10 (s, 3H), 2.70 (m, 2H), 3.55 (m, 2H), 7.65 (m, 1H), 8.40 (m, 1H), 8.85 (m, 1H), 9.25 ppm (m, 2H). |
| 35 | 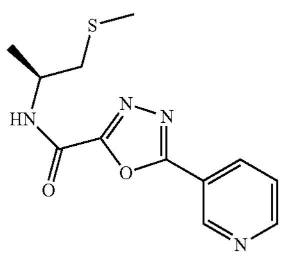 [SMILES: CSC[C@H](C)NC(=O)c1nnc(-c2cccnc2)o1] | 1.39 | 279.1 | ¹H NMR (d₆-DMSO): 1.25 (s, 3H), 2.10 (m, 2H), 2.60-2.80 (m, 1H), 8.40 (m, 1H), 8.85 (m, 1H), 9.10 (m, 1H), 9.25 ppm (m, 1H). |
| 36 (Example J) | 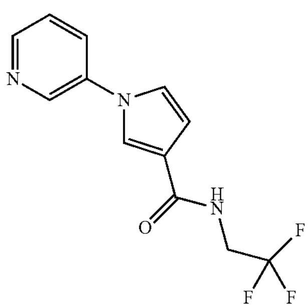 [SMILES: O=C(NCC(F)(F)F)c1ccn(-c2cccnc2)c1] | 1.24 | 270.0 | ¹H NMR (d₆-DMSO): 4.05 (m, 2H), 6.81 (m, 1H), 7.50-7.55 (m, 2H), 8.07 (m, 2H), 8.50 (m, 2H), 8.90 ppm (m, 1H). |
| 37 (Example K) | 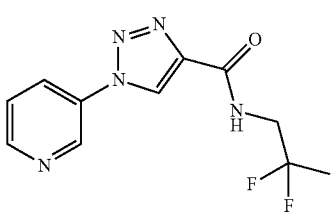 [SMILES: CC(F)(F)CNC(=O)c1cn(-c2cccnc2)nn1] | 1.21 | 267.9 | ¹H NMR (d₆-DMSO): 1.64 (t, 3H), 3.76 (dt, 2H), 7.68 (dd, 1H), 8.40 (m, 1H), 8.74 (dd, 1H), 8.97 (t, 1H), 9.19 (d, 1H), 9.42 ppm (s, 1H). |
| 38 (Example L) | 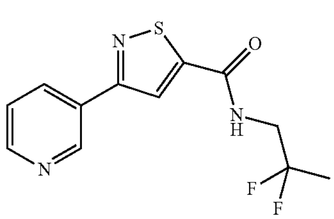 [SMILES: CC(F)(F)CNC(=O)c1cc(-c2cccnc2)ns1] | 1.33 | 284.1 | ¹H NMR (d₆-DMSO): 1.67 (t, 3H), 3.77 (dt, 2H), 7.58 (dd, 1H), 8.34 (m, 1H), 8.68 (dd, 1H), 8.72 (s, 1H), 9.17 (d, 1H), 9.38 ppm (t, 1H). |

| Compound number | Structure | logP[1] (HCO$_2$H) | (M + H)$^+$ | NMR data[2] |
|---|---|---|---|---|
| 39 (Example M) | 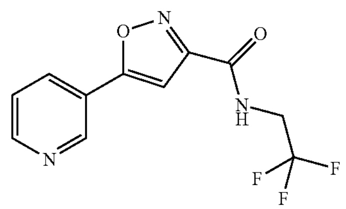 [SMILES: O=C(NCC(F)(F)F)c1cc(-c2cccnc2)on1] | 1.51 | 272.0 | $^1$H NMR (d$_6$-DMSO) 4.04-4.13 (m, 2H), 7.49 (s, 1H), 7.56-7.60 (m, 1H), 8.28-8.31 (m, 1H), 8.70-8.72 (m, 1H), 9.12-9.13 (m, 1H), 9.29 ppm (bs, 1H). |
| 40 | 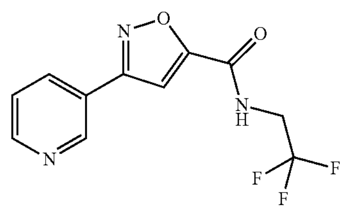 [SMILES: O=C(NCC(F)(F)F)c1cc(-c2cccnc2)no1] | 1.33 | 272.1 | $^1$H NMR (d$_6$-DMSO) 4.06-4.15 (m, 2H), 7.55-7.58 (m, 1H), 7.78 (s, 1H), 8.27-8.30 (m, 1H), 8.71-8.73 (m, 1H), 9.09-9.10 (m, 1H), 9.56 ppm (bs, 1H). |
| 41 (Example N) | 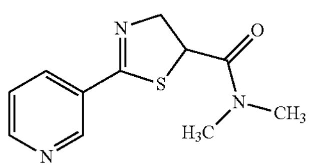 [SMILES: CN(C)C(=O)C1CN=C(c2cccnc2)S1] | | | 2D NMR (CDCl$_3$) 36.3, 37.9 (N—CH$_3$), 48.3 (CH), 67.8 (CH$_2$), 161.7 (C=N), 123.4, 128.6, 135.4, 149.4, 151.9 (Py—C), 169.5 ppm (C=O). |
| 42 | 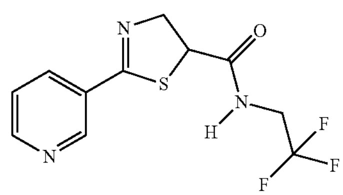 [SMILES: O=C(NCC(F)(F)F)C1CN=C(c2cccnc2)S1] | 0.54 | 290.0 | $^1$H NMR (CD$_3$CN) 3.84-3.96 (m, 2H), 4.52-4.60 (m, 2H), 4.83-4.86 (m, 1H), 7.23 (br, s, 1H), 7.42-7.45 (m, 1H), 8.10-8.12 (m, 1H), 8.67-8.68 (m, 1H), 8.96 ppm (dd, 1H). |
| 43 | 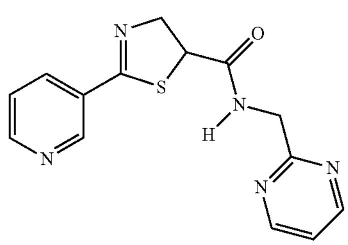 [SMILES: O=C(NCc1ncccn1)C1CN=C(c2cccnc2)S1] | 0.32 | 299.9 | $^1$H NMR (CD$_3$CN) 3.49-4.67 (m, 4H), 4.85-4.90 (m, 1H), 7.26-7.29 (m, 1H), 7.43-7.46 (m, 1H), 7.52 (br, m, 1H), 8.13-8.16 (m, 1H), 8.57-8.69 (m, 2H), 8.98-8.99 ppm (m, 1H). |
| 44 (Example O) | 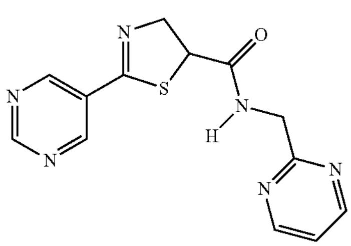 [SMILES: O=C(NCc1ncccn1)C1CN=C(c2cncnc2)S1] | 0.90 | 301.1 | $^1$H NMR (d$_6$-DMSO) 4.66-4.86 (m, 5H), 7.41-7.42 (m, 1H), 8.77-8.79 (m, 2H), 8.87-8.89 (m, 1H), 9.11 (d, 2H), 9.34 ppm (d, 1H). |
| 45 | 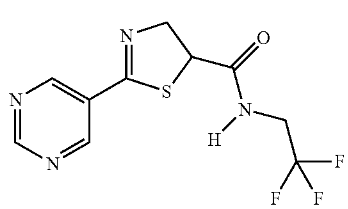 [SMILES: O=C(NCC(F)(F)F)C1CN=C(c2cncnc2)S1] | 1.40 | 290.9 | $^1$H NMR (CD$_3$CN) 3.86-3.95 (m, 2H), 4.57-4.57 (m, 1H), 4.62-4.64 (m, 1H), 4.85-4.89 (m, 1H), 7.20 (m, 1H), 9.23 (d, 1H), 9.08 ppm (d, 2H). |

-continued

| Compound number | Structure | logP¹ (HCO₂H) | (M + H)⁺ | NMR data² |
|---|---|---|---|---|
| 46 | 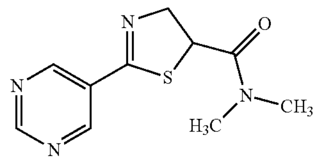 [SMILES: CN(C)C(=O)C1CN=C(c2cncnc2)S1] | 0.99 | 237.1 | ¹H NMR (CD₃CN) 2.90 (s, 3H), 3.04 (s, 3H), 4.47-4.52 (m, 1H), 4.94-4.98 (m, 2H), 9.05 (d, 1H), 9.22 ppm (d, 2H). |
| 47 (Example P) | 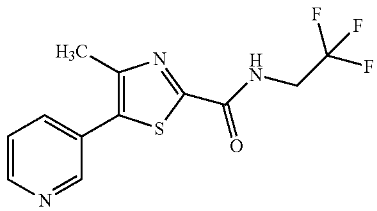 [SMILES: Cc1nc(C(=O)NCC(F)(F)F)sc1-c1cccnc1] | 1.74 | 302.1 | ¹H-NMR (CDCl₃) 2.54 (s, 3H), 4.11 (m, 2H), 7.41 (m, 1H), 7.55 (br, 1H), 7.78 (m, 1H), 8.68 (m, 1H), 8.75 ppm (m, 1H). |
| 48 (Example Q) | 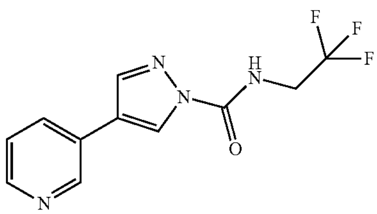 [SMILES: O=C(NCC(F)(F)F)n1cc(-c2cccnc2)cn1] | 1.74 | 302.1 | ¹H NMR (d₆-DMSO) 4.08 (m, 2H), 7.40 (m, 1H), 8.10 (m, 1H), 8.38 (m, 1H), 8.48 (m, 1H), 8.89 (m, 1H), 9.00 ppm (m, 2H). |
| 49 (Example R) | 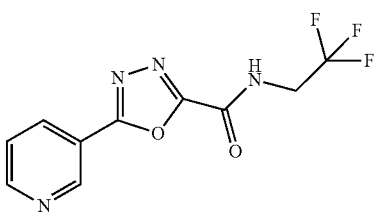 [SMILES: O=C(NCC(F)(F)F)c1nnc(-c2cccnc2)o1] | 1.21 | 272.2 | ¹H NMR (d₆-DMSO): 4.15 (m, 2H) 7.7 (m, 1H) 8.45 (m, 1H) 8.85 (m, 1H) 9.25 (s, 1H) 10 ppm (m, 1H). |
| 50 (Example S) | 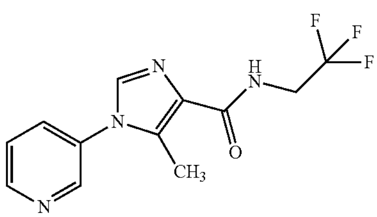 [SMILES: Cc1c(C(=O)NCC(F)(F)F)ncn1-c1cccnc1] | 1.28 | 284.2 | ¹H NMR (d₆-DMSO): 2.45 (s, 3H), 4.0 (m, 1H), 7.65 (m, 1H), 8 (s, 1H), 8.05 (m, 1H), 8.55 (m, 1H), 8.7 (m, 1H), 8.75 ppm (s, 1H). |

1 Method Description for Determination of the logP values and Mass Detection

The logP values reported in the table were determined in accordance with EEC Directive 79/831 Annex V.A8 by HPLC (High Performance Liquid Chromatography) using a reverse-phase column (C 18). Temperature: 55° C.

Eluents for determination in the acidic range (pH 3.4):
Eluent A: acetonitrile+1 ml formic acid/l. Eluent B: water+ 0.9 ml formic acid/l.
Gradient: from 10% eluent A/90% eluent B to 95% eluent A/5% eluent B in 4.25 min.

The calibration was effected with unbranched alkan-2-ones (having 3 to 16 carbon atoms) with known logP values (logP values determined on the basis of the retention times by linear interpolation between two successive alkanones). The $\lambda_{max}$ values were determined in the maxima of the chromatographic signals using the UV spectra from 200 nm to 400 nm. The mass was detected (M⁺, m/z) by means of an Agilent MSD mass spectrometer.

2 Measurement of the NMR Spectra

The NMR spectra were determined using a Broker Avance 400 fitted with a flow probe head (volume 60 μl). The solvents used were CD₃CN, CDCl₃ or d₆-DMSO, with tetramethylsilane (0.00 ppm) used as a reference. In individual cases, the NMR spectra were determined with a Bruker Avance II 600 or a Varian Unity Inova 400.

The splitting of the signals was described as follows: s (singlet), d (doublet), t (triplet), q (quartet), quin (quintet), m (multiplet), br (broad).

Biological Examples

*Myzus persicae* Test (Spray Treatment)
Solvent: 78 parts by weight of acetone
1.5 parts by weight of dimethylformamide
Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration. Discs of Chinese cabbage (*Brassica pekinensis*) infested by all stages of the green peach aphid (*Myzus persicae*) are sprayed with an active ingredient preparation of the desired concentration.

After 6 days, the efficacy in % is determined. 100% means that all of the aphids have been killed; 0% means that none of the aphids have been killed.

In this test, for example, the following compounds of the Preparation Examples showed, at an application rate of 500 g/ha, an efficacy of 100%: 1, 2, 3, 6, 7, 9, 11, 17, 19, 20, 22, 23, 28, 30, 31, 32, 33, 37, 38, 41, 43, 45.

In this test, for example, the following compounds of the Preparation Examples showed, at an application rate of 500 g/ha, an efficacy of 90%: 12, 16, 18, 24, 25, 36.

In this test, for example, the following compounds of the Preparation Examples showed, at an application rate of 500 g/ha, an efficacy of 80%: 8, 14, 27, 29, 35, 44.

*Spodoptera frugiperda* Test (Spray Treatment)
Solvent: 78.0 parts by weight of acetone
 1.5 parts by weight of dimethylformamide
Emulsifier: 0.5 part by weight of alkylaryl polyglycol ether To prepare an appropriate active ingredient preparation, 1 part by weight of active ingredient is mixed with the stated amounts of solvent and emulsifier, and the concentrate is diluted with emulsifier-containing water to the desired concentration. Discs of maize leaves (*Zea mays*) are sprayed with an active ingredient preparation of the desired concentration and, after drying, populated with the armyworm (*Spodoptera frugiperda*).

After 7 days, the efficacy in % is determined. 100% means that all caterpillars have been killed; 0% means that none of the caterpillars have been killed.

In this test, for example, the following compound of the Preparation Examples showed, at an application rate of 500 g/ha, an efficacy of 100%: 37.

The invention claimed is:
1. A compound of the formula (I)

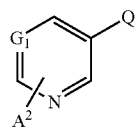

(I)

in which
$G^1$ is N or $C-A^1$,
$A^1$ is hydrogen, halogen, cyano, nitro, $C_1-C_6$-alkyl, $C_3-C_6$-cycloalkyl, $C_1-C_3$-haloalkyl or $C_1-C_6$-alkoxy,
$A^2$ is hydrogen, halogen, cyano, nitro, $C_1-C_6$-alkyl, $C_3-C_6$-cycloalkyl or $C_1-C_6$-alkoxy,
Q is

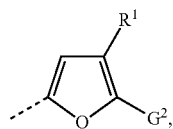

$R^1$ is hydrogen, $C_1-C_6$-alkyl, $C_3-C_6$-cycloalkyl, halogen, cyano, $C_1-C_3$-haloalkyl, hydroxyl or $C_1-C_6$-alkoxy,
$G^2$ is $C(=X)NR^3R^4$,
X is oxygen or sulphur,
$R^3$ is hydrogen, $C_1-C_6$-alkyl, $C_3-C_6$-cycloalkyl, $C_1-C_6$-haloalkyl, cyano-$C_1-C_6$-alkyl, $C_1-C_6$-alkoxy, $C_1-C_6$-haloalkoxy, $C_2-C_6$-alkenyl, $C_1-C_6$-alkoxy-$C_1-C_6$-alkyl, optionally halogen-substituted $C_1-C_6$-alkylcarbonyl, optionally halogen-substituted $C_1-C_6$-alkoxycarbonyl, $C_3-C_6$-cycloalkylcarbonyl which is optionally substituted by halogen, $C_1-C_6$-alkyl, optionally halogen-substituted $C_1-C_6$-alkyl, $C_1-C_6$-alkoxy, $C_1-C_6$-haloalkyl or cyano; or a cation,
$R^4$ is cyano, $C_1-C_6$-alkyl which is optionally substituted by halogen, cyano, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl or $C_1-C_6$-haloalkylsulphonyl; $C_2-C_6$-alkenyl which is optionally substituted by halogen, cyano, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl or $C_1-C_6$-haloalkylsulphonyl; $C_2-C_6$-alkynyl which is optionally substituted by halogen, cyano, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl or $C_1-C_6$-haloalkylsulphonyl; $C_1-C_6$-alkoxy, $C_1-C_6$-haloalkoxy, optionally halogen-substituted bis($C_1-C6$-alkoxy)-$C_1-C_6$-alkyl, optionally halogen-substituted bis($C_1-C_6$-alkylthio)-$C_1-C_6$-alkyl, optionally halogen-substituted $C_1-C_6$-alkylcarbonyl-$C_1-C_6$-alkyl, optionally halogen-substituted $C_1-C_6$-alkylsulphinyl-$C_1-C_6$-alkyl, optionally halogen-substituted $C_1-C_6$-alkylsulphonyl-$C_1-C_6$-alkyl, optionally halogen-substituted $C_1-C_6$-alkoxycarbonyl-$C_1-C_6$-alkyl, $C_2-C_4$-alkynyloxy, optionally halogen-substituted $C_3-C_6$-cycloalkylcarbonyl, optionally halogen-substituted $C_3-C_6$-cycloalkyl-$C_1-C_6$-alkyl, $C_3-C_6$-cycloalkyl which is optionally substituted by halogen, $C_1-C_6$-alkyl, $C_1-C_6$-haloalkyl, $C_1-C_6$-alkoxy or $C_1-C_6$-haloalkoxy, wherein the cycloalkyl ring may contain one to three heteroatoms selected from the group consisting of sulphur, oxygen where oxygen atoms must not be immediately adjacent and nitrogen; $C_3-C_6$-cycloalkenyl which is optionally substituted by halogen, $C_1-C_6$-alkyl, $C_1-C_6$-haloalkyl, $C_1-C_6$-alkoxy or $C_1-C_6$-haloalkoxy, wherein the cycloalkenyl ring may contain one to three heteroatoms selected from the group consisting of sulphur, oxygen where oxygen atoms must not be immediately adjacent and nitrogen; aryl which is optionally substituted by halogen, cyano, nitro, $C_1-C_6$-alkyl, $C_1-C_6$-haloalkyl, $C_3-C_6$-cycloalkyl, $C_1-C_6$-alkoxy, $C_1-C_6$-haloalkoxy, $C_1-C_6$-alkylthio, $C_1-C_6$-haloalkylthio, $C_1C_6$-alkylsulphinyl, $C_1-C_6$-haloalkylsulphinyl, $C_1-C_6$-alkylsulphonyl, $C_1-C_6$-haloalkylsulphonyl, amino, $C_1-C_6$-alkylamino, di($C_1-C_6$-alkyl)amino, $C_1-C_6$-alkylcarbonylamino, $C_1-C_6$-alkoxycarbonylamino, $C_1-C_6$-alkoxy-$C_1-C_6$-alkyl, $C_1-C_6$-haloalkoxy-$C_1-C_6$-alkyl, $C_2-C_6$-alkenyl, $C_2-C_6$-alkynyl, $C_3-C_6$-cycloalkyl-$C_1-C_6$-alkyl, $C_1-C_6$-alkylcarbonyl, $C_1-C_6$-alkoxycarbonyl or aminocarbonyl; heteroaryl which is optionally substituted by halogen, cyano, nitro, $C_1-C_6$-alkyl, $C_1-C_6$-haloalkyl, $C_3-C_6$-cycloalkyl, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl, $C_1-C_6$-haloalkylsulphonyl, amino, $C_1-C_6$-alkylamino, di($C_1-C_6$-alkyl)amino, $C_1-C_6$-alkylcarbonylamino, $C_1-C_6$-alkoxycarbonylamino, $C_1-C_6$-alkoxy-$C_1-C_6$-alkyl, $C_1-C_6$-haloalkoxy-$C_1-C_6$-alkyl, $C_2-C_6$-alkenyl, $C_2-C_6$-alkynyl, $C_3-C_6$-cycloalkyl-$C_1-C_6$-alkyl, $C_1-C_6$-alkylcarbonyl or $C_1$-$C_6$-alkoxycarbonyl; heterocyclyl-$C_1$-$C_6$-alkyl which is optionally substituted by halogen, cyano, nitro, $C_1$-$C_6$alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, amino, $C_1$-$C_6$-alkylamino, di($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl or aminocarbonyl; aryl-$C_1$-$C_6$-alkyl which is optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, amino, $C_1$-$C_6$-alkylamino, di($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl or aminocarbonyl; heteroaryl-$C_1$-$C_6$-alkyl which is optionally substituted by halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, amino, $C_1$-$C_6$-alkylamino, di($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl or $C_1$-$C_6$-alkoxycarbonyl; or $NR^5R^6$ in which $R^5$ and $R^6$ are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl, $C_1$-$C_6$-alkoxylcarbonyl, hetaryl and heterocyclyl, or $R^5$ and $R^6$ together with the nitrogen atom to which they are bonded form an optionally halogen-substituted heterocycle, or $R^3$ and $R^4$ may also, together with the nitrogen atom to which they are bonded, form a 3- to 7- membered ring which is optionally substituted by $C_1$-$C_6$-alkyl, $C_1$-$C_6$-alkoxy or halogen, wherein said 3- to 7- membered ring optionally contains one or two heteroatoms selected from the group of oxygen, nitrogen and sulphur, where oxygen atoms must not be immediately adjacent.

2. The compound of formula (I) according to claim 1, in which $G^1$ is N or C-$A^1$;

$A^1$ is hydrogen, halogen, cyano, nitro, $C_1$-$C_4$-alkyl, $C_3$-$C_6$-cycloalkyl, $C_1$-$C_3$-haloalkyl or $C_1$-$C_4$-alkoxy, $A^2$ is hydrogen, halogen, cyano, nitro, $C_1$-$C_4$-alkyl, $C_3$-$C_6$-cycloalkyl or $C_1$-$C_4$-alkoxy, Q is

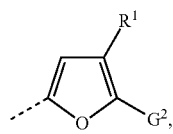

$R^1$ is hydrogen, $C_1$-$C_4$-alkyl, $C_3$-$C_6$-cycloalkyl, halogen, cyano, $C_1$-$C_3$-haloalkyl, hydroxyl or $C_1$-$C_4$-alkoxy, $G^2$ is C(=X)$NR^3R^4$, X is oxygen or sulphur, $R^3$ is hydrogen, $C_1$-$C_4$-alkyl, $C_3$-$C_6$-cycloalkyl, $C_1$-$C_4$-haloalkyl, cyano-$C_1$-$C_4$-alkyl, $C_1$-$C_4$-alkoxy, $C_1$-$C_4$-haloalkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl, $C_3$-$C_6$-cycloalkylcarbonyl which is optionally substituted by halogen, $C_1$-$C_4$-alkyl, $C_1$-$C_4$-alkoxy, $C_1$-$C_4$-haloalkyl and cyano; or a cation, $R^4$ is cyano, $C_1$-$C_4$-alkyl which is optionally substituted by halogen, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl; $C_2$-$C_4$-alkenyl which is optionally substituted by halogen, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl; $C_2$-$C_4$-alkynyl which is optionally substituted by halogen, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl; $C_1$-$C_4$-alkoxy, $C_1$-$C_4$-haloalkoxy, optionally halogen-substituted bis($C_1$-$C_4$-alkoxy)-$C_1$-$C_4$-alkyl, optionally halogen-substituted bis($C_1$-$C_4$-alkylthio)-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, optionally halogen-substituted $C_1$-$C_4$-alkoxycarbonyl-$C_1$-$C_4$-alkyl, $C_2$-$C_4$-alkynyloxy, optionally halogen-substituted $C_3$-$C_6$-cycloalkylcarbonyl, optionally halogen-substituted $C_3$-$C_6$-cycloalkyl-$C_1$-$C_4$-alkyl, $C_3$-$C_6$-cycloalkyl which is optionally substituted with halogen, $C_1$-$C_4$-alkyl, $C_1$-$C_4$-haloalkyl, $C_1$-$C_4$-alkoxy or $C_1$-$C_4$-haloalkoxy, wherein the cycloalkyl ring may contain one to three heteroatoms selected from the group consisting of sulphur, oxygen where oxygen atoms must not be immediately adjacent and nitrogen; $C_3$-$C_6$-cycloalkenyl which is optionally substituted with halogen, $C_1$-$C_4$-alkyl, $C_1$-$C_4$-haloalkyl, $C_1$-$C_4$-alkoxy or $C_1$-$C_4$-haloalkoxy, wherein the cycloalkenyl ring may contain one to three heteroatoms selected from the group consisting of sulphur, oxygen where oxygen atoms must not be immediately adjacent and nitrogen; aryl which is optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, amino, $C_1$-$C_4$-alkylamino, di($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl; heteroaryl which is optionally substituted by halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, amino, $C_1$-$C_4$-alkylamino, di($C_1$-$C_4$-alkyl)amino, $C_1$-$C_4$-alkylcarbonylamino, $C_1$-$C_4$- alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl or $C_1$-$C_4$-alkoxycarbonyl; heterocyclyl-$C_1$-$C_4$-alkyl which is optionally substituted by halogen, cyano, nitro, $C_1$-$C_4$-alkyl-, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, amino, $C_1$-$C_4$-alkylamino, di($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl; aryl-$C_1$-$C_4$-alkyl which is optionally substituted by halogen, cyano, nitro, $C_1$-$C_4$-alkyl-, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, amino, $C_1$-$C_4$-alkylamino, di($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl or aminocarbonyl; heteroaryl-$C_1$-$C_4$-alkyl which is optionally substituted by halogen, cyano, nitro, $C_1$-$C_4$-alkyl-,$C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, amino, $C_1$-$C_4$-alkylamino, di($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl or $C_1$-$C_4$-alkoxycarbonyl; or $NR^5R^6$ in which $R^5$ and $R^6$ are each independently a radical from the group of hydrogen, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylcarbonyl, $C_1$-$C_4$-alkoxylcarbonyl, hetaryl and heterocyclyl, or $R^5$ and $R^6$ together with the nitrogen atom to which they are bonded form an optionally halogen-substituted heterocycle, or $R^3$ and $R^4$ may also, together with the nitrogen atom to which they are bonded, form a 3- to 7-membered ring which is optionally substituted by $C_1$-$C_4$-alkyl, $C_1$-$C_4$-alkoxy or halogen; wherein the 3- to 7-membered ring optionally contains one or two heteroatoms selected from the group of oxygen, nitrogen and sulphur, where oxygen atoms must not be immediately adjacent.

3. The compound of formula (I) according to claim 1, in which $G^1$ is C-$A^1$,
$A^1$ is hydrogen,
$A^2$ is hydrogen,
Q is

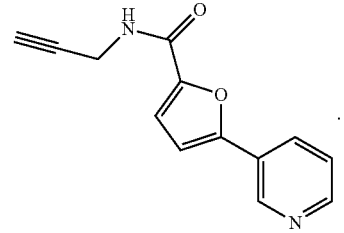 [SMILES: C#CCNC(=O)c1ccc(-c2cccnc2)o1]

$R^1$ is hydrogen or $C_1$-$C_4$-alkyl,
$G^2$ is C(=X)$NR^3R^4$,
X is oxygen,
$R^3$ is hydrogen or $C_1$-$C_4$-alkyl,
$R^4$ is $C_1$-$C_4$-alkyl which is optionally substituted by halogen, cyano or $C_1$-$C_4$-alkylthio; $C_2$-$C_4$-alkenyl which is optionally substituted by halogen, cyano or $C_1$-$C_4$-alkylthio; $C_2$-$C_4$-alkynyl which is optionally substituted by halogen, cyano or $C_1$-$C_4$-alkylthio; optionally halogen-substituted $C_3$-$C_6$-cycloalkyl-$C_1$-$C_4$-alkyl and optionally $C_1$-$C_4$-haloalkyl-substituted heteroaryl-$C_1$-$C_4$-alkyl, or $R^3$ and $R^4$ may also, together with the nitrogen atom to which they are bonded, form a 3-to 7-membered ring which does not contain any further heteroatoms.

4. The compound of formula (I) according to claim 1 having the formula:

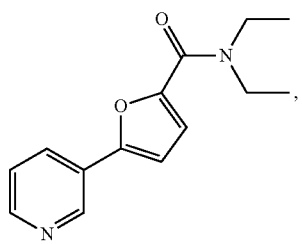

5. The compound of claim 1, wherein said cation is a mono- or divalent metal ion or a quaternary ammonium group optionally substituted with $C_1$-$C_4$-alkyl or aryl-$C_1$-$C_4$-alkyl substituents.

6. The compound of claim 2, wherein said cation is a mono- or divalent metal ion or a quaternary ammonium group optionally substituted with $C_1$-$C_4$-alkyl or aryl-$C_1$-$C_4$-alkyl substituents.

7. The compound of claim 1 wherein $R^4$ is $C_1$-$C_6$ alkyl substituted by halogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl or $C_1$-$C_6$-haloalkylsulphonyl.

8. The compound of claim 1, wherein $R^3$ and $R^4$ are $C_1$-$C_6$-alkyl.

9. The compound of claim 1, wherein $R^4$ is $C_1$-$C_6$-alkyl substituted by halogen.

10. The compound of claim 1, wherein $R^4$ is $C_1$-$C_6$-alkyl substituted by cyano.

11. The compound of claim 1, wherein $R^3$ and $R^4$ together with the nitrogen atom to which they are bonded form a 3-to 7-membered ring.

12. The compound of claim 1, wherein $R^4$ is $C_2$-$C_6$-alkenyl substituted by halogen.

13. The compound of claim 1 selected from the group consisting of

89
-continued
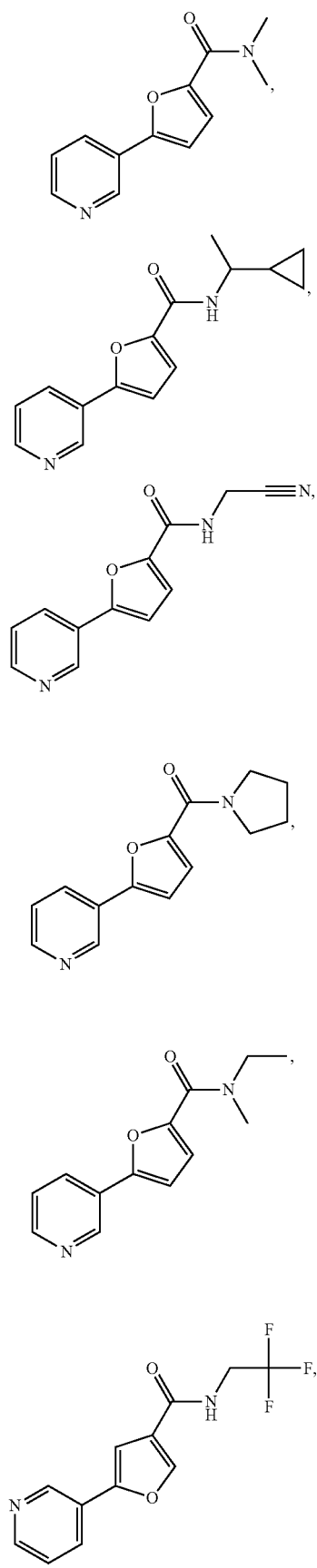
90
-continued
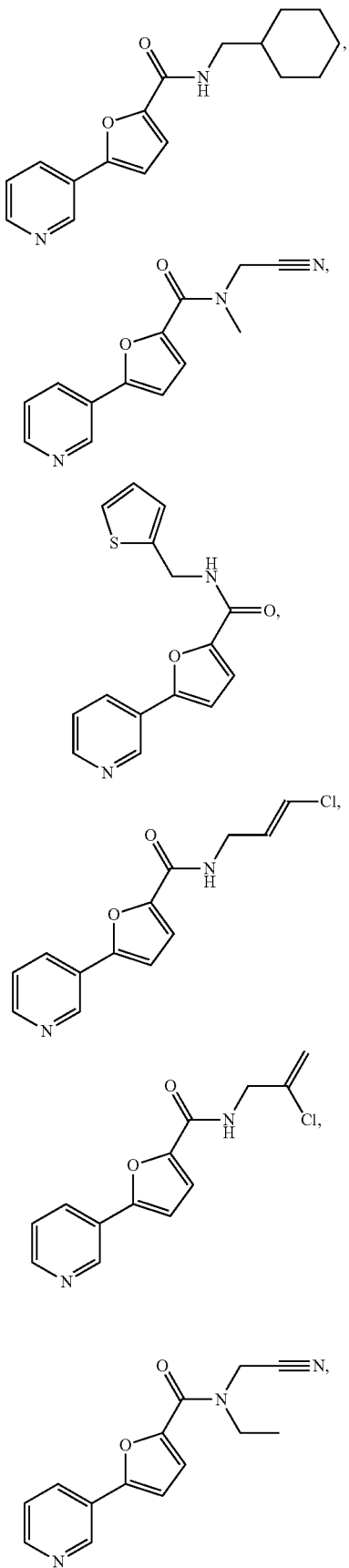

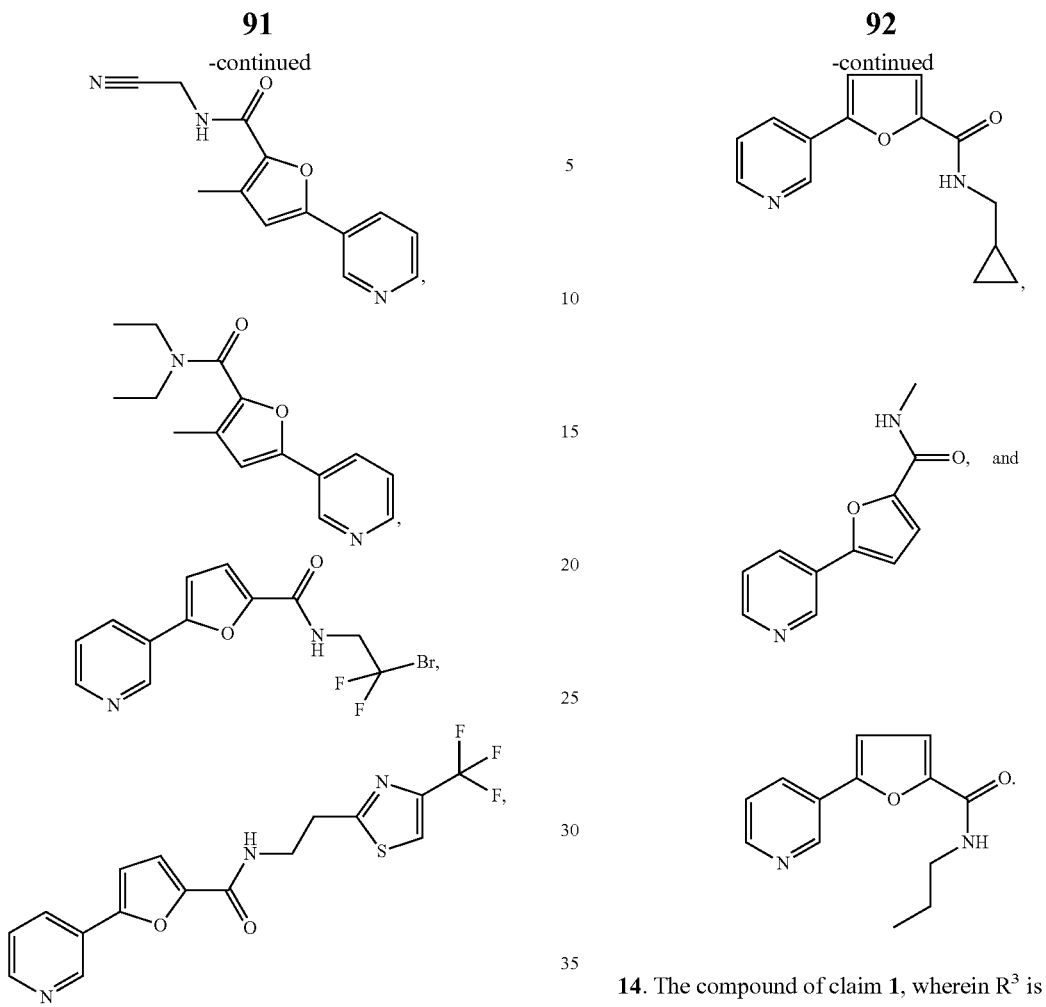
14. The compound of claim 1, wherein $R^3$ is a cation.